(12) United States Patent
Penafuerte Diaz

(10) Patent No.: US 12,329,803 B2
(45) Date of Patent: Jun. 17, 2025

(54) METHOD OF REDUCING OR TREATING FIBROSIS BY ADMINISTERING AN INTERLEUKIN-2/TGF-BETA RECEPTOR FUSION POLYPEPTIDE

(71) Applicant: Cura Therapeutics, Inc., Montreal (CA)

(72) Inventor: Claudia Ania Penafuerte Diaz, Montreal (CA)

(73) Assignee: Cura Therapeutics Inc., Montreal (CA)

( * ) Notice: Subject to any disclaimer, the term of this patent is extended or adjusted under 35 U.S.C. 154(b) by 0 days.

(21) Appl. No.: 18/309,450

(22) Filed: Apr. 28, 2023

(65) Prior Publication Data

US 2023/0364186 A1    Nov. 16, 2023

Related U.S. Application Data

(62) Division of application No. 17/673,691, filed on Feb. 16, 2022, now Pat. No. 11,672,844.

(60) Provisional application No. 63/150,450, filed on Feb. 17, 2021.

(51) Int. Cl.
| | |
|---|---|
| A61K 38/17 | (2006.01) |
| A61P 35/00 | (2006.01) |
| C07K 14/54 | (2006.01) |
| C07K 14/55 | (2006.01) |
| C07K 14/71 | (2006.01) |

(52) U.S. Cl.
CPC ............ *A61K 38/179* (2013.01); *A61P 35/00* (2018.01); *C07K 14/5443* (2013.01); *C07K 14/55* (2013.01); *C07K 14/71* (2013.01); *C07K 2319/30* (2013.01)

(58) Field of Classification Search
CPC .. A61K 38/179; C07K 14/5443; C07K 14/55; C07K 14/71; C07K 2319/30
See application file for complete search history.

(56) References Cited

U.S. PATENT DOCUMENTS

| | | |
|---|---|---|
| 8,283,449 B2 | 10/2012 | Galipeau et al. |
| 8,574,548 B2 | 11/2013 | O'connor-mccourt et al. |
| 11,672,844 B2 | 6/2023 | Penafuerte Diaz |
| 2011/0150828 A1 | 6/2011 | Galipeau et al. |
| 2018/0155439 A1 | 6/2018 | Galipeau et al. |
| 2022/0127332 A1 | 4/2022 | Penafuerte Diaz |
| 2022/0257712 A1 | 8/2022 | Penafuerte Diaz |

FOREIGN PATENT DOCUMENTS

| | | |
|---|---|---|
| EP | 3260470 A1 | 12/2017 |
| WO | 2009152610 A1 | 12/2009 |
| WO | 2016200881 A1 | 12/2016 |
| WO | 2020047299 A1 | 3/2020 |
| WO | 2020047473 A1 | 3/2020 |
| WO | 2021041886 A1 | 3/2021 |
| WO | 2021096275 A1 | 5/2021 |
| WO | 2022086988 A1 | 4/2022 |
| WO | 2022178033 A1 | 8/2022 |

OTHER PUBLICATIONS

International Search Report and Written Opinion for Patent Application No. PCT/US2021/055646, mailed on Jan. 11, 2022, 11 pages.
International Search Report and Written Opinion for Patent Application No. PCT/US2022/016662, mailed on May 13, 2022, 17 pages.
Office Action received in U.S. Appl. No. 17/574,479, mailed on Jun. 10, 2022, 7 pages.
Restriction Requirement received in U.S. Appl. No. 17/574,479, mailed on Apr. 15, 2022, 12 pages.
Restriction Requirement received in U.S. Appl. No. 17/574,479, mailed on Mar. 7, 2022, 8 pages.
Cesana et al. (May 2007) "Low-dose Interleukin-2 Administered Pre-operatively to Patients with Gastric Cancer Activates Peripheral and Peritumoral Lymphocytes but Does Not Affect Prognosis", Annals of Surgical Oncology, 14 (4):1295-1304.
Dammeijer et al. (Jun. 2017) "Rationally Combining Immunotherapies to Improve Efficacy of Immune Checkpoint Blockade in Solid Tumors", Cytokine & Growth Factor Reviews, 36:5-15.
Dong et al. (Jan. 2007) "The Type III TGF-beta Receptor Suppresses Breast Cancer Progression", Journal of clinical investigation, 117(1):206-217.
Frieman et al. (Apr. 8, 2004) "SARS-CoV Pathogenesis Is Regulated by a STAT1 Dependent but a Type I, II and III Interferon Receptor Independent Mechanism", PLOS Pathogens, 6(4):e1000849 (14 pages).
Heldin et al. (Aug. 2016) "Signaling Receptors for TGF-β Family Members", Cold Spring Harbor Perspectives in Biology, 8(8):1-33.
Jamilloux et al. (Jul. 2020) "Should We Stimulate or Suppress Immune Responses in Covid-19? Cytokine and Anti-cytokine Interventions", Autoimmunity Reviews, 19(7):102567 (14 pages).
Kim et al. (Aug. 2012) "TGF-Beta Sensitivity is Determined by N-linked Glycosylation of the Type II TGF-Beta Receptor.", Biochemical Journal, 445(3):403-411.
Kint et al. (Dec. 1, 2015) "Infectious Bronchitis Coronavirus Inhibits STAT1 Signaling and Requires Accessory Proteins for Resistance to Type I Interferon Activity", Journal of Virology, 89(23):12047-12057.
Kopecky-Bromberg et al. (Jan. 2007) "Severe Acute Respiratory Syndrome Coronavirus Open Reading Frame (ORF) 3b, ORF 6, and Nucleocapsid Proteins Function as Interferon Antagonists", Journal of Virology, 81 (2):548-557.
Malek et al. (Sep. 2004) "Tolerance, not Immunity, Crucially Depends on IL-2", Nature Reviews Immunology, 4(9):665-674.

(Continued)

*Primary Examiner* — Robert S Landsman
(74) *Attorney, Agent, or Firm* — Mintz, Levin, Cohn, Ferris, Glovsky and Popeo, P.C.

(57) ABSTRACT

Provided are multi-functional and multi-valent fusion polypeptides comprising an interleukin polypeptide and two or more TGFβ ligand-binding polypeptides. The compositions and methods provided herein are useful in the application of treating and/or preventing pathogenic infections.

23 Claims, 22 Drawing Sheets

Specification includes a Sequence Listing.

(56) References Cited

OTHER PUBLICATIONS

Marabondo et al. (Dec. 2017) "High-dose Interleukin-2 (IL-2) for the Treatment of Melanoma: Safety Considerations and Future Directions", Expert Opinion on Drug Safety, 16(12):1347-1357.
Massague, J. (Sep. 20, 2012) "TGFBeta Signaling in Context", Nature Reviews Molecular Cell Biology, 13:616-630.
Mendy et al. (Jun. 27, 2020) "Factors Associated with Hospitalization and Disease Severity in a Racially and Ethnically Diverse Population of COVID-19 Patients", medRxiv, 24 pages.
Muraoka et al. (Jun. 2002) "Blockade of TGF-beta Inhibits Mammary Tumor Cell Viability, Migration, and Metastases", Journal of Clinical Investigation, 109(12):1551-1559.
Penafuerte et al. (Mar. 1, 2012) "B Effector Cells Activated by a Chimeric Protein Consisting of IL-2 and the Ectodomain of TGF-β Receptor II Induce Potent Antitumor Immunity", Cancer Research, 72(5):1210-1220.
Penafuerte et al. (Mar. 2012) "Fist, a Sword and Shield Fusokine for Cancer Immunotherapy", Oncoimmunology, 1(2):224-226.
Penafuerte et al. (Jun. 15, 2011) "Novel TGF-Beta Antagonist Inhibits Tumor Growth and Angiogenesis by Inducing IL-2 Receptor-Driven STAT1 Activation", Journal of Immunology, 186(12):6933-6944.
Penafuerte et al. (Dec. 1, 2009) "The Human Ortholog of Granulocyte Macrophage Colony-Stimulating Factor and Interleukin-2 Fusion Protein Induces Potent Ex vivo Natural Killer Cell Activation and Maturation", Cancer Research, 69(23):9020-9028.
Rafei et al. (Mar. 1, 2007) "A GMCSF and IL-15 Fusokine Leads to Paradoxical Immunosuppression in Vivo via Asymmetrical JAK/STAT Signaling through the IL-15 Receptor Complex", Blood, 109(5):2234-2242.
Spolski et al. (Oct. 2018) "Biology and Regulation of IL-2: From Molecular Mechanisms to Human Therapy", Nature Reviews Immunology, 18(10):648-659.
Stauber et al. (Feb. 13, 2006) "Crystal Structure of the IL-2 Signaling Complex: Paradigm for a Heterotrimeric Cytokine Receptor", Proceedings of the National Academy of Sciences of the United States of America, 103 (8):2788-2793.
Totura et al. (Jun. 2012) "SARS Coronavirus Pathogenesis: Host Innate Immune Responses and Viral Antagonism of Interferon", Current Opinion in Virology, 2(3):264-275.
Tzai et al. (May-Jun. 1998) "Antisense Oligonucleotide Specific for Transforming Growth Factor-beta 1 Inhibit Both In Vitro and In Vivo Growth of MBT-2 murine Bladder Cancer", Anticancer Research, 18(3A):1585-1599.
Wang et al. (Feb. 2006) "An Oncolytic Adenovirus Expressing Soluble Transforming Growth Factor-beta Type II Receptor for Targeting Breast Cancer: In Vitro Evaluation", Molecular cancer therapeutics, 5(2):367-373.
Wrangle et al. (Feb. 1, 2018) "IL-2 and Beyond in Cancer Immunotherapy", Journal of Interferon & Cytokine Research, 38(2):45-68.
Yakymovych et al. (Aug. 7, 2002) "Inhibition of transforming growth factor-beta signaling by low molecular weight compounds interfering with ATP- or substrate-binding sites of the TGF beta type I receptor kinase", Biochemistry, 41 (36):11000-11007.
Zhang et al. (Nov. 1, 1999) "Interleukin 2 Receptor Signaling Regulates the Perforin Gene through Signal Transducer and Activator of Transcription (Stat)5 Activation of Two Enhancers", Journal of Experimental Medicine, 190 (9):1297-1308.
Zwaagstra et al. (Jul. 2012) "Engineering and Therapeutic Application of Single-chain Bivalent TGF-beta Family Traps", Molecular Cancer Therapeutics, 11(7):1477-1487.
Ng et al. (Oct. 1, 2016) "Stimulation of Natural Killer Cell-Mediated Tumor Immunity by an IL15/TGFβ-Neutralizing Fusion Protein", Cancer Research, 76(19):5683-5695.

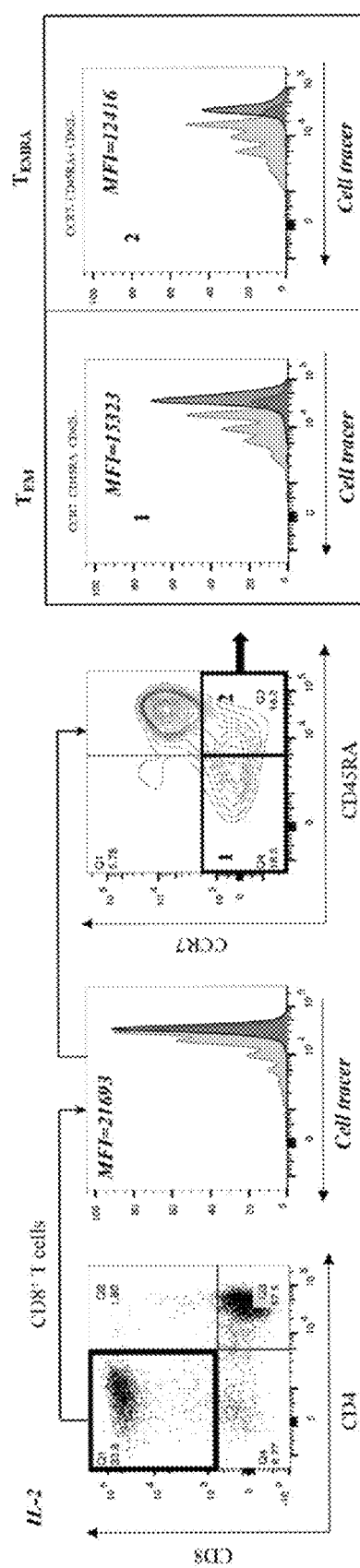
FIG. 6C
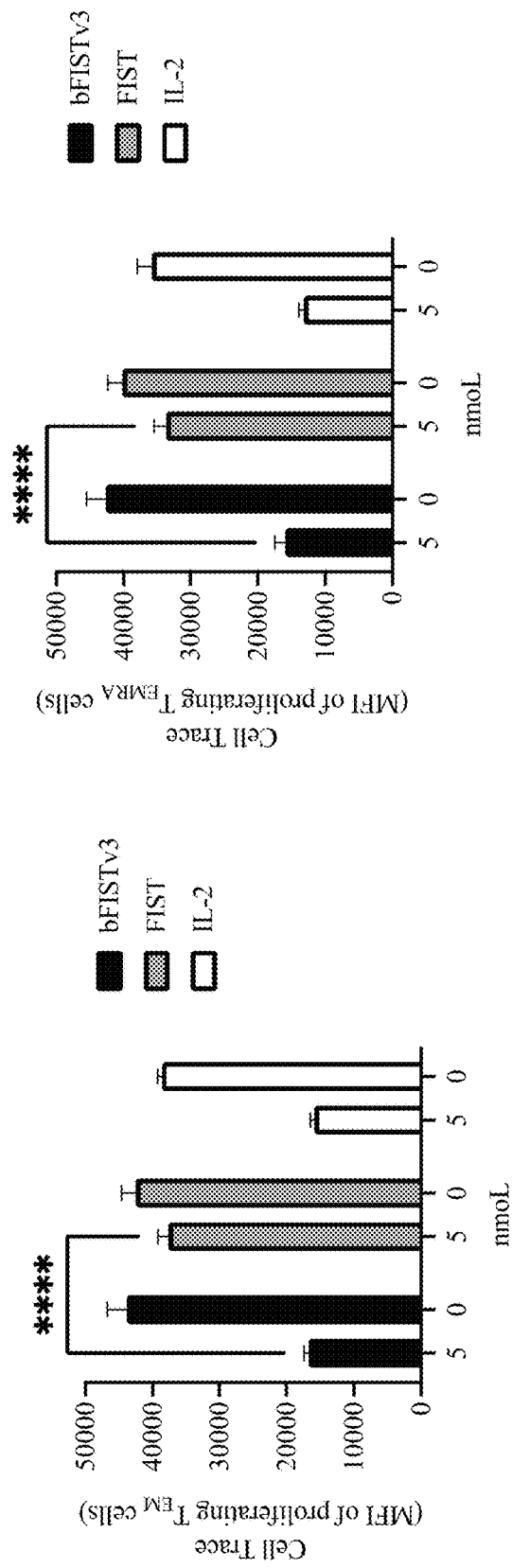
FIG. 6D
FIG. 6E

SEQUENCE LISTING

```
Sequence total quantity: 25
SEQ ID NO: 1                moltype = AA  length = 153
FEATURE                     Location/Qualifiers
source                      1..153
                            mol_type = protein
                            organism = Homo sapiens
SEQUENCE: 1
MYRMQLLSCI ALSLALVTNS APTSSSTKKT QLQLEHLLLD LQMILNGINN YKNPKLTRML   60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                               153

SEQ ID NO: 2                moltype = AA  length = 152
FEATURE                     Location/Qualifiers
source                      1..152
                            mol_type = protein
                            organism = Homo sapiens
SEQUENCE: 2
MYRMQLLSCI ALSLALVTNS APTSSSTKKT QLQLEHLLLD LQMILNGINN YKNPKLTRML   60
TFKFYMPKKA TELKHLQCLE EELKPLEEVL NLAQSKNFHL RPRDLISNIN VIVLELKGSE  120
TTFMCEYADE TATIVEFLNR WITFCQSIIS TL                                152

SEQ ID NO: 3                moltype = AA  length = 152
FEATURE                     Location/Qualifiers
REGION                      1..152
                            note = Description of Artificial Sequence: Synthetic
                             polypeptide
source                      1..152
                            mol_type = protein
                            organism = synthetic construct
SEQUENCE: 3
MYRMQLLSCI ALSLALVTNS APTSSSTKKT QLQLEHLLLD LQMILNGINN YKNPKLTRML   60
TAKFYMPKKA TELKHLQCLE EELKPLEEVL NLAQSKNFHL RPRDLISNIN VIVLELKGSE  120
TTFMCEYADE TATIVEFLNR WITFCQSIIS TL                                152

SEQ ID NO: 4                moltype = AA  length = 135
FEATURE                     Location/Qualifiers
source                      1..135
                            mol_type = protein
                            organism = Homo sapiens
SEQUENCE: 4
MVLGTIDLCS CFSAGLPKTE ANWVNVISDL KKIEDLIQSM HIDATLYTES DVHPSCKVTA   60
MKCFLLELQV ISLESGDASI HDTVENLIIL ANNSLSSNGN VTESGCKECE ELEEKNIKEF  120
LQSFVHIVQM FINTS                                                   135

SEQ ID NO: 5                moltype = AA  length = 125
FEATURE                     Location/Qualifiers
source                      1..125
                            mol_type = protein
                            organism = Homo sapiens
SEQUENCE: 5
CFSAGLPKTE ANWVNVISDL KKIEDLIQSM HIDATLYTES DVHPSCKVTA MKCFLLELQV   60
ISLESGDASI HDTVENLIIL ANNSLSSNGN VTESGCKECE ELEEKNIKEF LQSFVHIVQM  120
FINTS                                                              125

SEQ ID NO: 6                moltype = AA  length = 567
FEATURE                     Location/Qualifiers
source                      1..567
                            mol_type = protein
                            organism = Homo sapiens
SEQUENCE: 6
MGRGLLRGLW PLHIVLWTRI ASTIPPHVQK SVNNDMIVTD NNGAVKFPQL CKFCDVRFST   60
CDNQKSCMSN CSITSICEKP QEVCAVWRK NDENITLETV CHDPKLPYHD FILEDAASPK  120
CIMKEKKKPG ETFFMCSCSS DECNDNIIFS EEYNTSNPDL LLVIFQVTGI SLLPPLGVAI  180
SVIIIFYCYR VNRQQKLSST WETGKTRKLM EFSEHCAIIL EDDRSDISST CANNINHNTE  240
LLPIELDTLV GKGRFAEVYK AKLKQNTSEQ FETVAVKIFP YEEYASWKTE KDIFSDINLK  300
HENILQFLTA EERKTELGKQ YWLITAFHAK GNLQEYLTRH VISWEDLRKL GSSLARGIAH  360
LHSDHTPCGR PKMPIVHRDL KSSNILVKND LTCCLCDFGL SLRLDPTLSV DDLANSGQVG  420
TARYMAPEVL ESRMNLENVE SFKQTDVYSM ALVLWEMTSR CNAVGEVKDY EPPFGSKVRE  480
HPCVESMKDN VLRDRGRPEI PSFWLNHQGI QMVCETLTEC WDHDPEARLT AQCVAERFSE  540
LEHLDRLSGR SCSEEKIPED GSLNTTK                                     567

SEQ ID NO: 7                moltype = AA  length = 592
FEATURE                     Location/Qualifiers
source                      1..592
                            mol_type = protein
                            organism = Homo sapiens
SEQUENCE: 7
MGRGLLRGLW PLHIVLWTRI ASTIPPHVQK SDVEMEAQKD EIICPSCNRT AHPLRHINND   60
```

```
MIVTDNNGAV KFPQLCKFCD VRFSTCDNQK SCMSNCSITS ICEKPQEVCV AVWRKNDENI    120
TLETVCHDPK LPYHDFILED AASPKCIMKE KKKPGETFFM CSCSSDECND NIIFSEEYNT    180
SNPDLLLVIF QVTGISLLPP LGVAISVIII FYCYRVNRQQ KLSSTWETGK TRKLMEFSEH    240
CAIILEDDRS DISSTCANNI NHNTELLPIE LDTLVGKGRF AEVYKAKLKQ NTSEQFETVA    300
VKIFPYEEYA SWKTEKDIFS DINLKHENIL QFLTAEERKT ELGKQYWLIT APHAKGNLQE    360
YLTRHVISWE DLRKLGSSLA RGIAHLHSDH TPCGRPKMPI VHRDLKSSNI LVKNDLTCCL    420
CDFGLSLRLD PTLSVDDLAN SGQVGTARYM APEVLESRMN LENVESFKQT DVYSMALVLW    480
EMTSRCNAVG EVKDYEPPFG SKVREHPCVE SMKDNVLRDR GRPEIPSFWL NHQGIQMVCE    540
TLTECWDHDP EARLTAQCVA ERFSELEHLD RLSGRSCSEE KIPEDGSLNT TK            592

SEQ ID NO: 8            moltype = AA   length = 136
FEATURE                 Location/Qualifiers
REGION                  1..136
                        note = Description of Artificial Sequence: Synthetic
                         polypeptide
source                  1..136
                        mol_type = protein
                        organism = synthetic construct
SEQUENCE: 8
IPPHVQKSVN NDMIVTDNNG AVKLPQLCKF CDVRFSTCDN QKSCMSNCSI TSICEKPHEV    60
CVAVWRKNDE NITLETVCHD PKLTYHGFTL EDAASPKCVM KEKKKPGETF FMCSCSADEC    120
NDNIIFSEDY NTSNPD                                                   136

SEQ ID NO: 9            moltype = AA   length = 161
FEATURE                 Location/Qualifiers
REGION                  1..161
                        note = Description of Artificial Sequence: Synthetic
                         polypeptide
source                  1..161
                        mol_type = protein
                        organism = synthetic construct
SEQUENCE: 9
IPPHVQKSDV EMEAQKGEMI CVTCNRTAHP LKHVNNDMIV TDNNGAVKLP QLCKFCDVRF    60
STCDNQKSCM SNCSITSICE KPQEVCVAVW RKNDENITLE TVCHDPKLTY HGFTLEDAAS    120
PKCVMKEKKK PGETFFMCSC SSDECNDNII FSEDYNTSNP D                       161

SEQ ID NO: 10           moltype = AA   length = 409
FEATURE                 Location/Qualifiers
REGION                  1..409
                        note = Description of Artificial Sequence: Synthetic
                         polypeptide
source                  1..409
                        mol_type = protein
                        organism = synthetic construct
SEQUENCE: 10
MYRMQLLSCI ALSLALVTNS APTSSSTKKT QLQLEHLLLD LQMILNGINN YKNPKLTRML    60
TAKFYMPKKA TELKHLQCLE EELKPLEEVL NLAQSKNFHL RPRDLISNIN VIVLELKGSE    120
TTFMCEYADE TATIVEFLNR WITFCQSIIS TLQKSVNNDM IVTDNNGAVK LPQLCKFCDV    180
RFSTCDNQKS CMSNCSITSI CEKPHEVCVA VWRKNDENIT LETVCHDPKL TYHGFTLEDA    240
ASPKCVMKEK KKPGETFFMC SCSADECNDN IIFIPPHVQK SVNNDMIVTD NNGAVKLPQL    300
CKFCDVRFST CDNQKSCMSN CSITSICEKP HEVCVAVWRK NDENITLETV CHDPKLTYHG    360
FTLEDAASPK CVMKEKKKPG ETFFMCSCSA DECNDNIIFS EDYNTSNPD                409

SEQ ID NO: 11           moltype = AA   length = 424
FEATURE                 Location/Qualifiers
REGION                  1..424
                        note = Description of Artificial Sequence: Synthetic
                         polypeptide
source                  1..424
                        mol_type = protein
                        organism = synthetic construct
SEQUENCE: 11
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE    120
TTFMCEYADE TATIVEFLNR WITFCQSIIS TLIPPHVQKS VNNDMIVTDN GAVKLPQLC    180
KFCDVRFSTC DNQKSCMSNC SITSICEKPH EVCVAVWRKN DENITLETVC HDPKLTYHGF    240
TLEDAASPKC VMKEKKKPGE TFFMCSCSAD ECNDNIIFSE DYNTSNPDIP PHVQKSVNND    300
MIVTDNNGAV KLPQLCKFCD VRFSTCDNQK SCMSNCSITS ICEKPHEVCV AVWRKNDENI    360
TLETVCHDPK LTYHGFTLED AASPKCVMKE KKKPGETFFM CSCSADECND NIIFSEDYNT    420
SNPD                                                                424

SEQ ID NO: 12           moltype = AA   length = 434
FEATURE                 Location/Qualifiers
REGION                  1..434
                        note = Description of Artificial Sequence: Synthetic
                         polypeptide
source                  1..434
                        mol_type = protein
                        organism = synthetic construct
```

```
SEQUENCE: 12
MYRMQLLSCI ALSLALVTNS APTSSSTKKT QLQLEHLLLD LQMILNGINN YKNPKLTRML    60
TAKFYMPKKA TELKHLQCLE EELKPLEEVL NLAQSKNFHL RPRDLISNIN VIVLELKGSE   120
TTFMCEYADE TATIVEFLNR WITFCQSIIS TLQKSDVEME AQKGEMICVT CNRTAHPLKH   180
VNNDMIVTDN NGAVKLPQLC KFCDVRFSTC DNQKSCMSNC SITSICEKPQ EVCVAVWRKN   240
DENITLETVC HDPKLTYHGF TLEDAASPKC VMKEKKKPGE TFFMCSCSSD ECNDNIIFIP   300
PHVQKSVNND MIVTDNNGAV KLPQLCKFCD VRFSTCDNQK SCMSNCSITS ICEKPHEVCV   360
AVWRKNDENI TLETVCHDPK LTYHGFTLED AASPKCVMKE KKKPGETFFM CSCSADECND   420
NIIFSEDYNT SNPD                                                    434

SEQ ID NO: 13           moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 13
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLQIPPHVKS DVEMEAQKGE MICVTCNRTA   180
HPLKHVNNDM IVTDNNGAVK LPQLCKFCDV RFSTCDNQKS CMSNCSITSI CEKPQEVCVA   240
VWRKNDENIT LETVCHDPKL TYHGFTLEDA ASPKCVMKEK KKPGETFFMC SCSSDECNDN   300
IIFSEDYNTS NPDIPPHVQK SVNNDMIVTD NNGAVKLPQL CKFCDVRFST CDNQKSCMSN   360
CSITSICEKP HEVCVAVWRK NDENITLETV CHDPKLTYHG FTLEDAASPK CVMKEKKKPG   420
ETFFMCSCSA DECNDNIIFS EDYNTSNPD                                    449

SEQ ID NO: 14           moltype = AA  length = 434
FEATURE                 Location/Qualifiers
REGION                  1..434
                        note = Description of Artificial Sequence: Synthetic
                         polypeptide
source                  1..434
                        mol_type = protein
                        organism = synthetic construct
SEQUENCE: 14
MYRMQLLSCI ALSLALVTNS APTSSSTKKT QLQLEHLLLD LQMILNGINN YKNPKLTRML    60
TAKFYMPKKA TELKHLQCLE EELKPLEEVL NLAQSKNFHL RPRDLISNIN VIVLELKGSE   120
TTFMCEYADE TATIVEFLNR WITFCQSIIS TLQKSVNNDM IVTDNNGAVK LPQLCKFCDV   180
RFSTCDNQKS CMSNCSITSI CEKPHEVCVA VWRKNDENIT LETVCHDPKL TYHGFTLEDA   240
ASPKCVMKEK KKPGETFFMC SCSADECNDN IIFIPPHVQK SDVEMEAQKG EMICVTCNRT   300
AHPLKHVNND MIVTDNNGAV KLPQLCKFCD VRFSTCDNQK SCMSNCSITS ICEKPQEVCV   360
AVWRKNDENI TLETVCHDPK LTYHGFTLED AASPKCVMKE KKKPGETFFM CSCSSDECND   420
NIIFSEDYNT SNPD                                                    434

SEQ ID NO: 15           moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 15
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLIPPHVQKS VNNDMIVTDN NGAVKLPQLC   180
KFCDVRFSTC DNQKSCMSNC SITSICEKPH EVCVAVWRKN DENITLETVC HDPKLTYHGF   240
TLEDAASPKC VMKEKKKPGE TFFMCSCSAD ECNDNIIFSE DYNTSNPDIP PHVQKSDVEM   300
EAQKGEMICV TCNRTAHPLK HVNNDMIVTD NNGAVKLPQL CKFCDVRFST CDNQKSCMSN   360
CSITSICEKP QEVCVAVWRK NDENITLETV CHDPKLTYHG FTLEDAASPK CVMKEKKKPG   420
ETFFMCSCSS DECNDNIIFS EDYNTSNPD                                    449

SEQ ID NO: 16           moltype = AA  length = 458
FEATURE                 Location/Qualifiers
REGION                  1..458
                        note = Description of Artificial Sequence: Synthetic
                         polypeptide
source                  1..458
                        mol_type = protein
                        organism = synthetic construct
SEQUENCE: 16
MYRMQLLSCI ALSLALVTNS APTSSSTKKT QLQLEHLLLD LQMILNGINN YKNPKLTRML    60
TAKFYMPKKA TELKHLQCLE EELKPLEEVL NLAQSKNFHL RPRDLISNIN VIVLELKGSE   120
TTFMCEYADE TATIVEFLNR WITFCQSIIS TLQKSDVEME AQKGEMICVT CNRTAHPLKH   180
VNNDMIVTDN NGAVKLPQLC KFCDVRFSTC DNQKSCMSNC SITSICEKPQ EVCVAVWRKN   240
DENITLETVC HDPKLTYHGF TLEDAASPKC VMKEKKKPGE TFFMCSCSSD ECNDNIIFIP   300
PHVKSDVEME AQKGEMICVT CNRTAHPLKH VNNDMIVTDN NGAVKLPQLC KFCDVRFSTC   360
```

```
DNQKSCMSNC SITSICEKPQ EVCVAVWRKN DENITLETVC HDPKLTYHGF TLEDAASPKC  420
VMKEKKKPGE TFFMCSCSSD ECNDNIIFSE DYNTSNPD                         458

SEQ ID NO: 17             moltype = AA  length = 473
FEATURE                   Location/Qualifiers
REGION                    1..473
                          note = Description of Artificial Sequence: Synthetic
                          polypeptide
source                    1..473
                          mol_type = protein
                          organism = synthetic construct
SEQUENCE: 17
MYRMQLLSCI ALSLALVTNS APTSSSTKKT QLQLEHLLLD LQMILNGINN YKNPKLTRML   60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLQIPPHVKS DVEMEAQKGE MICVTCNRTA  180
HPLKHVNNDM IVTDNNGAVK LPQLCKFCDV RFSTCDNQKS CMSNCSITSI CEKPQEVCVA  240
VWRKNDENIT LETVCHDPKL TYHGFTLEDA ASPKCVMKEK KKPGETFFMC SCSSDECNDN  300
IIFSEDYNTS NPDIPPHVKS DVEMEAQKGE MICVTCNRTA HPLKHVNNDM IVTDNNGAVK  360
LPQLCKFCDV RFSTCDNQKS CMSNCSITSI CEKPQEVCVA VWRKNDENIT LETVCHDPKL  420
TYHGFTLEDA ASPKCVMKEK KKPGETFFMC SCSSDECNDN IIFSEDYNTS NPD         473

SEQ ID NO: 18             moltype = AA  length = 664
FEATURE                   Location/Qualifiers
REGION                    1..664
                          note = Description of Artificial Sequence: Synthetic
                          polypeptide
source                    1..664
                          mol_type = protein
                          organism = synthetic construct
SEQUENCE: 18
MYRMQLLSCI ALSLALVTNS ISAMVRSVEC PPCPAPPVAG PSVFLFPPKP KDTLMISRTP   60
EVTCVVVDVS HEDPEVKFNW YVDGVEVHNA KTKPREEQYN STYRVVSVLT VLHQDWLNGK  120
EYKCKVSNKG LPSSIEKTIS KAKGQPREPQ VYTLPPSREE MTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK APTSSSTKKT QLQLEHLLLD LQMILNGINN YKNPKLTRML TAKFYMPKKA  300
TELKHLQCLE EELKPLEEVL NLAQSKNFHL RPRDLISNIN VIVLELKGSE TTFMCEYADE  360
TATIVEFLNR WITFCQSIIS TLQKSDVEME AQKGEMICVT CNRTAHPLKH VNNDMIVTDN  420
NGAVKLPQLC KFCDVRFSTC DNQKSCMSNC SITSICEKPQ EVCVAVWRKN DENITLETVC  480
HDPKLTYHGF TLEDAASPKC VMKEKKKPGE TFFMCSCSSD ECNDNIIFIP PHVQKSVNND  540
MIVTDNNGAV KLPQLCKFCD VRFSTCDNQK SCMSNCSITS ICEKPHEVCV AVWRKNDENI  600
TLETVCHDPK LTYHGFTLED AASPKCVMKE KKKPGETFFM CSCSADECND NIIFSEDYNT  660
SNPD                                                               664

SEQ ID NO: 19             moltype = AA  length = 639
FEATURE                   Location/Qualifiers
REGION                    1..639
                          note = Description of Artificial Sequence: Synthetic
                          polypeptide
source                    1..639
                          mol_type = protein
                          organism = synthetic construct
SEQUENCE: 19
MYRMQLLSCI ALSLALVTNS ISAMVRSVEC PPCPAPPVAG PSVFLFPPKP KDTLMISRTP   60
EVTCVVVDVS HEDPEVKFNW YVDGVEVHNA KTKPREEQYN STYRVVSVLT VLHQDWLNGK  120
EYKCKVSNKG LPSSIEKTIS KAKGQPREPQ VYTLPPSREE MTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK APTSSSTKKT QLQLEHLLLD LQMILNGINN YKNPKLTRML TAKFYMPKKA  300
TELKHLQCLE EELKPLEEVL NLAQSKNFHL RPRDLISNIN VIVLELKGSE TTFMCEYADE  360
TATIVEFLNR WITFCQSIIS TLQKSVNNDM IVTDNNGAVK LPQLCKFCDV RFSTCDNQKS  420
CMSNCSITSI CEKPHEVCVA VWRKNDENIT LETVCHDPKL TYHGFTLEDA ASPKCVMKEK  480
KKPGETFFMC SCSADECNDN IIFIPPHVQK SVNNDMIVTD NNGAVKLPQL CKFCDVRFST  540
CDNQKSCMSN CSITSICEKP HEVCAVWRK NDENITLETV CHDPKLTYHG FTLEDAASPK  600
CVMKEKKKPG ETFFMCSCSA DECNDNIIFS EDYNTSNPD                         639

SEQ ID NO: 20             moltype = AA  length = 419
FEATURE                   Location/Qualifiers
REGION                    1..419
                          note = Description of Artificial Sequence: Synthetic
                          polypeptide
source                    1..419
                          mol_type = protein
                          organism = synthetic construct
SEQUENCE: 20
MYRMQLLSCI ALSLALVTNS IPPHVQKSVN NDMIVTDNNG AVKLPQLCKF CDVRFSTCDN   60
QKSCMSNCSI TSICEKPHEV CVAVWRKNDE NITLETVCHD PKLTYHGFTL EDAASPKCVM  120
KEKKKPGETF FMCSCSADEC NDNIIFSEDY NTSNPDAPTS SSTKKTQLQL EHLLLDLQMI  180
LNGINNYKNP KLTRMLTAKF YMPKKATELK HLQCLEEELK PLEEVLNLAQ SKNFHLRPRD  240
LISNINIVVL ELKGSETTFM CEYADETATI VEFLNRWITF CQSIISTLQK SVNNDMIVTD  300
NNGAVKLPQL CKFCDVRFST CDNQKSCMSN CSITSICEKP HEVCAVWRK NDENITLETV  360
```

```
CHDPKLTYHG FTLEDAASPK CVMKEKKKPG ETFFMCSCSA DECNDNIIFS EDYNTSNPD      419

SEQ ID NO: 21           moltype = AA   length = 444
FEATURE                 Location/Qualifiers
REGION                  1..444
                        note = Description of Artificial Sequence: Synthetic
                         polypeptide
source                  1..444
                        mol_type = protein
                        organism = synthetic construct
SEQUENCE: 21
MYRMQLLSCI ALSLALVTNS IPPHVQKSVN NDMIVTDNNG AVKLPQLCKF CDVRFSTCDN      60
QKSCMSNCSI TSICEKPHEV CVAVWRKNDE NITLETVCHD PKLTYHGFTL EDAASPKCVM     120
KEKKKPGETF FMCSCSADEC NDNIIFSEDY NTSNPDAPTS SSTKKTQLQL EHLLLDLQMI     180
LNGINNYKNP KLTRMLTAKF YMPKKATELK HLQCLEEELK PLEEVLNLAQ SKNFHLRPRD     240
LISNINVIVL ELKGSETTFM CEYADETATI VEFLNRWITF CQSIISTLQK SDVEMEAQKG     300
EMICVTCNRT AHPLKHVNND MIVTDNNGAV KLPQLCKFCD VRFSTCDNQK SCMSNCSITS     360
ICEKPQEVCV AVWRKNDENI TLETVCHDPK LTYHGFTLED AASPKCVMKE KKKPGETFFM     420
CSCSSDECND NIIFSEDYNT SNPD                                           444

SEQ ID NO: 22           moltype = AA   length = 468
FEATURE                 Location/Qualifiers
REGION                  1..468
                        note = Description of Artificial Sequence: Synthetic
                         polypeptide
source                  1..468
                        mol_type = protein
                        organism = synthetic construct
SEQUENCE: 22
MYRMQLLSCI ALSLALVTNS IPPHVKSDVE MEAQKGEMIC VTCNRTAHPL KHVNNDMIVT      60
DNNGAVKLPQ LCKFCDVRFS TCDNQKSCMS NCSITSICEK PQEVCVAVWR KNDENITLET    120
VCHDPKLTYH GFTLEDAASP KCVMKEKKKP GETFFMCSCS SDECNDNIIF SEDYNTSNPD    180
APTSSSTKKT QLQLEHLLLD LQMILNGINN YKNPKLTRML TAKFYMPKKA TELKHLQCLE    240
EELKPLEEVL NLAQSKNFHL RPRDLISNIN VIVLELKGSE TTFMCEYADE TATIVEFLNR    300
WITFCQSIIS TLQKSDVEME AQKGEMICVT CNRTAHPLKH VNNDMIVTDN NGAVKLPQLC    360
KFCDVRFSTC DNQKSCMSNC SITSICEKPQ EVCVAVWRKN DENITLETVC HDPKLTYHGF    420
TLEDAASPKC VMKEKKKPGE TFFMCSCSSD ECNDNIIFSE DYNTSNPD                 468

SEQ ID NO: 23           moltype = AA   length = 308
FEATURE                 Location/Qualifiers
REGION                  1..308
                        note = Description of Artificial Sequence: Synthetic
                         polypeptide
source                  1..308
                        mol_type = protein
                        organism = synthetic construct
SEQUENCE: 23
MYRMQLLSCI ALSLALVTNS APTSSSTKKT QLQLEHLLLD LQMILNGINN YKNPKLTRML      60
TFKFYMPKKA TELKHLQCLE EELKPLEEVL NLAQSKNFHL RPRDLISNIN VIVLELKGSE    120
TTFMCEYADE TATIVEFLNR WITFCQSIIS TLQKSDVEME AQKGEMICVT CNRTAHPLKH    180
VNNDMIVTDN NGAVKLPQLC KFCDVRFSTC DNQKSCMSNC SITSICEKPQ EVCVAVWRKN    240
DENITLETVC HDPKLTYHGF TLEDAASPKC VMKEKKKPGE TFFMCSCSSD ECNDNIIFSE    300
DYNTSNPD                                                             308

SEQ ID NO: 24           moltype = AA   length = 308
FEATURE                 Location/Qualifiers
REGION                  1..308
                        note = Description of Artificial Sequence: Synthetic
                         polypeptide
source                  1..308
                        mol_type = protein
                        organism = synthetic construct
SEQUENCE: 24
MYRMQLLSCI ALSLALVTNS APTSSSTKKT QLQLEHLLLD LQMILNGINN YKNPKLTRML      60
TAKFYMPKKA TELKHLQCLE EELKPLEEVL NLAQSKNFHL RPRDLISNIN VIVLELKGSE    120
TTFMCEYADE TATIVEFLNR WITFCQSIIS TLQKSDVEME AQKGEMICVT CNRTAHPLKH    180
VNNDMIVTDN NGAVKLPQLC KFCDVRFSTC DNQKSCMSNC SITSICEKPQ EVCVAVWRKN    240
DENITLETVC HDPKLTYHGF TLEDAASPKC VMKEKKKPGE TFFMCSCSSD ECNDNIIFSE    300
DYNTSNPD                                                             308

SEQ ID NO: 25           moltype = AA   length = 283
FEATURE                 Location/Qualifiers
REGION                  1..283
                        note = Description of Artificial Sequence: Synthetic
                         polypeptide
source                  1..283
                        mol_type = protein
                        organism = synthetic construct
SEQUENCE: 25
```

```
MYRMQLLSCI ALSLALVTNS APTSSSTKKT QLQLEHLLLD LQMILNGINN YKNPKLTRML    60
TAKFYMPKKA TELKHLQCLE EELKPLEEVL NLAQSKNFHL RPRDLISNIN VIVLELKGSE   120
TTFMCEYADE TATIVEFLNR WITFCQSIIS TLQKSVNNDM IVTDNNGAVK LPQLCKFCDV   180
RFSTCDNQKS CMSNCSITSI CEKPHEVCVA VWRKNDENIT LETVCHDPKL TYHGFTLEDA   240
ASPKCVMKEK KKPGETFFMC SCSADECNDN IIFSEDYNTS NPD                    283
```

METHOD OF REDUCING OR TREATING FIBROSIS BY ADMINISTERING AN INTERLEUKIN-2/TGF-BETA RECEPTOR FUSION POLYPEPTIDE

CROSS REFERENCE TO RELATED APPLICATIONS

This application is a divisional of U.S. application Ser. No. 17/673,691, filed on Feb. 16, 2022, now U.S. Pat. No. 11,672,844, issued on Jun. 13, 2023, and claims priority to and benefit of U.S. Provisional Application No. 63/150,450 filed on Feb. 17, 2021, the contents of each of which are incorporated herein by reference in their entireties.

INCORPORATION-BY-REFERENCE OF SEQUENCE LISTING

The instant application contains a Sequence Listing which has been submitted electronically in ASCII format and is hereby incorporated by reference in its entirety. Said ASCII copy, created on Apr. 28, 2023, is named 062676-502D01US_SeqList_ST26 and is 39,673 bytes in size.

BACKGROUND

Transforming growth factor-β (TGF-β) family or proteins are pleiotropic cytokines that modulate an immune response. TGF-β proteins were originally named for their ability to transform normal fibroblasts to cells capable of anchorage-independent growth. Produced primarily by hematopoietic and tumor cells, TGF-β proteins can regulate (e.g., stimulate or inhibit) the growth and differentiation of cells from a diversity of normal or neoplastic tissue origins. Notably, TGF-β proteins are known to be involved in many proliferative and non-proliferative cellular processes such as, e.g., cell proliferation and differentiation, embryonic development, extracellular matrix formation, bone development, wound healing, hematopoiesis, and immune and inflammatory responses. Increased levels of TGF-β expression and activity are involved in a large number of pathologic conditions, including, but not limited to, aberrant immunosuppression, wherein members of the TGF-β protein family are known to have a number of biological activities related to reducing the efficacy of an immune response.

Interleukins (e.g., IL-2 or IL-15) are potent cytokines that act on the immune system to generate primarily a cell-mediated immune response. For example, IL-2 is locally produced by immune cells at high concentrations near the site of an antigen to supply the necessary costimulatory signals for generating an immune system response to the antigen. IL-2 is therefore an immune-activating molecule and may hold the potential to promote immunotherapeutic responses in treating pathogenic infections (e.g., viral or bacterial infections). For example, in addition to stimulating T cells, IL-2 has also been shown to stimulate lymphocytes (e.g., T cells, B cells, NK cells, NKT cells). However, high doses of IL-2 based therapies have previously been associated with toxicity observed with IL-2 systemic administration. Such deleterious effects present hurdles for the successful utilization of IL-2 as an effective therapeutic.

SUMMARY

Provided herein are fusion proteins that function to activate an immune response and/or inhibit immunosuppressive signaling. This is generally achieved with fusion proteins that comprise an interleukin polypeptide fused (e.g., linked) to two or more polypeptides that inhibit TGFβ activity (e.g., two or more polypeptides that bind to a TGFβ protein). The compositions provided herein are also useful for the inhibition of immunosuppression and/or for activating immune cells. Accordingly, also disclosed herein are methods of inhibiting and/or treating a pathogenic infection (e.g., an intracellular pathogen infection) using the fusion proteins disclosed herein.

Provided are compositions for use in and methods of treating or ameliorating a pathogenic infection in a subject, the method comprising administering to the subject a therapeutically effective amount of a fusion polypeptide comprising: an interleukin (IL) polypeptide; a first TGFβ superfamily receptor polypeptide; and a second TGFβ superfamily receptor polypeptide, thereby treating or ameliorating the pathogenic infection in the subject. Further provided are compositions for use in and methods of treating a pathogenic infection in a subject, the method comprising administering to the subject a therapeutically effective amount of a fusion polypeptide comprising: an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, thereby treating the pathogenic infection in the subject.

Additionally provided are methods of treating or ameliorating fibrosis associated with or resulting from a pathogenic infection (e.g., an intracellular pathogen infection) in a subject, comprising administering a fusion polypeptide comprising: an interleukin (IL) polypeptide; a first TGFβ superfamily receptor polypeptide; and a second TGFβ superfamily receptor polypeptide. Also provided are methods of reducing or inhibiting fibrosis associated with or resulting from a pathogenic infection (e.g., an intracellular pathogen infection) in a subject, comprising administering a fusion polypeptide comprising: an interleukin (IL) polypeptide; a first TGFβ superfamily receptor polypeptide; and a second TGFβ superfamily receptor polypeptide.

In some embodiments, provided is a method of any of the preceding embodiments, wherein the IL polypeptide comprises an IL-2 polypeptide or an IL-15 polypeptide. In some embodiments, provided is a method of any of the preceding embodiments, wherein the IL polypeptide comprises an IL-2 polypeptide. In some embodiments, provided is a method of any of the preceding embodiments, wherein the IL-2 polypeptide comprises SEQ ID NO: 2. In some embodiments, provided is a method of any of the preceding embodiments, wherein the IL-2 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 2. In some embodiments, provided is a method of any of the preceding embodiments, wherein the IL-2 polypeptide consists of SEQ ID NO: 2.

In some embodiments, provided is a method of any of the preceding embodiments, wherein the IL polypeptide comprises an IL-15 polypeptide. In some embodiments, provided is a method of any of the preceding embodiments, wherein the IL-15 polypeptide comprises SEQ ID NO: 4.

In some embodiments, provided is a method of any of the preceding embodiments, wherein the IL-15 polypeptide comprises an amino acid sequence having greater than about 80%, greater than about 85%, greater than about 90%, greater than about 95% greater than about 96%, greater than about 97%, greater than about 98%, or greater than about 99% sequence identity to SEQ ID NO: 5. In some embodiments, provided is a method of any of the preceding embodiments, wherein the IL-15 polypeptide consists of SEQ ID NO: 5.

In some embodiments, provided is a method of any of the preceding embodiments, wherein the first TGFβ superfamily receptor polypeptide, the second TGFβ superfamily receptor polypeptide, or both, comprises an activin receptor polypeptide or fragment thereof, a bone morphogenetic protein (BMP) receptor polypeptide or fragment thereof, a glial cell-derived neurotrophic factor (GDNF) receptor polypeptide or fragment thereof, or a TGFβ receptor II polypeptide or fragment thereof.

In some embodiments, provided is a method of any of the preceding embodiments, wherein the first TGFβ superfamily receptor polypeptide, the second TGFβ superfamily receptor polypeptide, or both, comprises a TGFβ receptor II (TβRII) polypeptide or fragment thereof. In some embodiments, provided is a method of any of the preceding embodiments, wherein the first TGFβ superfamily receptor polypeptide, the second TGFβ superfamily receptor polypeptide, or both, comprises a soluble TGFβ receptor II (TβRII) polypeptide or fragment thereof. In some embodiments, provided is a method of any of the preceding embodiments, wherein the first TGFβ superfamily receptor polypeptide, the second TGFβ superfamily receptor polypeptide, or both, comprises a soluble TGFβ receptor II (TβRII) polypeptide comprising SEQ ID NO: 8, SEQ ID NO: 9, or a combination thereof. In some embodiments, provided is a method of any of the preceding embodiments, wherein the first TGFβ superfamily receptor polypeptide comprises an amino acid sequence of SEQ ID NO: 8 and the second TGFβ superfamily receptor polypeptide comprises a truncation of an amino acid sequence of SEQ ID NO: 9. In some embodiments, provided is a method of any of the preceding embodiments, wherein the soluble TGFβ receptor II polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 8 or 9

In some embodiments, provided is a method of any of the preceding embodiments, wherein the first TGFβ superfamily receptor polypeptide, the second TGFβ superfamily receptor polypeptide, or both, binds a TGF-β1 polypeptide, a TGF-β2 polypeptide, a TGF-β3 polypeptide, a activin βA polypeptide, a activin βB polypeptide, a activin βC polypeptide, a activin βE polypeptide, a bone morphogenic protein (BMP) 2 polypeptide, a BMP 3 polypeptide, a BMP4 polypeptide, a BMP 5 polypeptide, a BMP 6 polypeptide, a BMP 7 polypeptide, a BMP 8 polypeptide, a BMP 9 polypeptide, a BMP 10 polypeptide, a BMP 11 polypeptide, a BMP 12 polypeptide, a BMP 13 polypeptide, a BMP 14 polypeptide, a BMP 15 polypeptide, a growth differentiation factor (GDF) 1 polypeptide, a GDF 3 polypeptide, a GDF 8 polypeptide, a GDF 9 polypeptide, a GDF 15 polypeptide, a Nodal polypeptide, a Inhibin α polypeptide, an anti-Mullerian Hormone polypeptide, a Lefty 1 polypeptide, a Lefty 2 polypeptide, an arteman polypeptide, a Persephin polypeptide, or a Neurturin polypeptide. In some embodiments, provided is a method of any of the preceding embodiments, wherein the first TGFβ superfamily receptor polypeptide, the second TGFβ superfamily receptor polypeptide, or both, binds a TGFβ1 polypeptide, a TGFβ2 polypeptide, a TGFβ3 polypeptide, or any combination thereof. In some embodiments, provided is a method of any of the preceding embodiments, wherein the first TGFβ superfamily receptor polypeptide and the second TGFβ superfamily receptor polypeptide bind a TGFβ1 polypeptide.

In some embodiments, the truncated TGFβ superfamily receptor polypeptide comprises an N terminus truncation, a C terminus truncation, or combination thereof.

In some embodiments, the truncated TGFβ superfamily receptor polypeptide is a truncated soluble TGFβ receptor II (sTβRII) polypeptide. In some embodiments, provided is a method of any of the preceding embodiments, wherein the truncation comprises greater than 2, greater than 5, greater than 7, greater than 10, greater than 15, greater than 20, greater than 25, or greater than 30 amino acids. In some embodiments, provided is a method of any of the preceding embodiments, wherein the IL polypeptide comprises a truncated IL polypeptide.

In some embodiments, truncated IL polypeptide comprises an N terminus truncation, a C terminus truncation, or combination thereof. In some embodiments, provided is a method of any of the preceding embodiments, wherein the truncated IL polypeptide comprises a truncated IL-2 polypeptide or a truncated IL-15 polypeptide.

In some embodiments, provided is a method of any of the preceding embodiments, further comprising a linker polypeptide or a linker molecule attaching the first TGFβ superfamily receptor polypeptide and the second TGFβ superfamily receptor polypeptide. In some embodiments, provided is a method of any of the preceding embodiments, further comprising a linker polypeptide fusing the IL polypeptide and the first TGFβ superfamily receptor polypeptide. In some embodiments, provided is a method of any of the preceding embodiments, further comprising a pharmacokinetic (PK) modulator. In some embodiments, provided is a method of any of the preceding embodiments, wherein the pharmacokinetic modulator comprises an immunoglobulin constant (Fc) region polypeptide. In some embodiments, provided is a method of any of the preceding embodiments, wherein the immunoglobulin Fc region polypeptide is a human immunoglobulin Fc region polypeptide. In some embodiments, provided is a method of any of the preceding embodiments, wherein the immunoglobulin Fc region is an IgG Fc region. In some embodiments, provided is a method of any of the preceding embodiments, wherein the IgG Fc region is an IgG1, IgG2, IgG3, or IgG4 Fc region. In some embodiments, provided is a method of any of the preceding embodiments, wherein the PK modulator comprises an albumin polypeptide. In some embodiments, provided is a method of any of the preceding embodiments, wherein the albumin polypeptide is a human albumin polypeptide.

In some embodiments, provided is a method of any of the preceding embodiments, wherein the fusion polypeptide comprises an amino acid sequence having at least about 80%, at least about 85%, at least about 90%, at least about 95%, at least about 96%, at least about 97%, at least about 98%, or at least about 99% sequence identity to any one of SEQ ID NOs: 10-25. In some embodiments, provided is a method of any of the preceding embodiments, wherein the fusion polypeptide comprises an amino acid sequence of SEQ ID NO: 10. In some embodiments, provided is a method of any of the preceding embodiments, wherein the fusion polypeptide comprises an amino acid sequence of SEQ ID NO: 11. In some embodiments, provided is a method of any of the preceding embodiments, wherein the fusion polypeptide comprises an amino acid sequence of SEQ ID NO: 12. In some embodiments, provided is a method of any of the preceding embodiments, wherein the fusion polypeptide comprises an amino acid sequence of SEQ ID NO: 13. In some embodiments, provided is a method of any of the preceding embodiments, wherein the fusion polypeptide comprises an amino acid sequence of SEQ ID NO: 14.

In some embodiments, the fusion polypeptide comprises an amino acid sequence of SEQ ID NO: 15. In some embodiments, provided is a method of any of the preceding embodiments, the fusion polypeptide comprises an amino acid sequence of SEQ ID NO: 16.

In some embodiments, the fusion polypeptide comprises an amino acid sequence of SEQ ID NO: 17. In some embodiments, provided is a method of any of the preceding embodiments, wherein the fusion polypeptide comprises an amino acid sequence of SEQ ID NO: 18. In some embodiments, provided is a method of any of the preceding embodiments, wherein the fusion polypeptide comprises an amino acid sequence of SEQ ID NO: 19.

In some embodiments, the fusion polypeptide comprises an amino acid sequence of SEQ ID NO: 20.

In some embodiments, the fusion polypeptide comprises an amino acid sequence of SEQ ID NO: 21. In some embodiments, the fusion polypeptide comprises an amino acid sequence of SEQ ID NO: 22. In some embodiments, the fusion polypeptide comprises an amino acid sequence of SEQ ID NO: 23. In some embodiments, the fusion polypeptide comprises an amino acid sequence of SEQ ID NO: 24. In some embodiments, the fusion polypeptide comprises an amino acid sequence of SEQ ID NO: 25. In some embodiments, provided is a method of any of the preceding embodiments, wherein the fusion polypeptide consists of any one of SEQ ID NOs: 10-25.

In some embodiments, provided is a method of any of the preceding embodiments, wherein the fusion polypeptide activates target cells expressing an IL-2 receptor or an IL-15 receptor. In some embodiments, provided is a method of any of the preceding embodiments, wherein the target cell is an immune cell. In some embodiments, provided is a method of any of the preceding embodiments, wherein the immune cell is a T cell, a natural killer cell, an NKT cell, a B cell, or a gamma delta T cell.

In some embodiments, provided is a method of any of the preceding embodiments, wherein the pathogenic infection comprises an intracellular pathogen. In certain embodiments, the intracellular pathogens comprises viruses and/or bacteria. Examples of intracellular bacteria include *Brucella, Legionella pneumophila, Listeria monocytogenes, Mycobacterium leprae, Mycobacterium tuberculosis, Rickettsia rickettsia, Salmonella typhi, Salmonella typhimurium*, etc.

In some embodiments, provided is a method of any of the preceding embodiments, wherein the intracellular bacterial infection comprises is an infection by the genera *Shigella, Campylobacter, Salmonella, Clostridium, Escherichia, Chlamydiae, Rickettssiaceae, Coxiella, Mycobacteriaceae*, and combinations thereof. In some embodiments, provided is a method of any of the preceding embodiments, wherein the pathogenic infection is a viral infection. In some embodiments, provided is a method of any of the preceding embodiments, wherein the viral infection comprises a virus from the family denoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. In some embodiments, provided is a method of any of the preceding embodiments, wherein the viral infection comprises coronavirus. In some embodiments, provided is a method of any of the preceding embodiments, wherein the viral infection comprises SARS-COV-2. In some embodiments, provided is a method of any of the preceding embodiments, wherein the viral infection comprises influenza.

Also provided are compositions for use in and methods of neutralizing or inhibiting a pathogen in an individual having a pathogenic infection (e.g., an intracellular pathogen infection), the method comprising administering to the individual a therapeutically effective amount of a fusion polypeptide comprising: an interleukin (IL) polypeptide; a first TGFβ superfamily receptor polypeptide; and a second TGFβ superfamily receptor polypeptide; thereby neutralizing or inhibiting the pathogen in the individual. Further provided are compositions for use in and methods of neutralizing or inhibiting a pathogen in an individual having a pathogenic infection, the method comprising administering to the individual a therapeutically effective amount of a fusion polypeptide comprising: an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, thereby neutralizing or inhibiting the pathogen in the individual.

In some embodiments, provided is a method of any of the preceding embodiments, wherein the IL polypeptide comprises an IL-2 polypeptide or an IL-15 polypeptide. In some embodiments, provided is a method of any of the preceding embodiments, wherein the first TGFβ superfamily receptor polypeptide and the second TGFβ superfamily receptor polypeptide bind a TGFβ 1 polypeptide. In some embodiments, provided is a method of any of the preceding embodiments, wherein the fusion polypeptide comprises an amino acid sequence having at least about 80%, at least about 85%, at least about 90%, at least about 95%, at least about 96%, at least about 97%, at least about 98%, at least about 99%, or 100% sequence identity to any one of SEQ ID NOs: 10-25.

In some embodiments, provided is a method of any of the preceding embodiments, wherein inhibiting or reducing the pathogen comprises activating an immune cell in the individual. In some embodiments, provided is a method of any of the preceding embodiments, wherein the immune cell expresses a receptor for IL-2, IL-15, or both. In some embodiments, provided is a method of any of the preceding embodiments, wherein the immune cell comprises a T cell, a natural killer cell, an NKT cell, a B cell, or a gamma delta T cell. In some embodiments, provided is a method of any of the preceding embodiments, wherein the pathogen comprises an intracellular bacterial infection or a viral infection.

In some embodiments, provided is a method of any of the preceding embodiments, wherein the pathogen is a virus. In some embodiments, provided is a method of any of the preceding embodiments, wherein the virus comprises a virus from the family denoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. In some embodiments, provided is a method of any of the preceding embodiments, wherein the virus comprises coronavirus. In some embodiments, provided is a method of any of the preceding embodiments, wherein the virus comprises SARS-COV-2. In some embodiments, provided is a method of any of the preceding embodiments, wherein the virus comprises influenza.

Provided are compositions for use in and a methods of activating an anti-pathogen immune response cell, the method comprising contacting an immune cell with a fusion polypeptide comprising: an interleukin (IL) polypeptide; a first TGFβ superfamily receptor polypeptide; and
a second TGFβ superfamily receptor polypeptide, thereby activating the anti-pathogen immune response cell. Further provided are compositions for use in and methods of activating an anti-pathogen immune response cell, the method comprising contacting an immune cell with a fusion polypeptide comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, thereby activating the anti-pathogen immune response cell.

In some embodiments, provided is a method of any of the preceding embodiments, wherein the IL polypeptide comprises an IL-2 polypeptide or an IL-15 polypeptide. In some embodiments, provided is a method of any of the preceding embodiments, wherein the first TGFβ superfamily receptor polypeptide and the second TGFβ superfamily receptor polypeptide bind a TGFβ 1 polypeptide. In some embodiments, provided is a method of any of the preceding embodiments, wherein the fusion polypeptide comprises an amino acid sequence having at least about 80%, at least about 85%, at least about 90%, at least about 95%, at least about 96%, at least about 97%, at least about 98%, at least about 99%, or 100% sequence identity to any one of SEQ ID NOs: 10-25. In some embodiments, provided is a method of any of the preceding embodiments, wherein the immune cell is in an individual. In some embodiments, provided is a method of any of the preceding embodiments, wherein the immune cell expresses IL-2, IL-15, or both. In some embodiments, provided is a method of any of the preceding embodiments, wherein the immune cell comprises a T cell, a natural killer cell, an NKT cell, a B cell, or a gamma delta T cell.

In some embodiments, provided is a method of any of the preceding embodiments, wherein the pathogen is an intracellular bacterium. In some embodiments, provided is a method of any of the preceding embodiments, wherein the pathogen is a virus. In some embodiments, provided is a method of any of the preceding embodiments, wherein the virus comprises a virus from the family denoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. In some embodiments, provided is a method of any of the preceding embodiments, wherein the virus comprises coronavirus. In some embodiments, provided is a method of any of the preceding embodiments, wherein the virus comprises SARS-COV-2. In some embodiments, provided is a method of any of the preceding embodiments, wherein the virus comprises influenza.

Also provided are uses of a fusion polypeptide comprising an interleukin (IL) polypeptide, a first TGFβ superfamily receptor polypeptide, and a second TGFβ superfamily receptor polypeptide, in a method of neutralizing or inhibiting a virus and/or progression in an individual having a viral infection. Provided are uses of a fusion polypeptide comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, in a method of neutralizing or inhibiting a virus and/or progression in an individual having a viral infection. Further provided are uses of a fusion polypeptide comprising an interleukin (IL) polypeptide, a first TGFβ superfamily receptor polypeptide, and a second TGFβ superfamily receptor polypeptide, in a method of neutralizing or inhibiting an intracellular bacterium and/or progression in an individual having an intracellular bacterial infection.

Further provided are uses of a fusion polypeptide comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, in a method of neutralizing or inhibiting a bacterium and/or progression in an individual having a bacterial infection. Provided are uses of a fusion polypeptide comprising an interleukin (IL) polypeptide, a first TGFβ superfamily receptor polypeptide, and a second TGFβ superfamily receptor polypeptide, in a method of neutralizing or inhibiting an intracellular bacterium and/or progression in an individual having an intracellular bacterial infection. Also provided are uses of a fusion polypeptide comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, in a method of activating an anti-pathogen immune response.

Also provided are methods of reducing or inhibiting fibrosis in an individual, the method comprising administering to the individual a therapeutically effective amount of a fusion polypeptide comprising: (a) an interleukin (IL) polypeptide; (b) a first TGFβ superfamily receptor polypeptide; and (c) a second TGFβ superfamily receptor polypeptide. Further provided are methods of reducing or inhibiting fibrosis resulting from an intracellular pathogen infection in an individual, the method comprising administering to the individual a therapeutically effective amount of a fusion polypeptide comprising: (a) an interleukin (IL) polypeptide; (b) a first TGFβ superfamily receptor polypeptide; and (c) a second TGFβ superfamily receptor polypeptide.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 6A, 6B, 6C, 6D, 6E, and 6F show proliferation of effector memory T cells and terminal differentiated effector memory cells, and the quantification of IFNγ production by stimulated T cells with the bivalent FIST, monovalent FIST, and controls.

DETAILED DESCRIPTION

Figure 1A:
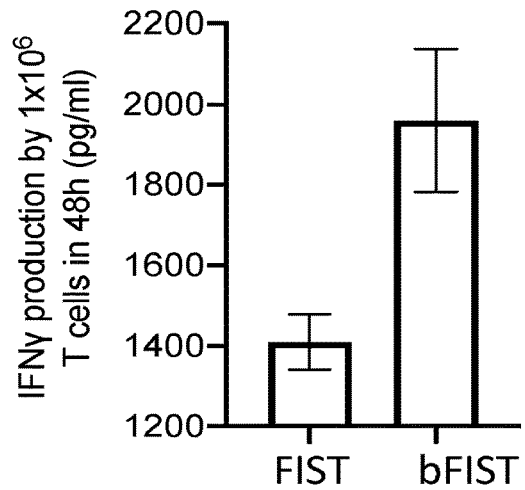
FIGS. 1A and 1B show data depicting the quantification of IFN-gamma production by human T cells previously stimulated by human monovalent FIST (a fusion protein comprising an interleukin-2 (IL-2) polypeptide, a single sTBRII receptor polypeptide) or bivalent FIST (also referred to as bFIST—a fusion polypeptide comprising an interleukin-2 (IL-2) polypeptide, a first sTBRII receptor polypeptide, and a second sTBRII receptor polypeptide), and CXCL10 production by human NK cells stimulated with human FIST (monovalent FIST) or, human bivalent FIST.

Provided herein are multi-functional fusion proteins that are capable of, e.g., activating an immune response, or inhibiting and/or reducing immunosuppressive signaling. In the context of an intracellular pathogenic infection, immune activation is thought to be the physiological function that promotes the recognition and neutralization of a pathogen or pathogen-infected cells. The specific recognition of antigens based on foreignness, molecular weight, complexity, level of expression, and degradability is thought to give rise to the capacities of the immune system to limit pathogen infectivity. In order to activate an immune response and inhibit immunosuppressive signaling, the fusion proteins disclosed herein generally comprise an interleukin polypeptide fused (e.g., linked) to two or more polypeptides that inhibit TGFβ activity (e.g., two or more polypeptides that bind a TGFβ protein). The balance between activating and inhibitory signals is an important factor in maintaining immune homeostasis. In certain instances, immune response to a pathogen encompasses immunostimulatory (e.g., immune activating) signals (e.g., proinflammatory cytokines) that are antagonized by pathogen-induced immunosuppressive signaling molecules (e.g., immunosuppressive cytokines). Among the group of immunosuppressive cytokines thought to be important in driving immunosuppression are members of the TGF superfamily of proteins (e.g., TGFβ).

The TGFβ superfamily includes the TGFβ proteins, Bone Morphogenetic Proteins (BMPs), Growth Differentiation Factors (GDFs), Glial-derived Neurotrophic Factors (GDNFs), Activins, Inhibins, Nodal, Lefty, and Müllerian Inhibiting Substance (MIS). Generally, ligands of the TGFβ superfamily form dimers that bind to heterodimeric receptor complexes consisting of type I and type II receptor subunits with serine/threonine kinase domains.

The TGFβ superfamily of proteins are cytokines thought to be involved in essential cellular functions such as proliferation, differentiation, apoptosis, tissue remodeling, angiogenesis, immune response, and cell adhesion (see, for example, Massagué, J. TGFβ signalling in context. Nat Rev Mol Cell Biol 13, 616-630 (2012)). TGFβ superfamily proteins are also important factors in the pathophysiology of disease states such as chronic inflammatory conditions and fibrosis. The members of this family include the three isoforms of TGFβs: TGFβ1, TGFβ2, and TGFβ3; bone morphogenetic proteins (BMPs); and activins.

The utilization of an interleukin polypeptide (e.g., interleukin-2 or interleukin-15) in the fusion proteins disclosed herein may be useful for activating an immune response in addition to the inhibition of TGFβ. The interleukin family of proteins generally promotes the activation, development, and differentiation of immune cells (e.g., T cells, NK cells, and other lymphocytes), and play essential roles in both innate and adaptive immunity. Accordingly, immune cell activation, development, and differentiation can be achieved by the fusion proteins disclosed herein.

Proinflammatory or immune-stimulating interleukins (e.g., interleukin-2 or interleukin-15) constitute useful adjuvants for activating an immune response. For example, interleukin-2 (IL-2) is a factor for lymphocyte activation and clonal expansion, promoting the activation, development, and differentiation of cytotoxic T cells. IL-2 and IL-15 also stimulate NK cell proliferation and cytotoxicity. However, IL-2 can operate as both an immunostimulatory (e.g., immune-activating) and immunosuppressive agent. As an immunosuppressor, IL-2 maintains peripheral tolerance by inducing the generation of regulatory cells. For these reasons, IL-2 is considered a double-edge sword. The versatility of interleukin function is influenced by the environment and the interaction with signaling agents.

Accordingly, the fusion proteins disclosed herein are multi-functional in that the fusion proteins are useful for immune activation, the inhibition of immunosuppression and tissue fibrosis. As disclosed herein, the activation of an immune response and inhibition of an immunosuppressive response may be, at least in part, achieved by the interleukin polypeptide. In turn, the inhibition or reduction of an immunosuppressive signaling and/or inhibition of tissue fibrosis may be achieved, at least in part, through the use of one or more polypeptides that inhibit activity of TGFβ proteins.

As used herein, the term "fusion protein" generally refers to a protein that includes polypeptide components derived from more than one parental protein or polypeptide. Generally, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

A "domain" of a protein, as used herein, generally is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane, or extracellular domain).

The term "recombinant" indicates that the material (e.g., a nucleic acid or a polypeptide) has been artificially or synthetically (e.g., non-naturally) altered by human intervention. The alteration can be performed on the material within, or removed from, its natural environment or state. For example, a "recombinant nucleic acid" is one that is made by recombining nucleic acids, e.g., during cloning, DNA shuffling, or other well-known molecular biological procedures. A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid.

A "polynucleotide sequence" or "nucleotide sequence" or "nucleic acid sequence," as used interchangeably herein, is a polymer of nucleotides, including an oligonucleotide, a DNA, an RNA, a nucleic acid, or a character string representing a nucleotide polymer, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand.

As used herein, the terms "nucleic acid molecule encoding," "DNA sequence encoding," "nucleic acid sequence encoding" or "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (or protein) chain. The DNA sequence thus codes for the RNA sequence and for the amino acid sequence.

"Expression of a gene" or "expression of a nucleic acid" means transcription of DNA into RNA (optionally including modification of the RNA, e.g., splicing), translation of RNA into a polypeptide (optionally including subsequent post-translational modification of the polypeptide), or both transcription and translation, as indicated by the context.

The term "gene" is used broadly to refer to any nucleic acid associated with a biological function. Genes typically include coding sequences and/or the regulatory sequences required for expression of such coding sequences. The term "gene" applies to a specific genomic or recombinant sequence, as well as to a cDNA or mRNA encoded by that sequence. A "fusion gene" contains a coding region that encodes a transgene. Genes also include non-expressed nucleic acid segments that, for example, form recognition sequences for other proteins. Non-expressed regulatory sequences include transcriptional control elements to which regulatory proteins, such as transcription factors, bind, resulting in transcription of adjacent or nearby sequences.

As used herein the term "coding region" or "coding sequence" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (e.g., TAA, TAG, TGA). Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect, and mammalian cells, and viruses (analogous control elements, e.g., promoters, are also found in prokaryotes). The selection of a particular promoter and enhancer depends on what cell type is to be used to express the protein of interest. Some eukaryotic promoters and enhancers have a broad host range while others are functional in a limited subset of cell types.

The term "expression vector" refers to a recombinant DNA molecule containing a desired coding sequence and appropriate nucleic acid sequences necessary for the expression of the operably linked coding sequence in a particular host cell. Nucleic acid sequences necessary for expression in prokaryotes include a promoter, optionally an operator sequence, a ribosome binding site, and optionally other sequences. Eukaryotic cells are known to utilize promoters, enhancers, and termination and polyadenylation signals. A secretory signal peptide sequence can also, optionally, be encoded by the expression vector, operably linked to the coding sequence for a peptide analog, so that the expressed peptide can be secreted by the recombinant host cell, e.g., for more facile isolation of the peptide from the cell, if desired.

Interleukins

The fusion proteins provided herein generally comprise an interleukin polypeptide fused (e.g., linked) to two or more polypeptides that inhibit TGFβ activity (e.g., two or more polypeptides that bind a TGFβ protein). Interleukins (ILs) are a class of cytokines first thought to be expressed by leukocytes alone but have later been found to be produced by many other body cells. Interleukins are thought to play important roles in, e.g., the activation and differentiation of immune cells, as well as cell proliferation, maturation, migration, and adhesion. The function of interleukins is, therefore, thought to be to modulate growth, differentiation, and activation during inflammatory and immune responses. Accordingly, the interleukin polypeptide of the fusion protein may be useful for the regulation (e.g., activation) of an immune response.

Interleukin-2 (IL-2) is a pleiotropic cytokine that is induced by antigen stimulation and thus plays a significant role in regulating the immune response (see, for example, Spolski, R., Li, P. & Leonard, W. J. Biology and regulation of IL-2: from molecular mechanisms to human therapy. Nat Rev Immunol 18, 648-659 (2018)). For example, IL-2 can promote a pathogen clearing response due to its effectiveness at inducing an immune response, acting as an autocrine factor for T cells and supporting the development of cytotoxic T cells, stimulating NK cells proliferation and cytolytic activity. Accordingly, in some instances, Interleukin-2 (IL-2) can be useful for activating the immune response in the context of a fusion protein comprising an interleukin polypeptide fused (e.g., linked) to two or more polypeptides that inhibit TGFβ activity.

IL-2 is a small, 15.5-kDa four α-helical bundle cytokine. It is produced predominately by antigen stimulated CD4+ T cells, while it can also be produced by CD8+ cells, natural killer (NK) cells, and activated dendritic cells (DC). IL-2 is an important factor for the maintenance of CD4+ regulatory T cells and plays a critical role in the differentiation of CD4+ T cells into a variety of T cell subsets. It can promote CD8+ T-cell and NK cell cytotoxicity activity, and modulate T-cell differentiation programs in response to antigen, promoting naive CD4+ T-cell differentiation into T helper-1 (Th1) and T helper-2 (Th2) cells while inhibiting T helper-17 (Th17) differentiation. Notably, IL-2 was one of the first FDA-approved immunotherapy drugs for metastatic melanoma and renal cell cancer. However, IL-2 immunotherapy has not been widely applied due to its short half-life in vivo and severe toxicity at the therapeutic dosage.

In an aspect, interleukin-2 or IL-2 generally includes any native IL-2 from any vertebrate source, including mammals such as primates (e.g., humans) and rodents (e.g., mice and rats), unless otherwise indicated. IL-2 includes unprocessed IL-2 as well as any form of IL-2 that results from processing in the cell. The term also encompasses naturally occurring variants of IL-2, e.g., splice variants or allelic variants. The amino acid sequence of an exemplary human IL-2 is shown in SEQ ID NO: 1. Unprocessed human IL-2 additionally comprises an N-terminal 20 amino acid signal peptide, which is absent in the mature IL-2 molecule. IL-2 also includes "wild-type IL-2" or a naturally occurring IL-2. The sequence of a native human IL-2 molecule is shown in SEQ ID NO: 1. For the purpose of the present disclosure, the term wild-type also encompasses forms of IL-2 comprising one or more amino acid mutations. For example, the fusion proteins described herein can comprise an IL-2 polypeptide having greater than 80%, greater than 85%, greater than 90%, greater than 95%, greater than 96%, greater than 97%, greater than 98%, or greater than 99% sequence identity to the amino acid sequence of SEQ ID NO: 1.

In some embodiments, the fusion protein comprises an IL-2 sequence comprising an amino acid sequence having about 85% to about 100% sequence identity to SEQ ID NO: 1. In some embodiments, the fusion protein comprises an IL-2 sequence comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 1. In some embodiments, the fusion protein comprises an IL-2 sequence comprising an amino acid sequence having about 85%, about 90%, about 95%, about 96%, about 97%, about 98%, about 99%, or about 100% sequence identity to SEQ ID NO: 1. In some embodiments, the fusion protein comprises an IL-2 sequence comprising an amino acid sequence having at least about 85%, at least about 90%, at least about 95%, at least about 96%, at least about 97%, at least about 98%, or at least about 99% sequence identity to SEQ ID NO: 1.

The IL-2 polypeptide can comprise a full-length native sequence or truncations thereof. In some embodiments, the IL-2 polypeptide is a truncated IL-2 polypeptide. The truncated IL-2 polypeptide can comprise N-terminus truncations, C-terminus truncations, or a combination thereof. In some embodiments, the fusion protein comprises an IL-2 polypeptide that is truncated by about 2 amino acids to about 20 amino acids (e.g., relative to a full-length IL-2 polypeptide). In some embodiments, the fusion protein comprises an IL-2 polypeptide that is truncated by about 2 amino acids to about 5 amino acids, about 2 amino acids to about 7 amino acids, about 2 amino acids to about 8 amino acids, about 2 amino acids to about 10 amino acids, about 2 amino acids to about 15 amino acids, about 2 amino acids to about 20 amino acids, about 5 amino acids to about 7 amino acids, about 5 amino acids to about 8 amino acids, about 5 amino acids to about 10 amino acids, about 5 amino acids to about 15 amino acids, about 5 amino acids to about 20 amino acids, about 7 amino acids to about 8 amino acids, about 7 amino acids to about 10 amino acids, about 7 amino acids to about 15 amino acids, about 7 amino acids to about 20 amino acids, about 8 amino acids to about 10 amino acids, about 8 amino acids to about 15 amino acids, about 8 amino acids to about 20 amino acids, about 10 amino acids to about 15 amino acids, about 10 amino acids to about 20 amino acids, or about 15 amino acids to about 20 amino acids (e.g., relative to a full-length IL-2 polypeptide). In some embodiments, the fusion protein comprises an IL-2 polypeptide that is truncated by about 2 amino acids, about 5 amino acids, about 7 amino acids, about 8 amino acids, about 10 amino acids, about 15 amino acids, or about 20 amino acids (e.g., relative to a full-length IL-2 polypeptide). In some embodiments, the fusion protein comprises an IL-2 polypeptide that is truncated by at least about 2 amino acids, at least about 5 amino acids, at least about 7 amino acids, at least about 8 amino acids, at least about 10 amino acids, or at least about 15 amino acids (e.g., relative to a full-length IL-2 polypeptide). In some embodiments, the fusion protein comprises an IL-2 polypeptide that is truncated by at most about 5 amino acids, at most about 7 amino acids, at most about 8 amino acids, at most about 10 amino acids, at most about 15 amino acids, or at most about 20 amino acids (e.g., relative to a full-length IL-2 polypeptide). In some embodiments, the fusion protein comprises an IL-2 polypeptide having an amino acid sequence of SEQ ID NO: 2.

In some embodiments, the fusion protein comprises an IL-2 polypeptide comprising an amino acid sequence having about 85% to about 100% sequence identity to SEQ ID NO: 2. In some embodiments, the fusion protein comprises an IL-2 polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 2. In some embodiments, the fusion protein comprises an IL-2 polypeptide comprising an amino acid sequence having about 85%, about 90%, about 95%, about 96%, about 97%, about 98%, about 99%, or about 100% sequence identity to SEQ ID NO: 2. In some embodiments, the fusion protein comprises an IL-2 polypeptide comprising an amino acid sequence having at least about 85%, at least about 90%, at least about 95%, at least about 96%, at least about 97%, at least about 98%, or at least about 99% sequence identity to SEQ ID NO: 2.

Interleukin-15 (IL-15) is also an interleukin useful for activating the immune response in the context of a fusion protein provided herein. Interleukin 15 (IL-15) is a cytokine of about 12-14 kilodaltons comprising a four-α-helix structure. IL-15 belongs to the family of cytokines consisting of interleukins IL-2, IL-4, IL-7, IL-9, and IL-21. IL-15 signals through a receptor complex composed of the IL-2/IL-15 receptor β (IL-15Rβ) (CD122) subunit, which is shared with IL-2 and the common gamma chain (γC) (CD132) receptor subunit, which is also utilized by all of the additional family members. Notably, IL-15 is a growth factor for T cells and NK cells, and plays an important role in the development, proliferation, and activation of these immune cells. Although IL-15 has a potential for therapeutic use, natural IL-15 has therapeutic development issues, namely a low biological potency and a short half-life.

The term "interleukin-15" or "IL-15" refers to any native IL-15 from any vertebrate source, including mammals such as primates (e.g., humans) and rodents (e.g., mice and rats), unless otherwise indicated. IL-15 includes unprocessed IL-15 as well as any form of IL-15 that results from processing in the cell. The term also encompasses naturally occurring variants of IL-15, e.g., splice variants or allelic variants. The amino acid sequence of an exemplary human IL-15 is shown in SEQ ID NO: 4 IL-15 also includes "wild-type IL-15" or a naturally occurring IL-15. The sequence of a native human IL-15 molecule is shown in SEQ ID NO: 4. For the purpose of the present disclosure, the term wild-type IL-15 also encompasses forms of IL-15 comprising one or more amino acid mutations. For example, the fusion proteins described herein can comprise an IL-15 polypeptide comprising an amino acid sequence having greater than 80%, greater than 85%, greater than 90% greater than 95%, greater than 96%, greater than 97%, greater than 98%, or greater than 99% sequence identity to the amino acid sequence of SEQ ID NO: 4.

In some embodiments, the fusion protein comprises an IL-15 polypeptide comprising an amino acid sequence having about 85% to about 100% sequence identity to SEQ ID NO: 4. In some embodiments, the fusion protein comprises an IL-15 polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 4. In some embodiments, the fusion protein comprises an IL-15 polypeptide comprising an amino acid sequence having about 85%, about 90%, about 95%, about 96%, about 97%, about 98%, about 99%, or about 100% sequence identity to SEQ ID NO: 4. In some embodiments, the fusion protein comprises an IL-15 polypeptide comprising an amino acid sequence having at least about 85%, at least about 90%, at least about 95%, at least about 96%, at least about 97%, at least about 98%, or at least about 99% sequence identity to SEQ ID NO: 4.

The IL-15 polypeptide can comprise a full-length native sequence or truncations thereof. In some embodiments, the IL-15 polypeptide is a truncated IL-15 polypeptide. The truncated IL-15 polypeptide can comprise N-terminus truncations, C-terminus truncations, or a combination thereof. In some embodiments, the fusion protein comprises an IL-15 polypeptide that is truncated by about 2 amino acids to about 20 amino acids (e.g., relative to a full-length IL-15 polypeptide). In some embodiments, the fusion protein comprises an IL-15 polypeptide that is truncated by about 2 amino acids to about 5 amino acids, about 2 amino acids to about 7 amino acids, about 2 amino acids to about 8 amino acids, about 2 amino acids to about 10 amino acids, about 2 amino acids to about 15 amino acids, about 2 amino acids to about 20 amino acids, about 5 amino acids to about 7 amino acids, about 5 amino acids to about 8 amino acids, about 5 amino acids to about 10 amino acids, about 5 amino acids to about 15 amino acids, about 5 amino acids to about 20 amino acids, about 7 amino acids to about 8 amino acids, about 7 amino acids to about 10 amino acids, about 7 amino acids to about 15 amino acids, about 7 amino acids to about 20 amino acids, about 8 amino acids to about 10 amino acids, about 8 amino acids to about 15 amino acids, about 8 amino acids to about 20 amino acids, about 10 amino acids to about 15 amino acids, about 10 amino acids to about 20 amino acids, or about 15 amino acids to about 20 amino acids (e.g., relative to a full-length IL-15 polypeptide). In some embodiments, the fusion protein comprises an IL-15 polypeptide that is truncated by about 2 amino acids, about 5 amino acids, about 7 amino acids, about 8 amino acids, about 10 amino acids, about 15 amino acids, or about 20 amino acids (e.g., relative to a full-length IL-15 polypeptide). In some embodiments, the fusion protein comprises an IL-15 polypeptide that is truncated by at least about 2 amino acids, at least about 5 amino acids, at least about 7 amino acids, at least about 8 amino acids, at least about 10 amino acids, or at least about 15 amino acids (e.g., relative to a full-length IL-15 polypeptide). In some embodiments, the fusion protein comprises an IL-15 polypeptide that is truncated by at most about 5 amino acids, at most about 7 amino acids, at most about 8 amino acids, at most about 10 amino acids, at most about 15 amino acids, or at most about 20 amino acids (e.g., relative to a full-length IL-15 polypeptide). In some embodiments, the fusion protein comprises an IL-15 polypeptide having an amino acid sequence of SEQ ID NO: 5.

In some embodiments, the fusion protein comprises an IL-15 polypeptide comprising an amino acid sequence having about 85% to about 100% sequence identity to SEQ ID NO: 5. In some embodiments, the fusion protein comprises an IL-15 polypeptide comprising an amino acid sequence about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% having sequence identity to SEQ ID NO: 5. In some embodiments, the fusion protein comprises an IL-15 polypeptide comprising an amino acid sequence having about 85%, about 90%, about 95%, about 96%, about 97%, about 98%, about 99%, or about 100% sequence identity to SEQ ID NO: 5. In some embodiments, the fusion protein comprises an IL-15 polypeptide comprising an amino acid sequence having at least about 85%, at least about 90%, at least about 95%, at least about 96%, at least about 97%, at least about 98%, or at least about 99% sequence identity to SEQ ID NO: 5.

TGFβ Inhibiting Polypeptides

As described herein, the fusion proteins provided herein generally comprise an interleukin polypeptide (e.g., IL-2 or IL-15) fused (e.g., linked) to two or more polypeptides that inhibit TGFβ activity (e.g., two or more polypeptides that bind a TGFβ protein). The transforming growth factor β (TGFβ) superfamily is a large group of soluble factors (e.g., proteins) that initiate and control activation, proliferation, and differentiation of many cell types, thus playing important roles in embryonal development and homeostasis. The TGFβ superfamily includes several subfamilies: the activin/inhibin family, bone morphogenetic proteins (BMPs), growth differentiation factors (GDFs), the TGFβ subfamily, and glial cell line-derived neurotrophic factor (GDNF) family. TGFβ superfamily has three types: TGFβ1, TGFβ2, and TGFβ3. TGFβ superfamily proteins have been discovered in a variety of species, including invertebrates as well as vertebrates. TGFβ malfunction can lead to developmental disorders, severe defects in organ function, and is associated with several diseases.

The inhibition and suppression of TGFβ superfamily activity can be achieved through the use of fusion proteins comprising, in addition to an interleukin polypeptide, two or more TGFβ superfamily receptor polypeptides. In the context of the fusion proteins described herein, the two or more TGFβ superfamily receptor polypeptides yield a multivalent single chain polypeptide capable of binding two or more TGFβ proteins. Generally, ligands of the TGFβ superfamily bind to receptor complexes consisting of type I and type II receptor subunits. As disclosed herein, polypeptides derived from TGFβ superfamily receptors are useful for inhibiting or suppressing TGFβ superfamily ligands. For example, in some embodiments, the TGFβ superfamily receptor is selected from the group consisting of: an activin receptor polypeptide or fragment thereof, a bone morphogenetic protein (BMP) receptor polypeptide or fragment thereof, a glial cell-derived neurotrophic factor (GDNF) receptor polypeptide or fragment thereof, and a TGFβ receptor polypeptide or fragment thereof.

Within the TGFβ superfamily of proteins, the TGFβ sub-family of proteins comprises TGFβ1, TGFβ2, and TGFβ3. Among TGFβs, TGFβ1 is the most potent immunosuppressive cytokine described to date, and exerts deleterious effects (e.g., immunosuppression) on several components of the immune system response against pathogens. Notably, TGFβ proteins (e.g., TGFβ1) diminish or reduce the effector functions of macrophages, B cells, cytotoxic T cells, dendritic cells, and NK cells, where TGFβ acts as a negative regulator of IFNγ production via its mediators SMAD2, SMAD3, and SMAD4.

Most cell types express three sizes of receptors for TGFβ, designated Type I (53 kDa), Type II (70-85 kDa), and Type III (250-350 kDa). The Type I receptor is a membrane-bound serine/threonine kinase that apparently requires the presence of the Type II receptor to bind TGFβ. The Type II receptor is also a membrane-bound serine/threonine kinase that binds TGFβ1 and TGFβ3 with high affinity and TGFβ2 with much lower affinity. The Type I and Type II receptors together form a heterodimeric signaling complex that is essential for the transduction of the anti-proliferative signals of TGFβ. The Type III receptor is a transmembrane proteoglycan with a large extracellular domain and a 43 amino acid residue cytoplasmic domain. The cytoplasmic domain of the Type III receptor lacks an obvious signaling motif and the receptor may not be involved directly in signal transduction. Notably, the soluble extracellular domain of the TβRII, consisting of the extracellular domain of the receptor binds TGF-β1 and TGF-β3 with high affinity.

Accordingly, the TGFβ receptor TβRII polypeptides are useful in TGFβ binding polypeptides of the multi-functional fusion proteins described herein. Particularly, TGFβ receptor TβRII polypeptides are useful for inhibiting or reducing TGFβ1 activity or signaling associated therewith. The term "soluble transforming growth factor (TGF) β receptor type II B" or "sTβRII" as used herein refers to a soluble, or non-membrane form of the alternatively spliced transforming growth factor β type II receptor, preferably the ectodomain of the TGFβ type II receptor from any species or source and includes the full-length ectodomain as well as fragments or portions of the ectodomain. In some embodiments, the sTβRIIB is human or mouse. The human TGFβ receptor II has the amino acid sequence of SEQ ID NOs: 6 or 7 (short and long isoforms, respectively). The term "sTβRII fragment" as used herein means at least about 10%, at least about 20%, at least about 30%, at least about 40%, at least about 50%, at least about 60%, at least about 70%, at least about 80%, at least about 90%, at least about 95%, or more of the entire length of the reference polypeptide. In one embodiment, the polypeptide is truncated at the N-terminal or C-terminal end to permit cloning.

In some embodiments, the fusion protein comprises an sTβRII polypeptide comprising an amino acid sequence having about 85% to about 100% sequence identity to SEQ ID NO: 6. In some embodiments, the fusion protein comprises an sTβRII polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 6. In some embodiments, the fusion protein comprises an sTβRII polypeptide comprising an amino acid sequence having about 85%, about 90%, about 95%, about 96%, about 97%, about 98%, about 99%, or about 100% sequence identity to SEQ ID NO: 6. In some embodiments, the fusion protein comprises an sTβRII polypeptide comprising an amino acid sequence having at least about 85%, about 90%, about 95%, about 96%, about 97%, about 98%, or about 99% sequence identity to SEQ ID NO: 6.

In some embodiments, the fusion protein comprises an sTβRII polypeptide comprising an amino acid sequence having about 85% to about 100% sequence identity to SEQ ID NO: 7. In some embodiments, the fusion protein comprises an sTβRII polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 6. In some embodiments, the fusion protein comprises an sTβRII polypeptide comprising an amino acid sequence having about 85%, about 90%, about 95%, about 96%, about 97%, about 98%, about 99%, or about 100% sequence identity to SEQ ID NO: 7. In some embodiments, the fusion protein comprises an sTβRII polypeptide comprising an amino acid sequence having at least about 85%, at least about 90%, at least about 95%, at least about 96%, at least about 97%, at least about 98%, or at least about 99% sequence identity to SEQ ID NO: 7.

As described herein, the two or more sTβRII receptor polypeptides utilize the ectodomain of a native sTβRII receptor. Accordingly, the sTβRII receptor polypeptide used herein comprises SEQ ID NO: 8 (e.g., the short isoform of sTβRII), SEQ ID NO: 9 (e.g., the long isoform of sTβRII), or a combination thereof.

In some embodiments, the fusion protein comprises an sTβRII polypeptide comprising an amino acid sequence having about 85% to about 100% sequence identity to SEQ ID NO: 8. In some embodiments, the fusion protein comprises an sTβRII polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 8. In some embodiments, the fusion protein comprises an sTβRII polypeptide comprising an amino acid sequence having about 85%, about 90%, about 95%, about 96%, about 97%, about 98%, about 99%, or about 100% sequence identity to SEQ ID NO: 8. In some embodiments, the fusion protein comprises an TβRII polypeptide comprising an amino acid sequence having at least about 85%, at least about 90%, at least about 95%, at least about 96%, at least about 97%, at least about 98%, or at least about 99% sequence identity to SEQ ID NO: 8.

In some embodiments, the fusion protein comprises an sTβRII polypeptide comprising an amino acid sequence having about 85% to about 100% sequence identity to SEQ ID NO: 9. In some embodiments, the fusion protein comprises an sTBRII polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 9. In some embodiments, the fusion protein comprises an sTβRII polypeptide comprising an amino acid sequence having about 85%, about 90%, about 95%, about 96%, about 97%, about 98%, about 99%, or about 100% sequence identity to SEQ ID NO: 9. In some embodiments, the fusion protein comprises an TβRII polypeptide comprising an amino acid sequence having at least about 85%, at least about 90%, at least about 95%, at least about 96%, at least about 97%, at least about 98%, or at least about 99% sequence identity to SEQ ID NO: 9.

The sTβRII polypeptide of SEQ ID NO: 8 or SEQ ID NO: 9 can comprise additional truncations thereof. In some embodiments, the sTβRII polypeptide is a truncated sTβRII polypeptide. The truncated sTβRII polypeptide can comprise N-terminus truncations, C-terminus truncations, or a combination thereof. In some embodiments, the fusion protein comprises an sTβRII that is truncated by about 2 amino acids to about 20 amino acids (e.g., relative to a full-length sTβRII polypeptide). In some embodiments, the fusion protein comprises an sTβRII that is truncated by about 2 amino acids to about 5 amino acids, about 2 amino acids to about 7 amino acids, about 2 amino acids to about 8 amino acids, about 2 amino acids to about 10 amino acids, about 2 amino acids to about 15 amino acids, about 2 amino acids to about 20 amino acids, about 5 amino acids to about 7 amino acids, about 5 amino acids to about 8 amino acids, about 5 amino acids to about 10 amino acids, about 5 amino acids to about 15 amino acids, about 5 amino acids to about 20 amino acids, about 7 amino acids to about 8 amino acids, about 7 amino acids to about 10 amino acids, about 7 amino acids to about 15 amino acids, about 7 amino acids to about 20 amino acids, about 8 amino acids to about 10 amino acids, about 8 amino acids to about 15 amino acids, about 8 amino acids to about 20 amino acids, about 10 amino acids to about 15 amino acids, about 10 amino acids to about 20 amino acids, or about 15 amino acids to about 20 amino acids (e.g., relative to a full-length sTβRII polypeptide). In some embodiments, the fusion protein comprises an sTβRII that is truncated by about 2 amino acids, about 5 amino acids, about 7 amino acids, about 8 amino acids, about 10 amino acids, about 15 amino acids, or about 20 amino acids. In some embodiments, the fusion protein comprises an sTβRII that is truncated by at least about 2 amino acids, at least about 5 amino acids, at least about 7 amino acids, at least about 8 amino acids, at least about 10 amino acids, or at least about 15 amino acids. In some embodiments, the fusion protein comprises an sTβRII that is truncated by at most about 5 amino acids, at most about 7 amino acids, at most about 8 amino acids, at most about 10 amino acids, at most about 15 amino acids, or at most about 20 amino acids (e.g., relative to a full-length sTβRII polypeptide).

Multi-Functional and Multi-Valent Fusion Protein Compositions

Provided herein are fusion polypeptides comprising: (a) an interleukin (IL) polypeptide; (b) a first TGFβ superfamily receptor polypeptide; and (c) a second TGFβ superfamily receptor polypeptide. Also provided herein are fusion polypeptides comprising: a first IL polypeptide that binds to and agonizes the IL receptor; a second polypeptide that binds to and sequesters soluble TGFβ; and a third polypeptide that binds to and sequesters soluble TGFβ.

In some embodiments, the IL polypeptide is IL-2. In some embodiments, the IL polypeptide is IL-15. In certain embodiments the IL-2 polypeptide comprises SEQ ID NO: 2 or 3. In certain embodiments the IL-2 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 2 or 3. In certain embodiments, the IL-15 polypeptide comprises SEQ ID NO: 4 or 5. In certain embodiments, the IL-15 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 4 or 5. In certain embodiments, the IL polypeptide is a truncated polypeptide.

In some embodiments, the first TGFβ superfamily receptor polypeptide and/or the second TGFβ superfamily receptor polypeptide comprises a soluble TGFβ receptor II polypeptide. In some embodiments, the first TGFβ superfamily receptor polypeptide and the second TGFβ superfamily receptor polypeptide comprises a soluble TGFβ receptor II polypeptide comprising SEQ ID NO: 8, SEQ ID NO: 9, or a combination thereof. In some embodiments, the first TGFβ superfamily receptor polypeptide comprises an amino acid sequence of SEQ ID NO: 8 and the second TGFβ superfamily receptor polypeptide comprises a truncation of an amino acid sequence of SEQ ID NO: 9. In certain embodiments, the soluble TGFβ receptor II polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 8 or SEQ ID NO: 9.

In another embodiment, the second polypeptide that binds to and sequesters soluble TGFβ and/or the third polypeptide that binds to and sequesters soluble TGFβ comprises a soluble TGFβ receptor II polypeptide. In some embodiments, the second polypeptide that binds to and sequesters soluble TGFβ and/or the third polypeptide that binds to and sequesters soluble TGFβ comprises a soluble TGFβ receptor II polypeptide comprising SEQ ID NO: 8, SEQ ID NO: 9, or a combination thereof. In certain embodiments, the soluble TGFβ receptor II polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 8 or SEQ ID NO: 9.

In some embodiments, the first TGFβ superfamily receptor polypeptide and/or the second TGFβ superfamily receptor polypeptide target a TGF-β1 polypeptide, a TGF-β2 polypeptide, a TGF-β3 polypeptide, a activin βA polypeptide, a activin βB polypeptide, a activin βC polypeptide, a activin βE polypeptide, a bone morphogenic protein (BMP) 2 polypeptide, a BMP 3 polypeptide, a BMP4 polypeptide, a BMP 5 polypeptide, a BMP 6 polypeptide, a BMP 7 polypeptide, a BMP 8 polypeptide, a BMP 9 polypeptide, a BMP 10 polypeptide, a BMP 11 polypeptide, a BMP 12 polypeptide, a BMP 13 polypeptide, a BMP 14 polypeptide, a BMP 15 polypeptide, a growth differentiation factor (GDF) 1 polypeptide, a GDF 3 polypeptide, a GDF 8 polypeptide, a GDF 9 polypeptide, a GDF 15 polypeptide, a Nodal polypeptide, a Inhibin α polypeptide, an anti-Mullerian Hormone polypeptide, a Lefty 1 polypeptide, a Lefty 2 polypeptide, an arteman polypeptide, a Persephin polypeptide, or a Neurturin polypeptide. In some embodiments, the first TGFβ superfamily receptor polypeptide and/or the second TGFβ superfamily receptor polypeptide binds a TGFβ1 polypeptide, a TGFβ2 polypeptide, a TGFβ3 polypeptide, or any combination thereof. In some embodiments, the first TGFβ superfamily receptor polypeptide and/or the second TGFβ superfamily receptor polypeptide binds a TGFβ1 polypeptide.

In another embodiment, the second polypeptide and/or the third polypeptide binds to and sequesters a TGFβ1 polypeptide, a TGFβ2 polypeptide, a TGFβ3 polypeptide, or any combination thereof. In certain embodiments, the second polypeptide and/or the third polypeptide binds to and sequesters a TGFβ1 polypeptide.

A polypeptide of the fusion polypeptide can be "fused" or "linked" via a linker. The linker may be a polypeptide linker or other linker of suitable flexibility so as not to inhibit binding of either targeting polypeptide (e.g., the IL2 polypeptide or TβRII receptor polypeptide). The linker polypeptide can be unstructured (e.g., lacking secondary structure), structured, or a combination thereof. In some embodiments, the linker sequence is a natural amino acid sequence of the IL polypeptide or soluble TβRII polypeptide. In some embodiments, the linker is not native to the IL polypeptide or TGF receptor polypeptide. For example, a non-native linker can comprise poly-glycine, poly-alanine, poly-serine amino acid or a combination thereof (e.g., GSSG, GGSS, GSAGG, etc.).

In some embodiments, the linker is a non-natural or synthetic linker. The term "synthetic linker" as used herein includes a chemical moiety comprising or derived from a group of atoms that is covalently attached to a targeting agent, and that is also covalently attached to a cytotoxic moiety. Linkers include compounds comprising or derived from divalent radicals such as an alkylene, an arylene, a heteroarylene, moieties such as: —(CR2)nO(CR2)n- wherein R2 is independently repeating units of alkyloxy (e.g. polyethylenoxy, PEG, polymethyleneoxy) and alkylamino (e.g. polyethyleneamino, polyetheramines such as Jeffamine™) and n is independently >1, in particular n may be 1 to 15; compounds including the linkers described in Example 1, N-succinimidyl 4-(maleimidomethyl)cyclohexanecarboxylate (SMCC) and N-succinimidyl 4-(2-pyridyldithio) butanoate (SPDB); and diacid ester and amides including succinate, succinamide, diglycolate, malonate, and caproamide as well as peptides, such as but not limited to repeating units of G, A and C (for example up to 10) with one or more lys residues or other suitable chemical groups for linking to a targeting agent and a cytotoxic moiety. The linker is optionally Cl-30 alkylene, unsubstituted or substituted with one or more substituents, and/or optionally interrupted with one or more heteromoieties independently selected from O, S, NR1, and/or optionally interrupted with one or more of C(O) and C(S), wherein R1 is independently selected from H, and Cl-6 alkyl. The linker can comprise a non-cleavable (stable linker) or cleavable unit (labile linker) such as a peptide bond or a disulfide bond. The linker can be conjugated to the targeting agent and/or the cytotoxic moiety via reactive functional groups.

Both cleavable and non-cleavable linkers can be used in the synthesis of fusion proteins (ADCs). Cleavable linkers include motifs that are either sensitive to lysosomal proteases or sensitive to an acidic pH (such as hydrazone, which is hydrolysed to cleave the linker in gemtuzumab ozogamicin and inotuzumab ozogamicin), or they can contain disulfide bridges that can be reduced by glutathione. The steric hindrance of disulfide bridges can be optimized to limit premature cleavage inside the cell. Generally, the disulfide linker is initially cleaved to release the thiol compound. Acid-cleavable linkers, such as hydrazone, are designed to remain stable at the neutral pH in the blood circulation, but in acidic cellular compartments they undergo hydrolysis and release the cytotoxic drug.

In some embodiments, the linker (e.g., peptide linker) comprises about 10 amino acids to about 100 amino acids. In some embodiments, the linker comprises about 10 amino acids to about 15 amino acids, about 10 amino acids to about 20 amino acids, about 10 amino acids to about 25 amino acids, about 10 amino acids to about 30 amino acids, about 10 amino acids to about 40 amino acids, about 10 amino acids to about 50 amino acids, about 10 amino acids to about 75 amino acids, about 10 amino acids to about 100 amino acids, about 15 amino acids to about 20 amino acids, about 15 amino acids to about 25 amino acids, about 15 amino acids to about 30 amino acids, about 15 amino acids to about 40 amino acids, about 15 amino acids to about 50 amino acids, about 15 amino acids to about 75 amino acids, about 15 amino acids to about 100 amino acids, about 20 amino acids to about 25 amino acids, about 20 amino acids to about 30 amino acids, about 20 amino acids to about 40 amino acids, about 20 amino acids to about 50 amino acids, about 20 amino acids to about 75 amino acids, about 20 amino acids to about 100 amino acids, about 25 amino acids to about 30 amino acids, about 25 amino acids to about 40 amino acids, about 25 amino acids to about 50 amino acids, about 25 amino acids to about 75 amino acids, about 25 amino acids to about 100 amino acids, about 30 amino acids to about 40 amino acids, about 30 amino acids to about 50 amino acids, about 30 amino acids to about 75 amino acids, about 30 amino acids to about 100 amino acids, about 40 amino acids to about 50 amino acids, about 40 amino acids to about 75 amino acids, about 40 amino acids to about 100 amino acids, about 50 amino acids to about 75 amino acids, about 50 amino acids to about 100 amino acids, or about 75 amino acids to about 100 amino acids. In some embodiments, the linker comprises about 10 amino acids, about 15 amino acids, about 20 amino acids, about 25 amino acids, about 30 amino acids, about 40 amino acids, about 50 amino acids, about 75 amino acids, or about 100 amino acids. In some embodiments, the linker comprises at least about 10 amino acids, about 15 amino acids, about 20 amino acids, about 25 amino acids, about 30 amino acids, about 40 amino acids, about 50 amino acids, or about 75 amino acids. In some embodiments, the linker comprises at most about 15 amino acids, at most about 20 amino acids, at most about 25 amino acids, at most about 30 amino acids, at most about 40 amino acids, at most about 50 amino acids, at most about 75 amino acids, or at most about 100 amino acids.

Figure 3:
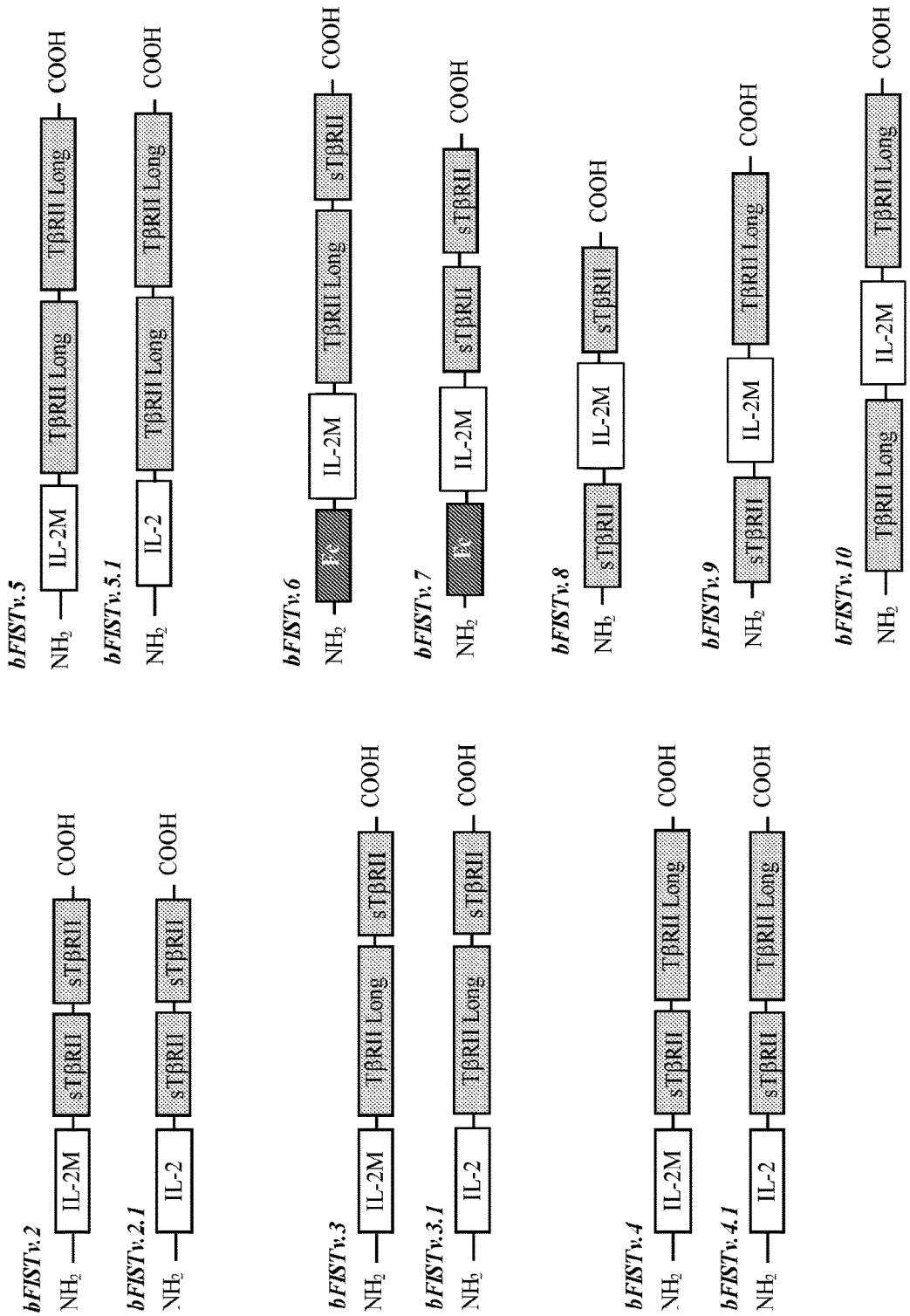
FIG. 3 shows a schematic representation of exemplary bivalent FIST (bFIST) fusion polypeptides.

Generally, different polypeptide elements of the fusion polypeptides can be arranged or ordered, from N-terminus to C-terminus, in any number of different combinations. For example, described herein are fusion polypeptides that comprise, from N-terminus to C-terminus, an IL polypeptide, a first TGFβ superfamily receptor polypeptide, and a second TGFβ superfamily receptor polypeptide. By way of further example, the fusion polypeptides as described herein, can also comprise, from N-terminus to C-terminus, a first TGFβ superfamily receptor polypeptide, an IL polypeptide, and a second TGFβ superfamily receptor polypeptide. In some embodiments, the fusion polypeptide further comprises a pharmacokinetic extender polypeptide (e.g., an Fc polypeptide or HSA polypeptide), wherein the fusion polypeptides further comprising the pharmacokinetic extender can be arranged or ordered, from N-terminus to C-terminus, in any number of different combinations. FIG. 3 shows a non-limiting schematic representation of exemplary embodiments of fusion polypeptides that comprise an IL polypeptide, a first TGFβ superfamily receptor polypeptide, and a second TGFβ superfamily receptor polypeptide (e.g., SEQ ID NOs: 10-25)

In some embodiments, the fusion polypeptide comprises an amino acid sequence of SEQ ID NO: 10. In some embodiments, the fusion polypeptide comprises an amino acid sequence of SEQ ID NO: 11. In some embodiments, the fusion polypeptide comprises an amino acid sequence of SEQ ID NO: 12. In some embodiments, the fusion polypeptide comprises an amino acid sequence of SEQ ID NO: 13. In some embodiments, the fusion polypeptide comprises an amino acid sequence of SEQ ID NO: 14. In some embodiments, the fusion polypeptide comprises an amino acid sequence of SEQ ID NO: 15. In some embodiments, the fusion polypeptide comprises an amino acid sequence of SEQ ID NO: 16. In some embodiments, the fusion polypeptide comprises an amino acid sequence of SEQ ID NO: 17. In some embodiments, the fusion polypeptide comprises an amino acid sequence of SEQ ID NO: 18. In some embodiments, the fusion polypeptide comprises an amino acid sequence of SEQ ID NO: 19. In some embodiments, the fusion polypeptide comprises an amino acid sequence of SEQ ID NO: 20. In some embodiments, the fusion polypeptide comprises an amino acid sequence of SEQ ID NO: 21. In some embodiments, the fusion polypeptide comprises an amino acid sequence of SEQ ID NO: 22. In some embodiments, the fusion polypeptide comprises an amino acid sequence of SEQ ID NO: 23. In some embodiments, the fusion polypeptide comprises an amino acid sequence of SEQ ID NO: 24. In some embodiments, the fusion polypeptide comprises an amino acid sequence of SEQ ID NO: 25.

In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to any one of SEQ ID NOs: 10 to 20. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to SEQ ID NO: 10. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to SEQ ID NO: 11. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 12. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 13. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 14. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 15.

In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 16. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 17. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 18. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 19. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 20. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 21. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 22. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 23. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 24. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 25.

In some embodiments, the fusion polypeptide consists of an amino acid sequence of SEQ ID NO: 10. In some embodiments, the fusion polypeptide consists of an amino acid sequence of SEQ ID NO: 11. In some embodiments, the fusion polypeptide consists of an amino acid sequence of SEQ ID NO: 12. In some embodiments, the fusion polypeptide consists of an amino acid sequence of SEQ ID NO: 13. In some embodiments, the fusion polypeptide consists of an amino acid sequence of SEQ ID NO: 14.

In some embodiments, the fusion polypeptide consists of an amino acid sequence of SEQ ID NO: 15. In some embodiments, the fusion polypeptide consists of an amino acid sequence of SEQ ID NO: 16. In some embodiments, the fusion polypeptide consists of an amino acid sequence of SEQ ID NO: 17. In some embodiments, the fusion polypeptide consists of an amino acid sequence of SEQ ID NO: 18. In some embodiments, the fusion polypeptide consists of an amino acid sequence of SEQ ID NO: 19. In some embodiments, the fusion polypeptide consists of an amino acid sequence of SEQ ID NO: 20. In some embodiments, the fusion polypeptide consists of an amino acid sequence of SEQ ID NO: 21. In some embodiments, the fusion polypeptide consists of an amino acid sequence of SEQ ID NO: 22. In some embodiments, the fusion polypeptide consists of an amino acid sequence of SEQ ID NO: 23. In some embodiments, the fusion polypeptide consists of an amino acid sequence of SEQ ID NO: 24. In some embodiments, the fusion polypeptide consists of an amino acid sequence of SEQ ID NO: 25.

The fusion polypeptides disclosed herein can further comprise a pharmacokinetic modulating polypeptide (e.g., a polypeptide that improves the pharmacokinetic profile of a therapeutic agent). For example, the fusion protein can further comprise an immunoglobulin Fc polypeptide or human serum albumin (HSA) polypeptide fused to the N-terminus of the IL polypeptide. In some embodiments, the immunoglobulin Fc region polypeptide is a human immunoglobulin Fc region polypeptide. In some embodiments, the immunoglobulin Fc region is an IgG Fc region. In some embodiments, the IgG Fc region is an IgG1, IgG2, IgG3, or IgG4 Fc region. In some embodiments, the PK modulator comprises an albumin polypeptide. In some embodiments, the albumin polypeptide is a human albumin polypeptide.

In certain embodiments the fusion polypeptides of the current disclosure are included in a pharmaceutical composition comprising one or more pharmaceutically acceptable excipients, carriers, and/or diluents. In certain embodiments, the fusion proteins of the current disclosure are administered suspended in a sterile solution. In certain embodiments, the solution comprises about 0.9% NaCl. In certain embodiments, the solution comprises about 5.0% dextrose. In certain embodiments, the solution further comprises one or more of: buffers, for example, acetate, citrate, histidine, succinate, phosphate, bicarbonate and hydroxymethylaminomethane (Tris); surfactants, for example, polysorbate 80, polysorbate 20, and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, Ethylenediaminetetraacetic acidor ethylene glycol-bis(β-aminoethyl ether)-N,N,N',N'-tetraacetic acid.

In certain embodiments, the fusion proteins of the current disclosure are shipped/stored lyophilized and reconstituted before administration. In certain embodiments, lyophilized fusion polypeptide formulations comprise a bulking agent such as, mannitol, sorbitol, sucrose, trehalose, dextran 40, or combinations thereof. The lyophilized formulation can be contained in a vial comprised of glass or other suitable non-reactive material. The fusion proteins when formulated, whether reconstituted or not, can be buffered at a certain pH, generally less than 7.0. In certain embodiments, the pH can be between 4.5 and 6.5, 4.5 and 6.0, 4.5 and 5.5, 4.5 and 5.0, or 5.0 and 6.0.

In certain embodiments, described herein is a method of preparing a treatment comprising admixing one or more pharmaceutically acceptable excipients, carriers, or diluents and a fusion polypeptide of the current disclosure. In certain embodiments, described herein is a method of preparing a treatment for storage or shipping comprising lyophilizing one or more fusion polypeptides of the current disclosure.

The fusion polypeptides described herein (e.g., SEQ ID NOs: 10 to 25) can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors, regulatory elements such as promoters, enhancers, and polyadenylation signals for use in controlling transcription can be derived from mammalian, microbial, viral, or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

Methods of Use

The fusion polypeptides disclosed herein are useful as an effective agent for activating an immune response and/or inhibiting immunosuppression and fibrosis. For example, the disclosed fusion polypeptides are an effective anti-pathogen (e.g., antiviral) therapy that induces a unique gene expression profile downstream of an IL-2 receptor or IL-15 receptor that is not achieved by its single components or the combination, which leads to new, advantageous pharmacological properties. These novel multi-functional proteins can simultaneously activate several immune system mechanisms and signaling pathways that act in synergy to effectively eliminate intracellular pathogens (e.g., a virus, mycobacterium, etc.). At the cellular level, the immunotherapy platform activates a panoply of lymphoid cells (e.g., T cells, B cells, NK cells, NK-T cells, etc.) and indirectly prime antigen-presenting cells (e.g., dendritic cells and macrophages) due to, in part, GM-CSF induction triggering the cascade of specific immunological reactions against intracellular pathogens. At the molecular level, the fusion proteins disclosed herein activate key transcription factors and signaling molecules crucial to potentiate innate and adaptive immune responses. The fusion polypeptides described herein target and synchronize various arms of the immune system against an intracellular pathogen.

Accordingly, disclosed herein are methods of treating or ameliorating a pathogenic infection (e.g., an intracellular pathogen infection) in a subject, comprising administering a fusion polypeptide comprising: an interleukin (IL) polypeptide; a first TGFβ superfamily receptor polypeptide; and a second TGFβ superfamily receptor polypeptide. Also provided, in an aspect, are methods of treating a pathogenic infection (e.g., an intracellular pathogen infection) in a subject, comprising administering a fusion polypeptide comprising: an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ. Treating or ameliorating a pathogenic infection in a subject can also treat and/or reduce fibrosis associated with the infection of the pathogen. Additionally provided are methods of treating or ameliorating fibrosis associated with or resulting from a pathogenic infection (e.g., an intracellular pathogen infection) in a subject, comprising administering a fusion polypeptide comprising: an interleukin (IL) polypeptide; a first TGFβ superfamily receptor polypeptide; and a second TGFβ superfamily receptor polypeptide.

In some embodiments, TGFβ signaling associated with or resulting from a intracellular pathogen infection leads to pro-fibrotic signaling and/or fibrosis. Accordingly, also provided are methods of reducing or inhibiting fibrosis in an individual, the method comprising administering to the individual a therapeutically effective amount of a fusion polypeptide comprising: (a) an interleukin (IL) polypeptide; (b) a first TGFβ superfamily receptor polypeptide; and (c) a second TGFβ superfamily receptor polypeptide. Further provided are methods of reducing or inhibiting fibrosis resulting from an intracellular pathogen infection in an individual, the method comprising administering to the individual a therapeutically effective amount of a fusion polypeptide comprising: (a) an interleukin (IL) polypeptide; (b) a first TGFβ superfamily receptor polypeptide; and (c) a second TGFβ superfamily receptor polypeptide.

Further provided, are methods of neutralizing or inhibiting an intracellular pathogen in an individual having a pathogenic infection (e.g., an intracellular pathogen infection), comprising administering to the individual a fusion polypeptide comprising: an interleukin (IL) polypeptide; a first TGFβ superfamily receptor polypeptide; and a second TGFβ superfamily receptor polypeptide; thereby neutralizing or inhibiting the pathogen in the individual. Additionally provided are, methods of neutralizing or inhibiting an intracellular pathogen in an individual having a pathogenic infection (e.g., an intracellular pathogen infection), comprising administering to the individual a fusion polypeptide comprising: an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, thereby neutralizing or inhibiting the pathogen in the individual. Neutralizing or inhibiting a pathogenic infection (e.g., an intracellular pathogen infection) in a subject can also treat and/or reduce fibrosis associated with the infection of the pathogen. Additionally provided are methods of reducing or inhibiting fibrosis associated with or resulting from a pathogenic infection (e.g., an intracellular pathogen infection) in a subject, comprising administering a fusion polypeptide comprising: an interleukin (IL) polypeptide; a first TGFβ superfamily receptor polypeptide; and a second TGFβ superfamily receptor polypeptide.

In another aspect, also provided are methods of activating an anti-pathogen immune response cell comprising, contacting an immune cell with a fusion polypeptide comprising: an interleukin (IL) polypeptide; a first TGFβ superfamily receptor polypeptide; and a second TGFβ superfamily receptor polypeptide. Also provided are methods of activating an anti-intracellular pathogen immune response cell comprising, contacting an immune cell with a fusion polypeptide comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ.

In some embodiments, the IL polypeptide comprises an IL-2 polypeptide or IL-15. In some embodiments, the IL polypeptide comprises an IL-2 polypeptide. In some embodiments, the IL-2 polypeptide comprises SEQ ID NO: 2. In some embodiments, the IL-2 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 2. In some embodiments, the IL-2 polypeptide consists of SEQ ID NO: 2. In some embodiments, the IL-2 polypeptide comprises SEQ ID NO: 3. In some embodiments, the IL-2 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 3. In some embodiments, the IL-2 polypeptide consists of SEQ ID NO: 3. In some embodiments, the IL-2 polypeptide comprises SEQ ID NO: 3 In some embodiments, the IL-2 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 3. In some embodiments, the IL-2 polypeptide consists of SEQ ID NO: 3

IL-15 and IL-2 are known to share the same receptor subunits IL-2R beta and IL-2R gamma, leading to similar signaling properties (e.g., cellular responses) in lymphocytes. In some embodiments, the IL polypeptide comprises an IL-15 polypeptide. In some embodiments, the IL-15 polypeptide comprises SEQ ID NO: 5. In some embodiments, the IL-15 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 5. In some embodiments, the IL-15 polypeptide consists of SEQ ID NO: 5. In some embodiments, the IL polypeptide comprises an IL-15 polypeptide. In some embodiments, the IL-15 polypeptide comprises SEQ ID NO: 4. In some embodiments, the IL-15 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 4. In some embodiments, the IL-15 polypeptide consists of SEQ ID NO: 4

In some embodiments, the first TGFβ superfamily receptor polypeptide and/or the second TGFβ superfamily receptor polypeptide comprises an activin receptor polypeptide or fragment thereof, a bone morphogenetic protein (BMP) receptor polypeptide or fragment thereof, a glial cell-derived neurotrophic factor (GDNF) receptor polypeptide or fragment thereof, or a TGFβ receptor II polypeptide or fragment thereof. In some embodiments, the first TGFβ superfamily receptor polypeptide and/or the second TGFβ superfamily receptor polypeptide comprises a TGFβ receptor II (TβRII) polypeptide or fragment thereof.

In some embodiments, the first TGFβ superfamily receptor polypeptide and/or the second TGFβ superfamily receptor polypeptide comprises a soluble TGFβ receptor II (TβRII) polypeptide or fragment thereof. In some embodiments, the first TGFβ superfamily receptor polypeptide and/or the second TGFβ superfamily receptor polypeptide comprises a soluble TGFβ receptor II (TβRII) polypeptide comprising SEQ ID NO: 8, SEQ ID NO: 9, or a combination thereof. In some embodiments, the first TGFβ superfamily receptor polypeptide comprises an amino acid sequence of SEQ ID NO: 8 and the second TGFβ superfamily receptor polypeptide comprises a truncation of an amino acid sequence of SEQ ID NO: 9. In some embodiments, the soluble TGFβ receptor II polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 8 or SEQ ID NO: 9

In some embodiments, the first TGFβ superfamily receptor polypeptide and/or the second TGFβ superfamily receptor polypeptide binds a TGF-β1 polypeptide, a TGF-β2 polypeptide, a TGF-β3 polypeptide, a activin βA polypeptide, a activin βB polypeptide, a activin βC polypeptide, a activin βE polypeptide, a bone morphogenic protein (BMP) 2 polypeptide, a BMP 3 polypeptide, a BMP4 polypeptide, a BMP 5 polypeptide, a BMP 6 polypeptide, a BMP 7 polypeptide, a BMP 8 polypeptide, a BMP 9 polypeptide, a BMP 10 polypeptide, a BMP 11 polypeptide, a BMP 12 polypeptide, a BMP 13 polypeptide, a BMP 14 polypeptide, a BMP 15 polypeptide, a growth differentiation factor (GDF) 1 polypeptide, a GDF 3 polypeptide, a GDF 8 polypeptide, a GDF 9 polypeptide, a GDF 15 polypeptide, a Nodal polypeptide, a Inhibin α polypeptide, an anti-Mullerian Hormone polypeptide, a Lefty 1 polypeptide, a Lefty 2 polypeptide, an arteman polypeptide, a Persephin polypeptide, or a Neurturin polypeptide. In some embodiments, the first TGFβ superfamily receptor polypeptide and/or the second TGFβ superfamily receptor polypeptide binds a TGFβ1 polypeptide, a TGFβ2 polypeptide, a TGFβ3 polypeptide, or any combination thereof. In some embodiments, the first TGFβ superfamily receptor polypeptide and the second TGFβ superfamily receptor polypeptide binds a TGFβ1 polypeptide. In some embodiments, the truncated TGFβ superfamily receptor polypeptide comprises an N terminus truncation, a C terminus truncation, or combination thereof. In some embodiments, the truncated TGFβ superfamily receptor polypeptide is a truncated soluble TGFβ receptor II (sTβRII) polypeptide.

In some embodiments, the truncation comprises greater than 2, greater than 5, greater than 7, greater than 10, greater than 15, greater than 20, greater than 25, or greater than 30 amino acids. In some embodiments, the IL polypeptide comprises a truncated IL polypeptide. In some embodiments, the truncated IL polypeptide comprises an N terminus truncation, a C terminus truncation, or a combination thereof. In some embodiments, the truncated IL polypeptide comprises a truncated IL-2 polypeptide or IL-15 polypeptide. In some embodiments, the fusion polypeptide further comprises a linker polypeptide or a linker molecule attaching the first TGFβ superfamily receptor polypeptide and the second TGFβ superfamily receptor polypeptide.

In some embodiments, the fusion polypeptide further comprises a linker polypeptide fusing the IL polypeptide and the first TGFβ superfamily receptor polypeptide. In some embodiments, the fusion polypeptide further comprises a pharmacokinetic (PK) modulator. In some embodiments, the pharmacokinetic modulator comprises an immunoglobulin constant (Fc) region polypeptide. In some embodiments, the immunoglobulin Fc region polypeptide is a human immunoglobulin Fc region polypeptide. In some embodiments, the immunoglobulin Fc region is an IgG Fc region. In some embodiments, the IgG Fc region is an IgG1, IgG2, IgG3, or IgG4 Fc region. In some embodiments, the PK modulator comprises an albumin polypeptide. In some embodiments, the albumin polypeptide is a human albumin polypeptide.

In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to any one of SEQ ID NOs: 10-25. In some embodiments, the fusion polypeptide comprises an amino acid sequence of SEQ ID NO: 10. In some embodiments, the fusion polypeptide comprises an amino acid sequence of SEQ ID NO: 11. In some embodiments, the fusion polypeptide comprises an amino acid sequence of SEQ ID NO: 12. In some embodiments, the fusion polypeptide comprises an amino acid sequence of SEQ ID NO: 13. In some embodiments, the fusion polypeptide comprises an amino acid sequence of SEQ ID NO: 14. In some embodiments, the fusion polypeptide comprises an amino acid sequence of SEQ ID NO: 15. In some embodiments, the fusion polypeptide comprises an amino acid sequence of SEQ ID NO: 16. In some embodiments, the fusion polypeptide comprises an amino acid sequence of SEQ ID NO:

17. In some embodiments, the fusion polypeptide comprises an amino acid sequence of SEQ ID NO: 18. In some embodiments, the fusion polypeptide comprises an amino acid sequence of SEQ ID NO: 19. In some embodiments, the fusion polypeptide comprises an amino acid sequence of SEQ ID NO: 20. In some embodiments, the fusion polypeptide comprises an amino acid sequence of SEQ ID NO: 21. In some embodiments, the fusion polypeptide comprises an amino acid sequence of SEQ ID NO: 22. In some embodiments, the fusion polypeptide comprises an amino acid sequence of SEQ ID NO: 23. In some embodiments, the fusion polypeptide comprises an amino acid sequence of SEQ ID NO: 24. In some embodiments, the fusion polypeptide comprises an amino acid sequence of SEQ ID NO: 25. In some embodiments, the fusion polypeptide consists of any one of SEQ ID NOs: 10-25.

In some embodiments, the fusion polypeptide activates target cells expressing an IL-2 or IL-15 receptor. In some embodiments, the target cell is an immune cell. In some embodiments, the immune cell is a T cells, natural killer cells NKT cells, B cells, or gamma delta T cells.

In some instances, target cells comprise a type of cell, cell population, or composition of cells which are the desired cells to be collected, isolated, or separated by the present disclosure. Target cells represent cells that various procedures described herein require or are designed to purify, collect, engineer, etc. What the specific cells are depends on the context in which the term is used. For example, if the objective of a procedure is to isolate a particular kind of stem cell, that cell would be the target cell of the procedure. In certain instances, target cells and desired cells are interchangeable and have the same meaning regarding the present disclosure. Target cells can exist in a genus-species relationship. For example, if target cells comprise leukocytes, the target cells would include T cells.

The methods disclosed herein are particularly useful for or comprise the activation of immune cells. In some stances, immune cells generally comprise cells of the immune system. Immune cells are derived from myeloid or lymphoid cell linages. Generally, the methods disclosed herein are directed towards, but not limited to, the activation of immune effector cells. In some instances, immune effector cell comprises a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes. In certain embodiments, T cells, NK cells, B cells, NKT cells and gamma/delta T cells or a combination thereof are activated by the fusion polypeptide.

An immune effector function or an immune effector response encompasses and/or comprises, in some instances, a function or response of an immune effector cell that enhances or promotes an immune attack to a target cell. E.g., an immune effector function or response refers to a property of T cells or NK cells that promotes killing or the inhibition of growth or proliferation, of a target cell. Immune effector function includes direct cytotoxicity, cytokine release, chemokine release, phagocytosis, or other immune function that primes or perpetuates an immune response. In some instances, effector function comprises a specialized function of a cell. Effector function of a T cell, for example, may be cytolytic activity or helper activity including the secretion of cytokines.

The methods disclosed herein are particularly useful for or comprise the activation of myeloid-derived immune cells. Myeloid cells encompass terminally differentiated cells of the myeloid lineage. These cells include neutrophils, eosinophils and monocytes/macrophages, myeloid dendritic cells. In one embodiment of any aspect of the present disclosure, the myeloid cell is a neutrophil, eosinophil, or monocyte/macrophage/dendritic cells. In certain instances, macrophage and/or macrophage-like cells generally comprise macrophages, monocytes, and cells of macrophage/monocyte lineage, and any other similar cells which perform the functions generally associated with macrophages, such as phagocytosis or antigen presentation to other classes of immune cells such as T-cells and B-cells in order to sensitize these cells to a particular target, including but not limited to pathogenic organisms or particles (e.g. viruses, bacterial cells, etc.).

The methods disclosed herein are particularly useful for or comprise the activation of lymphocyte immune cells. In some instances, lymphocytes include natural killer (NK) cells, T cells, or B cells. NK cells are a type of cytotoxic (cell toxic) lymphocyte that represent a major component of the inherent immune system. NK cells kill cells infected by intracellular pathogens. In some embodiments, the natural killer (NK) cells comprise cells of the immune system that kill target cells in the absence of a specific antigenic stimulus, and without restriction according to MHC class. Target cells may be pathogens or cells harboring pathogens. NK cells are characterized by the presence of CD56 and the absence of CD3 surface markers. In some embodiments, T cells comprise a subset of lymphocytic cells that express a surface marker of "CD3" (T-cell receptor). Unless otherwise indicated, T cells include CD4$^+$ (e.g., T-helper cells) and CD8$^+$ (e.g., cytotoxic killer cells).

The fusion polypeptides provided herein are useful for inhibiting, preventing, or reducing immunosuppression. Accordingly, treating or a treatment, in some embodiments, comprises activating immune effector cells that target a pathogen or pathogen infected cell and/or reducing the activation of immunosuppressive cells (e.g., Treg cells and M2 macrophages that are immunosuppressive macrophages and can be associated with immunosuppressive or immunodeficient disease state) and/or myeloid-derived suppressor cells (MDSCs). The methods provided herein are also useful for the suppression or reduction of immunosuppressive immune cells such as T regulatory cells. In some instances, immunosuppressive cells comprise Tregs or regulatory T cells. Tregs comprise CD4+CD25+FOxP3+ T cells that suppress CD4+CD25− and CD8+ T cell proliferation and/or effector function, or that otherwise down-modulate an immune response. Notably, Tregs may down-regulate immune responses mediated by CD8 T cells, Natural Killer cells, Natural Killer T cells as well as other immune cells. Further encompassed, in some embodiments, is the blockade or prevention of immunosuppressive cell differentiation or activation.

In some embodiments, the pathogenic infection is an intracellular bacterial infection. In certain instances, an intracellular bacterial infection comprises the invasion of the host organism by pathogenic bacteria. In certain instances, this includes the excessive growth of bacteria which are normally present in or on the body of the organism, but more generally, a bacterial infection is any situation in which the presence of a bacterial population(s) is damaging to a host organism. Thus, for example, an organism suffers from an intracellular bacterial infection when excessive numbers of a bacterial population are present in or on the organism's body, or when the effects of the presence of a bacterial population(s) is damaging to the cells, tissue, or organs of the organism. In some instances, bacteria refers to a domain of prokaryotic organisms. Bacteria include at least 11 distinct groups as follows: (1) Gram-positive (gram+) bacteria, of which there are two major subdivisions: (i) high G+C group (Actinomycetes, Mycobacteria, *Micrococcus*, others) (ii) low G+C group (Bacillus, Clostridia, Lactobacillus, Staphylococci, Streptococci, Mycoplasmas); (2) Proteobacteria, e.g., Purple photosynthetic and non-photosynthetic Gram-negative bacteria (includes most common Gram-negative bacteria); (3) Cyanobacteria, e.g., oxygenic phototrophs; (4) Spirochetes and related species; (5) Planctomyces; (6) Bacteroides, Flavobacteria; (7) Chlamydia; (8) Green sulfur bacteria; (9) Green non-sulfur bacteria (also anaerobic phototrophs); (10) Radioresistant micrococci and relatives; (11) Thermotoga and Thermosipho thermophiles. Gram-negative bacteria include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*. Gram-positive bacteria include cocci, nonsporulating rods, and sporulating rods. The genera of Gram-positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*. In some instances, pathogenic bacteria are bacterial species that cause disease(s) in another host organism (e.g., animals and plants) by directly infecting the other organism, or by producing agents that causes disease(s) in another organism (e.g., bacteria that produce pathogenic toxins and the like).

In some embodiments, the intracellular bacterial infection is an infection by the genera *Shigella, Campylobacter, Salmonella, Clostridium, Escherichia, Chlamydiae, Rickettssiaceae, Coxiella, Mycobacteriaceae*, and combinations thereof. In some embodiments, the intracellular bacteria is drug resistant. In some embodiments, the intracellular bacterium is gram negative. In some embodiments, the intracellular bacterium is gram positive.

In some embodiments, the pathogenic infection is a viral infection. In some instances, a viral infection comprises an infection caused by one or more viruses. In some embodiments, the virus is an RNA virus. In some embodiments, the virus in a DNA virus. In some embodiments, the viral infection comprises a virus from the family denoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. In some embodiments, viruses include, without limitations to Polioviruses, Coronaviridae and Coronaviruses, Rhinovirus (all subtypes), Adenoviruses (all subtypes), Hepatitis A, Hepatitis B, Hepatitis C, Hepatitis D, Human papillomavirus (including all subtypes), Rabies viruses, Human T-cell lympotropic virus (all subtypes), Rubella virus, Mumps virus, Coxsackie virus A (all subtypes), Coxsackie virus B (all subtypes), human enteroviruses, herpesviruses including cytomegalovirus, Epstein-Barr virus, human herpesviruses (all subtypes), herpes simplex virus, varicella zoster virus, human immunodeficiency virus (HIV) (all subtypes), Epstein-Barr virus, Reoviruses (all subtypes), Filoviruses including Marburg virus and Ebola virus (all stains), Arenaviruses including Lymphocytic choriomeningitis virus, Lassa virus, Junin virus, and Machupo virus, Arboviruses including West Nile virus, Dengue viruses (all serotypes), Zika virus, Colorado tick fever virus, Sindbis virus, Togaviraidae, Flaviviridae, Bunyaviridae, Reoviridae, Rhabdoviridae, Orthomyxoviridae, Poxviruses including orthopoxvirus (variola virus, monkeypox virus, vaccinia virus, cowpox virus), yatapoxviruses (tanapox virus, Yaba monkey tumor virus), parapoxvirus, molluscipoxvirus, Yellow fever, Hantaviruses including Hantaan, Seoul, Dobrava, Sin Nombre, Puumala, and Dobrava-like Saaremaa, human para influenza viruses and influenza viruses (all types), HINI influenza and swine influenza viruses, respiratory syncytial virus (all subgroups), rotaviruses including human rotaviruses A-E, bovine rotavirus, rhesus monkey rotavirus, Polyomaviruses including simian virus 40, JC virus, BK virus, Coltiviruses, eyach virus, calciviruses, and Parvoviridae including dependovirus, parvovirus and erythrovirus. In some embodiments, the viral infection comprises coronavirus. In some embodiments, the viral infection comprises SARS-COV-2. In some embodiments, the viral infection comprises influenza.

Accordingly, the compositions provided herein are useful in methods for treating a pathogenic infection (e.g., an intracellular pathogen infection). Thus, provided herein are uses of a fusion polypeptide of the disclosure comprising an interleukin (IL) polypeptide, a first TGFβ superfamily receptor polypeptide, and a second TGFβ superfamily receptor polypeptide, in a method of neutralizing or inhibiting a virus and/or progression in an individual having a viral infection. Also provided herein are uses of a fusion polypeptide of the disclosure comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, in a method of neutralizing or inhibiting a virus and/or progression in an individual having a viral infection.

Further provided herein are uses of a fusion polypeptide of the disclosure comprising an interleukin (IL) polypeptide, a first TGFβ superfamily receptor polypeptide, and a second TGFβ superfamily receptor polypeptide, in a method of neutralizing or inhibiting an intracellular bacterium and/or progression in an individual having a bacterial infection. Also provided herein are uses of a fusion polypeptide of the disclosure comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, in a method of neutralizing or inhibiting an intracellular bacterium and/or progression in an individual having a bacterial infection.

Provided herein are fusion polypeptides comprising an interleukin (IL) polypeptide, a first TGFβ superfamily receptor polypeptide, and a second TGFβ superfamily receptor polypeptide, for use in a method of neutralizing or inhibiting a virus and/or progression in an individual having a viral infection. Also provided herein are fusion polypeptides comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, for use in a method of neutralizing or inhibiting a virus and/or progression in an individual having a viral infection.

Further provided herein are fusion polypeptides comprising an interleukin (IL) polypeptide, a first TGFβ superfamily receptor polypeptide, and a second TGFβ superfamily receptor polypeptide, for use in a method of neutralizing or inhibiting an intracellular bacterium and/or progression in an individual having a bacterial infection. Also provided herein are fusion polypeptides comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, for use in a method of neutralizing or inhibiting an intracellular bacterium and/or progression in an individual having a bacterial infection.

In certain embodiments, the fusion proteins can be administered to a subject in need thereof by any route suitable for the administration of fusion protein-containing pharmaceutical compositions, such as, for example, subcutaneous, intraperitoneal, intravenous, intramuscular, or intracerebral, etc. In certain embodiments, the fusion proteins are administered intravenously. In certain embodiments, the fusion proteins are administered subcutaneously. In certain embodiments, the fusion proteins are administered intravenously. In certain embodiments, the fusion proteins are administered on a suitable dosage schedule, for example, weekly, twice weekly, monthly, twice monthly, once every two weeks, once every three weeks, or once a month etc. In certain embodiments, the fusion proteins are administered once every three weeks. The fusion proteins can be administered in any therapeutically effective amount. In certain embodiments, the therapeutically acceptable amount is from about 0.1 mg/kg to about 50 mg/kg. In certain embodiments, the therapeutically acceptable amount is from about 1 mg/kg to about 40 mg/kg. In certain embodiments, the therapeutically acceptable amount is from about 5 mg/kg to about 30 mg/kg. Therapeutically effective amounts include amounts that are sufficient to ameliorate one or more symptoms associated with the disease or affliction to be treated.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying, or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The term "a therapeutically effective amount" of a compound of the present application refers to an amount of the compound of the present application that elicits the biological or medical response of a subject, for example, reduction or inhibition of a pathogen infection, or ameliorate symptoms, alleviate conditions, slow or delay disease progression, or prevent a disease, etc. In one non-limiting embodiment, the term "a therapeutically effective amount" refers to the amount of a compound of the present application that, when administered to a subject, is effective to at least partially alleviate, inhibit, prevent, and/or ameliorate a condition, or a disorder or a disease, or at least partially inhibit activity of a targeted enzyme or receptor.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining", "measuring", "evaluating", "assessing", "assaying", and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject", "individual", or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. In some embodiments, the subject may be diagnosed with a pathogen or pathogenic infection or suspected of being at high risk for a pathogen infection.

The term "in vivo" is used to describe an event that takes place in a subject's body. The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay. The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

As used herein, the term "about" a number refers to that number plus or minus 10% of that number. The term "about" a range refers to that range minus 10% of its lowest value and plus 10% of its greatest value.

The section headings used herein are for organizational purposes only and are not to be construed as limiting the subject matter described.

EXAMPLES

The following examples are included for illustrative purposes only and are not intended to limit the scope of the disclosure.

Example 1—Improved IL-2 Activation of Immune Cells

Exemplifying the fusion polypeptide compositions and methods disclosed herein, the following example demonstrates that the fusion polypeptides comprising an interleukin-2 (IL-2) polypeptide, a first sTBRII receptor polypeptide, and a second sTBRII receptor polypeptide (bFIST) induces higher levels of IFN-gamma and CXCL10 in human NK cells as compared to fusion proteins comprising an IL-2 polypeptide and single sTBRII receptor polypeptide (monovalent FIST).

Figure 1B:
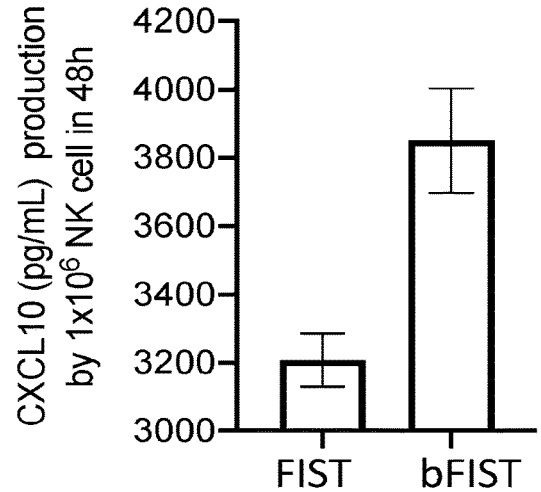

Human T cells and NK cells were isolated from PBMC by negative selection and were stimulated with FIST (IL2-sTBRII, monovalent) or a FIST variant with bivalent sTBRII traps (IL2-sTBRII-sTBRII) for 48 hours. After 48 hours of incubation, the conditioned media were collected to quantify the levels of IFNγ from T cells and CXCL10 from NK cells by ELISA. As shown in the data of FIGS. 1A-1B, bFIST demonstrates significantly higher IL-2 receptor activation than FIST (monovalent FIST).

Example 2—Improved TGFβ1 Binding

Exemplifying the fusion polypeptide compositions and methods disclosed herein, the following example demonstrates that the fusion polypeptides comprising an interleukin-2 (IL-2) polypeptide, a first sTBRII receptor polypeptide, and a second sTBRII receptor polypeptide (bFIST) more effectively bind active TGFβ1 as compared to fusion proteins comprising an IL-2 polypeptide and single sTBRII receptor polypeptide (monovalent FIST).

Figure 2:
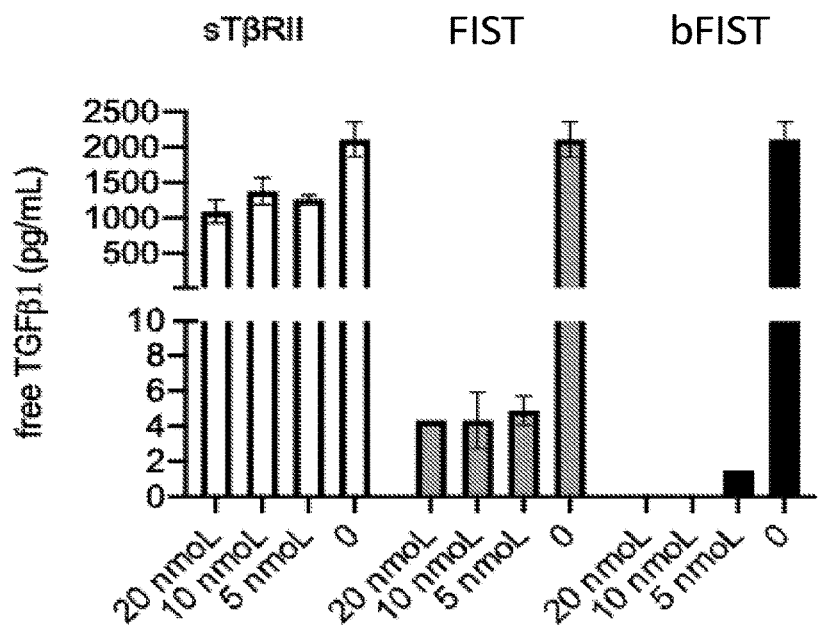
FIG. 2 shows data depicting the quantification of active TGFβ1 detected in solution after 30 minutes incubation period with 5-20 nanomoles of human monovalent FIST (monovalent FIST), bivalent FIST (bFIST), or sTBRII.

Human active TGFβ1 (2 ng/mL) previously activated with 4 mM HCl containing 0.1% of bovine serum albumin (BSA) was incubated with sTBRII control, FIST (monovalent FIST) or bFIST (5-20 nmoL) for 30 minutes at RT and free active TGFβ in solution was quantified by ELISA (ELISA for human TGFβ1 immunoassay).

bFIST effectively blocks active TGFβ1 in solution at significant lower concentrations than sTBRII as illustrated in that FIG. 2. These results indicate that IL-2 as part of the fusion protein also modifies the sTBRII portion and its binding properties to active TGFβ. Furthermore, the bivalent sTBRII trap variant has more effective TGFβ blocking activity.

Example 3—Blockage of TGFβ Isoforms in Solution

Exemplifying the fusion polypeptide compositions and methods disclosed herein, the following example demonstrates that the fusion polypeptides comprising an interleukin-2 (IL-2) polypeptide, a first sTBRII receptor polypeptide, and a second sTBRII receptor polypeptide more effectively binds TGFβ isoforms.

The blocking activity of TGFβ isoforms in solution by bFISTv3, FIST, or control (TβRII isoform 2) was determined by incubating bFISTv3, FIST, or control with 1 ng/ml of active TGF β isoforms. Equimolar concentrations (range of $5\text{-}5\times10^{-6}$ nmoL) of bFISTv3, FIST or control (TβRII isoform 2) were compared in their ability to block active TGFβ isoforms in solution. bFISTv3, FIST or control were incubated with 1 ng/ml of active TGFβ isoforms diluted in phosphate buffered saline (PBS) for 30 minutes and the free TGFβ (unblocked) was quantified by ELISAs specific for each TGFβ isoforms.

Figure 4A:
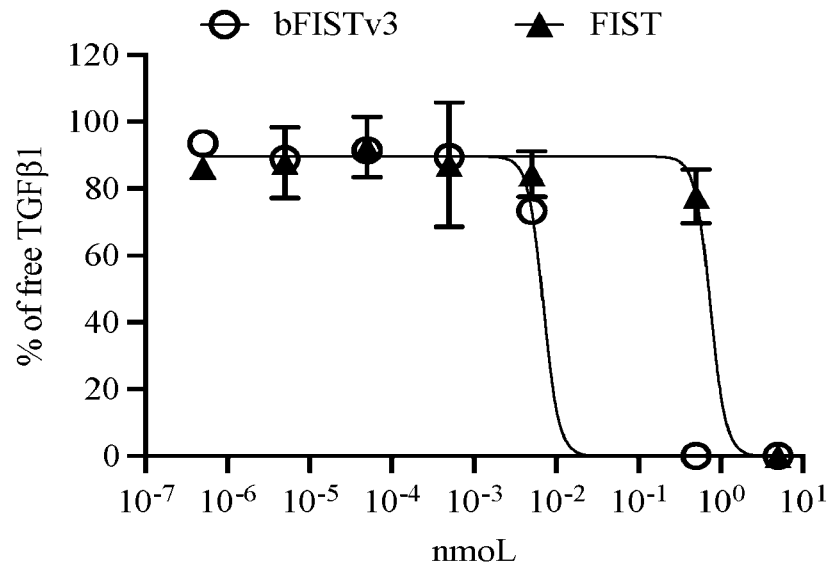
FIGS. 4A, 4B, and 4C show comparison between bivalent FIST protein and monovalent FIST in the blockage of TGFβ isoforms.
Figure 4B:
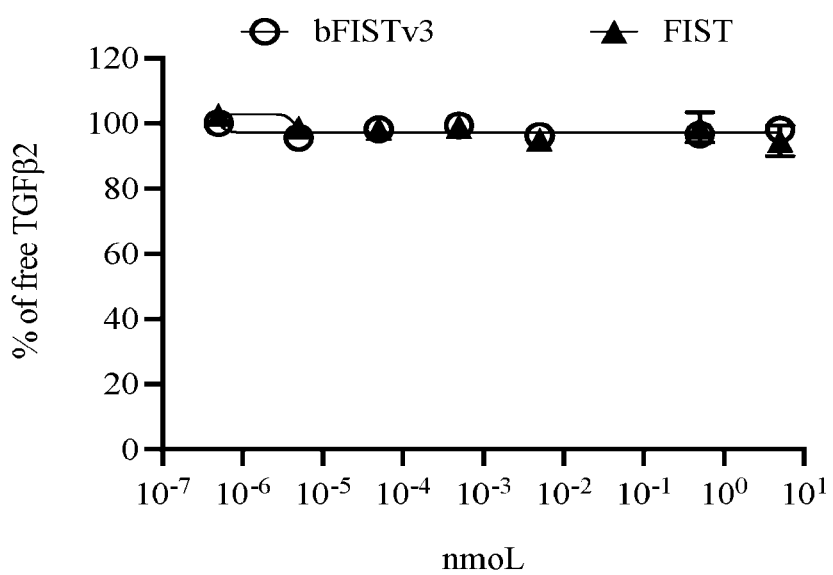
Figure 4C:
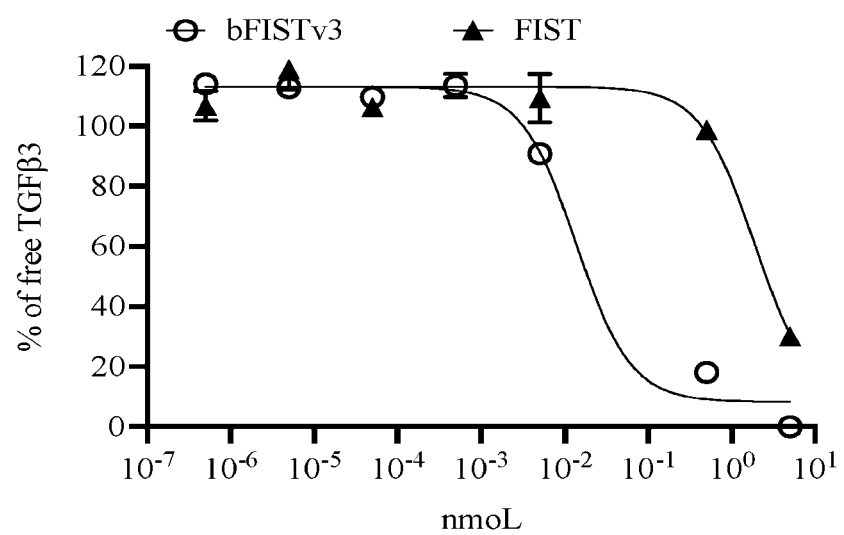

TGFβ causes a wide range of immune suppression in several immune cell types including inhibition of crucial early innate IFN responses. Defective IFN immune responses enhance the severity of viral infections often followed by secondary bacterial infections, scarring, fibrosis, and loss of lung functions. bFISTv3 demonstrated a significantly increased affinity with picomolar potency for TGFβ1 (9 picomoles) and TGFβ3 (70 picomoles) compared to FIST and the control TβRII isoform 2 (FIG. 4A-C). FIG. 4A shows blocking of the TGFβ1 binding. FIG. 4B shows blocking of the TGFβ2 binding. FIG. 4C shows blocking of the TGFβ3 binding. Table 1 shows binding values for TGFβ blocking activity in solution.

TGFβ1 and TGFβ3 isoforms are known as inducers of fibrotic diseases. In contrast, TGFβ2 was not blocked by the fusion protein or control. TGFβ2 is an important regulator of hematopoiesis, cardiovascular function and glucose and fatty acid metabolism.

TABLE 1

| IC50 values for active TGFβ blocking activity in solution | | | |
|---|---|---|---|
| Molecule | TGFβ1 | TGFβ2 | TGFβ3 |
| TβRII (isoform II) | 0.02 nM | NA | 0.26 nM |
| FIST | 1.29 nM | NA | 3.6 nM |
| bFISTv3 | 0.009 nM | NA | 0.07 nM |

Example 4—Inhibition of TGFβ1-Mediated Suppression of CTLL-2 Proliferation

Exemplifying the fusion polypeptide compositions and methods disclosed herein, the following example demonstrates that the fusion polypeptides comprising an interleukin-2 (IL-2) polypeptide, a sTβRII receptor polypeptide, and a second sTβRII receptor polypeptide more effectively induces CTLL-2 (cytotoxic T cell line) proliferation and prevents the TGFβ1-mediated suppression.

Figure 5A:
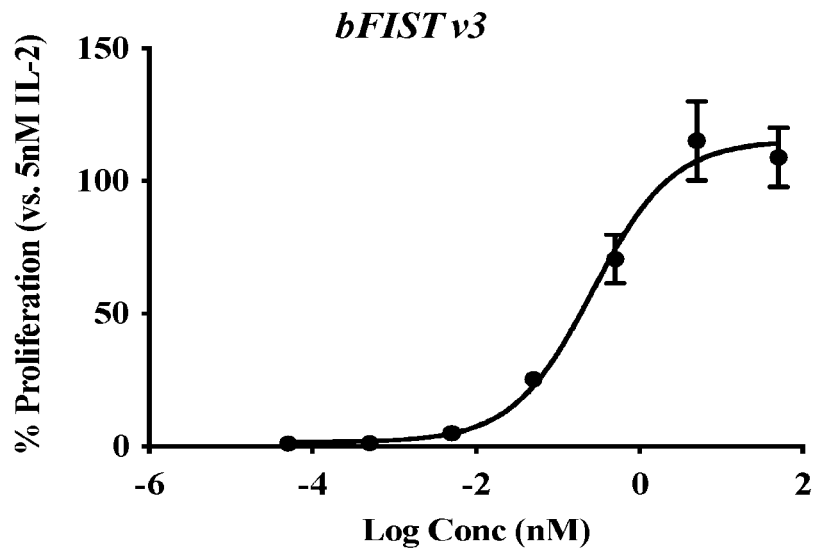
FIGS. 5A, 5B, 5C, 5D, 5E, and 5F show inhibition of TGFβ1-mediated suppression of cytotoxic T cell proliferation.
Figure 5B:
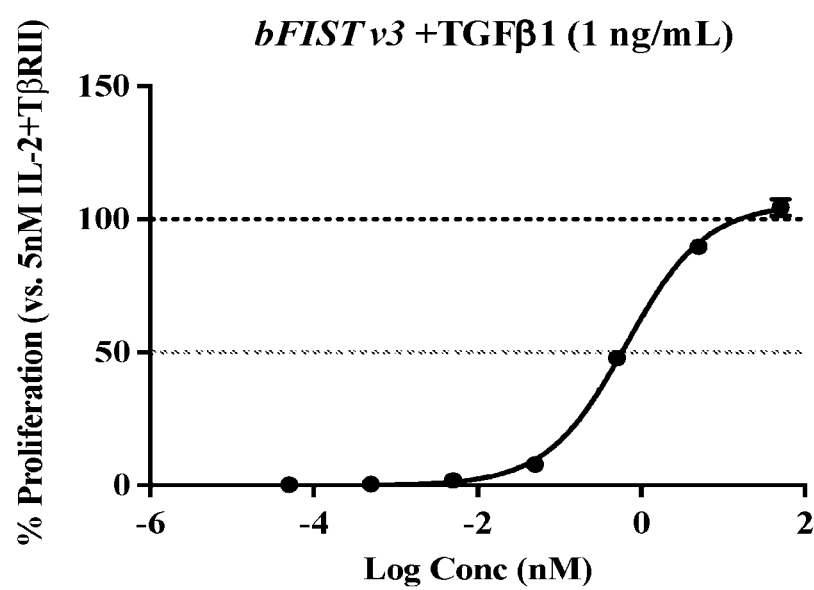
Figure 5C:
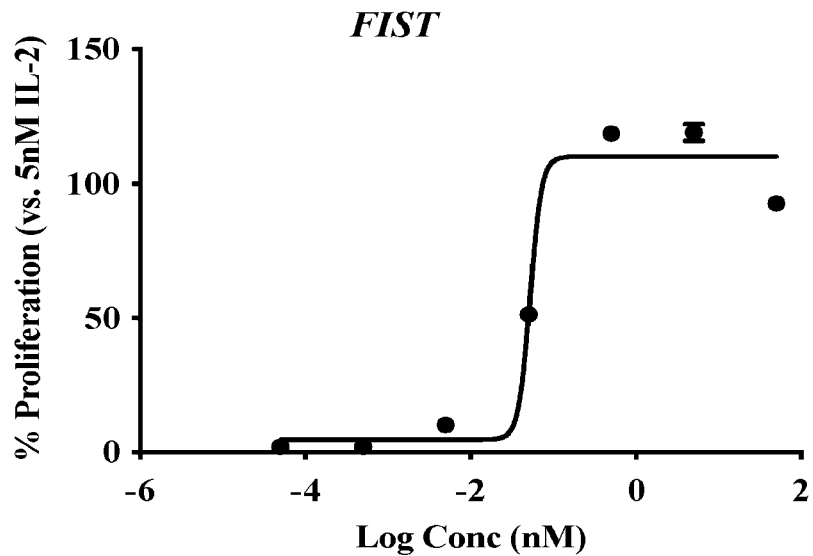
Figure 5D:
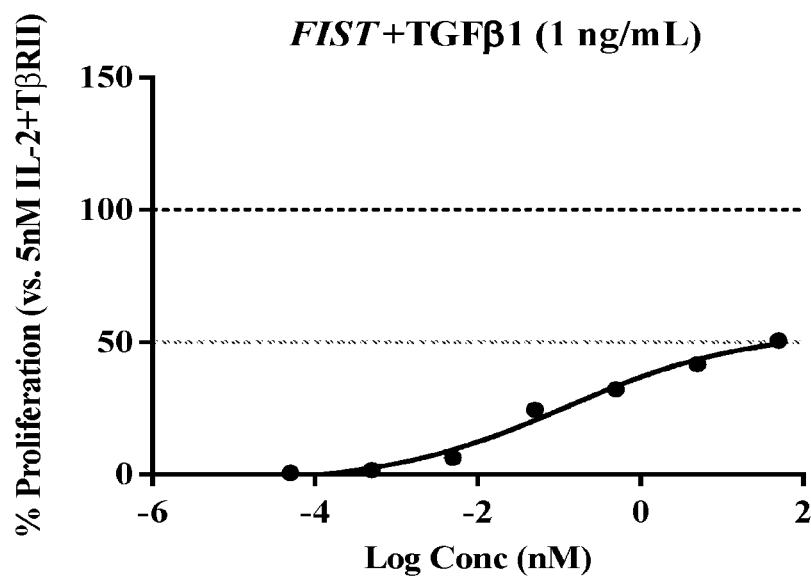
Figure 5E:
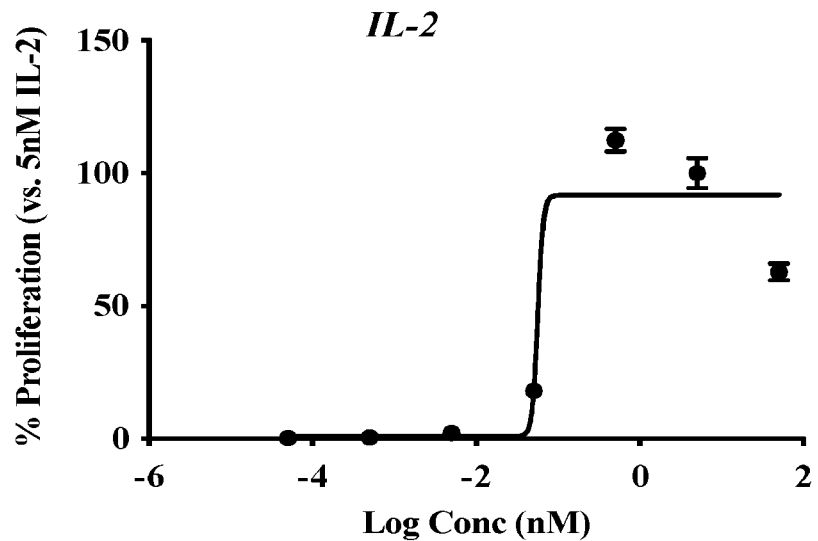
Figure 5F:
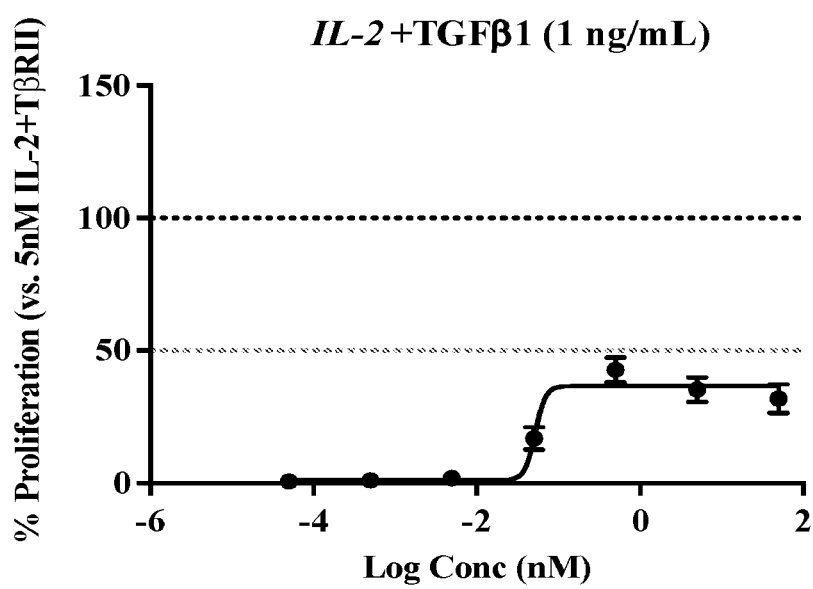

Equimolar concentrations (range of $50\text{-}5\times10^{-5}$ nmoL) of bFISTv3, FIST or controls (IL-2 and TβRII isoform 2) were compared in their ability to inhibit active TGFβ1-mediated suppression of CTLL-2 proliferation. CTLL-2 cells ($5\times10^3$ cells/well) were stimulated with equimolar concentration of bFISTv3, FIST or controls for 72 hours at 37° C. with/without active TGFβ1 (1 ng/mL). After the incubation period, cell proliferation was determined by a luminescent cell viability assay. The absolute IC50 was determined with a dose-response curve using nonlinear regression model with a sigmoidal dose response. The surviving rate (%)= $(\text{Lum}_{Test\ article}-\text{Lum}_{Medium\ control})/(\text{Lum}_{vehicle\ control}-\text{Lum}_{Medium\ control})\times 100\%$. The cell number was quantified by a luminescence signal versus cell dose curve.

bFISTv3 induces CTLL-2 cell proliferation and prevents the TGFβ1-mediated suppression of CTLL-2 proliferation more effectively than FIST (monovalent FIST). TGFβ suppresses T-cell responses by inhibiting T-cell proliferation and inducing T-cell death, thus limiting T-cell expansion after activation. TGFβ1 is known to inhibit IL-2 signaling and the proliferation of T cells through multiple pathways. TGFβ1 inhibits the phosphorylation and activation of components of the JAK/STAT cascade downstream of IL-2R, as well as exerts inhibitory activity at the nuclear level on a subset of IL-2 target genes including c-Myc, cyclin D2, and cyclin. FIG. 5A: Proliferation of CTLL-2 stimulated with bFISTv3. FIG. 5B: Proliferation of CTLL-2 stimulated with bFISTv3 in the presence of active TGFβ1 (1 ng/ml). FIG. 5C: Proliferation of CTLL-2 stimulated with FIST (monovalent FIST). FIG. 5D: Proliferation of CTLL-2 stimulated with FIST in the presence of active TGFβ1 (1 ng/ml). FIG. 5E: Proliferation of CTLL-2 stimulated with IL-2. FIG. 5F: Proliferation of CTLL-2 stimulated IL-2 in the presence of active TGFβ1 (1 ng/mL). Data are shown as mean±SD, **p<0.005.

TABLE 2

IC50 values for CTLL-2 cell proliferation in response to the stimuli of fusion proteins or controls

| Molecule | IC50 | top | bottom | slope |
|---|---|---|---|---|
| IL-2 | 0.057 | 106 | 1.04 | ~12 |
| IL2 + TβBRII | 0.131 | 116 | 1.26 | 1.6 |
| FIST | 0.063 | 121 | 3.8 | 1.56 |
| bFISTv3 | 0.459 | 137 | 0.07 | 0.69 |

TABLE 3

IC50 values for the inhibition of TGFb1-dependent suppression of CTLL-2 cell proliferation

| Molecule | IC50 | top | bottom | slope |
|---|---|---|---|---|

Example 5—bFIST Proliferation of Effector Memory T Cells and Terminal Differentiated Effector Memory Cells Exemplifying the fusion polypeptide compositions and methods disclosed herein, the following example demonstrates that the fusion polypeptides comprising an interleukin-2 (IL-2) polypeptide, a sTβRII receptor polypeptide, and a second sTβRII receptor polypeptide more effectively induces cytokine production and proliferation of both effector memory ($T_{EM}$) and terminal differentiated effector memory ($T_{EMRA}$) CD8 T cells.

Purified human T cells derived from PBMC-stimulated with CEF peptide pool (lyophilized mixture of 32 peptides from cytomegalovirus, Epstein-Barr virus, and influenza virus) were labeled with CellTrace™ Violet to track T cell proliferation (CellTrace™ mean fluorescence intensity (MFI) decreases as the cell proliferation increases). Proliferation of CD8⁺ T cells, effector memory T cells (CCR7⁻ CD45RA⁻ CD62L⁻ CD8⁺ T cells), and terminal differentiated effector memory CD8 T cells (CCR7⁻ CD45RA⁺ CD62L⁻ CD8⁺ T cells) stimulated with equimolar concentration of bFISTv3, FIST (monovalent FIST), or IL-2.

Human PBMC from healthy donors were stimulated with CEF peptide pool overnight to induce the generation of viral antigen-specific T cells. T cells (CD3⁺) were purified from PBMC derived from healthy donors by immunomagnetic negative selection using a Human T cell isolation kit. Purified T cells were labeled with CellTrace™ Violet before being stimulated with 5 nmoL of bFISTv3, FIST (monovalent FIST) and IL-2 for 48 hours. Stimulated T cells were labeled with fluorescence-conjugated antibodies specific for the memory T cell populations. After the incubation period, cell supernatants were collected to quantify the concentration of IFNγ by ELISA and the cells were collected to determine the cell proliferation of each T cell subpopulation by flow cytometry. bFISTv3 induces IFNγ production from T cells and significantly higher proliferation of both effector memory ($T_{EM}$) and terminal differentiated effector memory ($T_{EMRA}$) CD8 T cells (e.g., when compared to FIST).

Figure 6A:
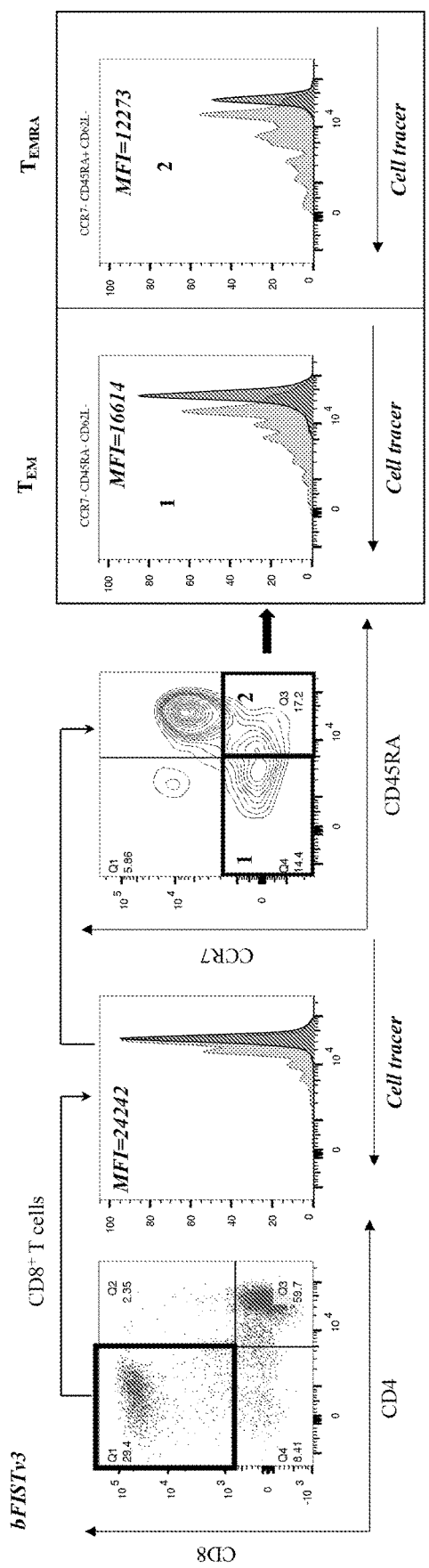
Figure 6B:
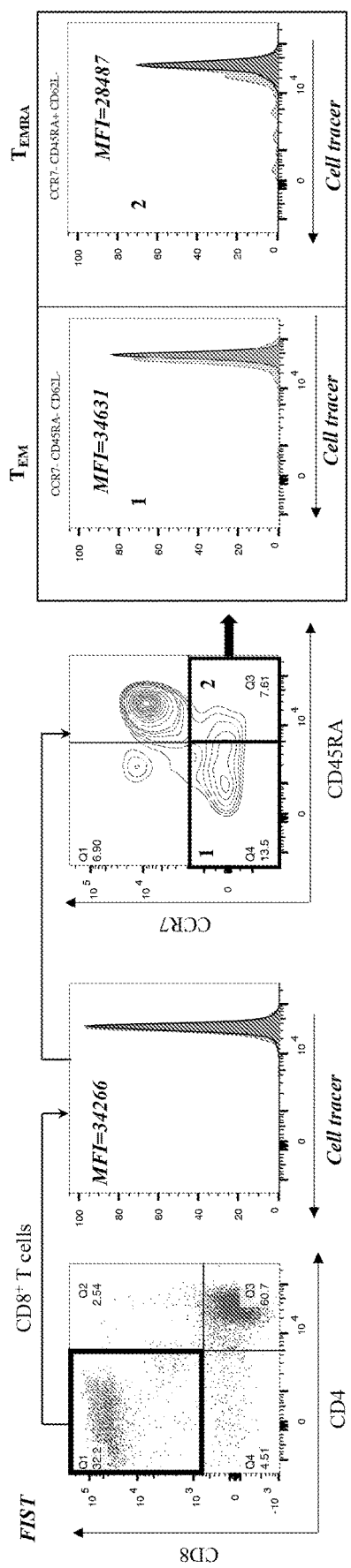
Figure 6C:
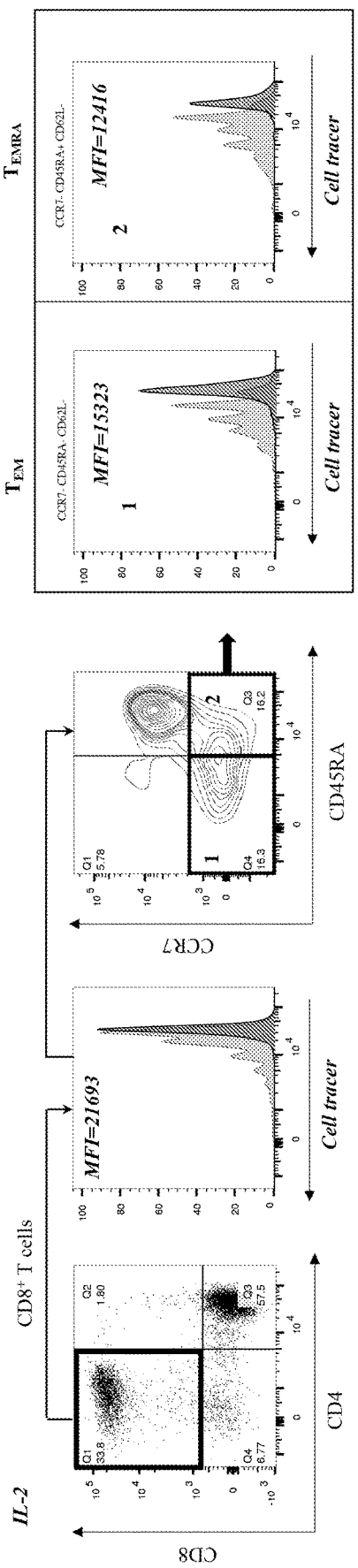
Figure 6F:
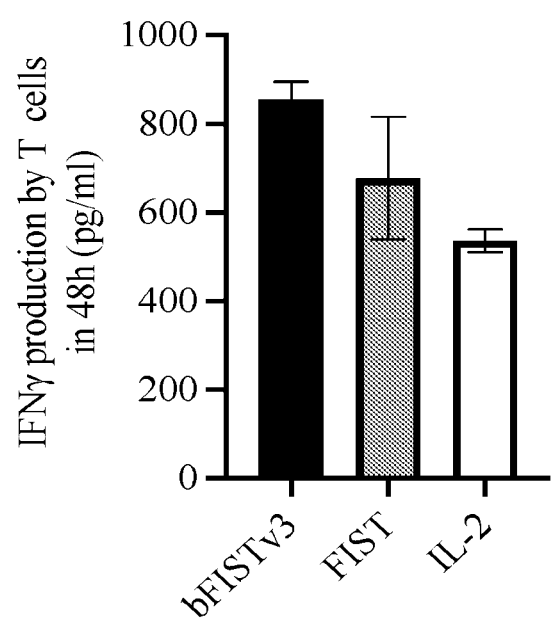

The effector memory T lymphocyte are antigen-primed lymphocytes that can confer rapid immune protection upon a second viral infection. The memory T cell subpopulations CCR7⁻ can migrate to inflame tissues and exert immediate effector functions like cytotoxic activity against virus-infected cells. CCR7⁻ memory CD8⁺ T cells are characterized by the production of IFNγ and perforin-containing granules essential for their cytolytic activity against virus-infected cells. In particular, the perforin expression is prominent in the terminal differentiated effector memory T cells (CD45RA⁺CCR7⁻ CD62L⁻). FIG. 6A shows bFISTv3 induced proliferation of effector memory T cells ($T_{EM}$) and terminal differentiated effector memory cells ($T_{EMRA}$). FIG. 6B shows FIST induced proliferation of effector memory T cells ($T_{EM}$) and terminal differentiated effector memory cells ($T_{EMRA}$). FIG. 6C shows IL-2 induced proliferation of effector memory T cells ($T_{EM}$) and terminal differentiated effector memory cells ($T_{EMRA}$). FIG. 6D shows the average of CellTrace™ MFI values of stimulated $T_{EM}$ derived from two donors (a decrease in MFI denotes increased proliferation). FIG. 6E shows average CellTrace™ MFI values of stimulated $T_{EMRA}$ derived from two donors. FIG. 6F shows quantification of IFNγ production by T cells stimulated with bFISTv3, FIST (monovalent FIST), or IL-2 for 48 hours. Data are shown as mean±SD, * p<0.05.

Example 6—bFIST Reinforces the Th1 Phenotype of TCR-Stimulated T Cells and Enhances the Expression of Anti-Pathogen Cytokines and Proteases Exemplifying the fusion polypeptide compositions and methods disclosed herein, the following example demonstrates that the fusion polypeptides comprising an interleukin-2 (IL-2) polypeptide, a sTβRII receptor polypeptide, and a second sTβRII receptor polypeptide more effectively induces higher production of anti-pathogen cytokines crucial for the adaptive immune response against pathogens.

Figure 7A:
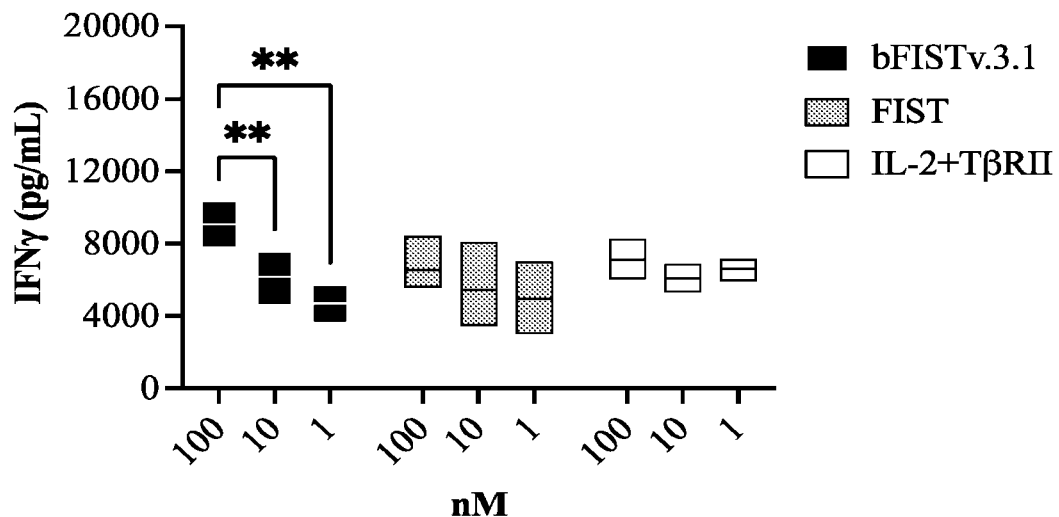
FIGS. 7A, 7B, 7C, 7D, and 7E show that bivalent FIST (bFIST) enhances the expression of anti-pathogen cytokines and proteases.
Figure 7B:
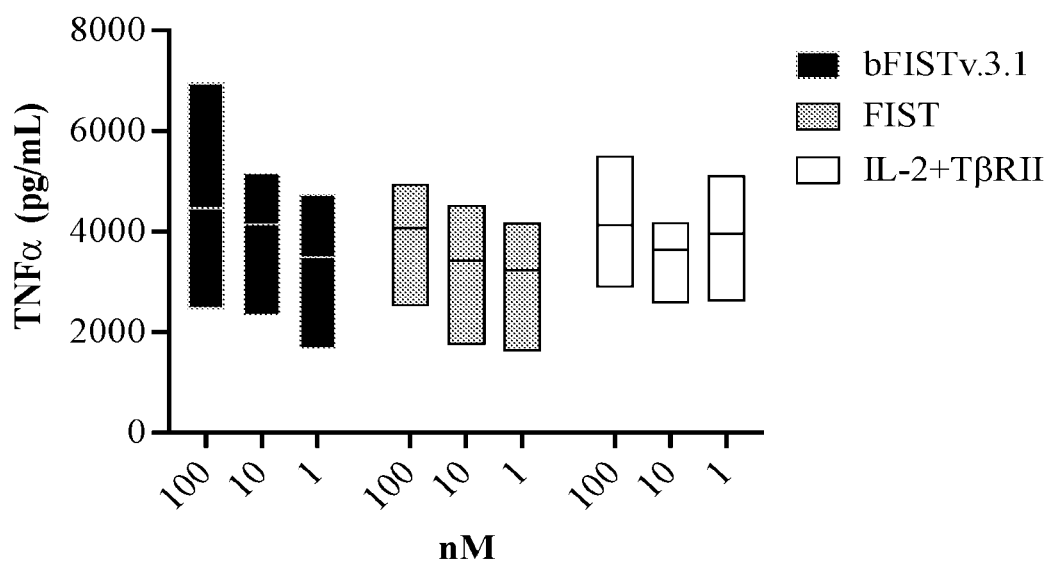
Figure 7C:
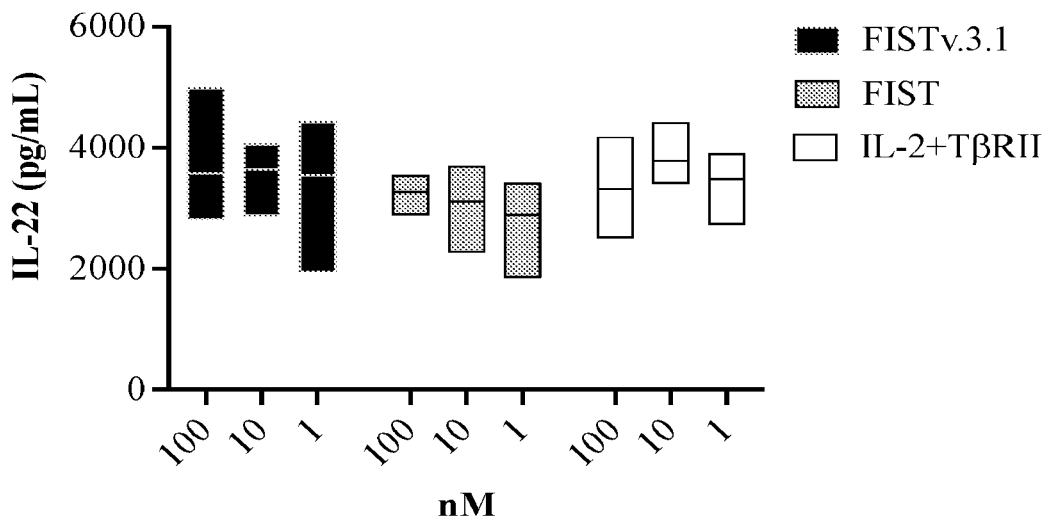
Figure 7D:
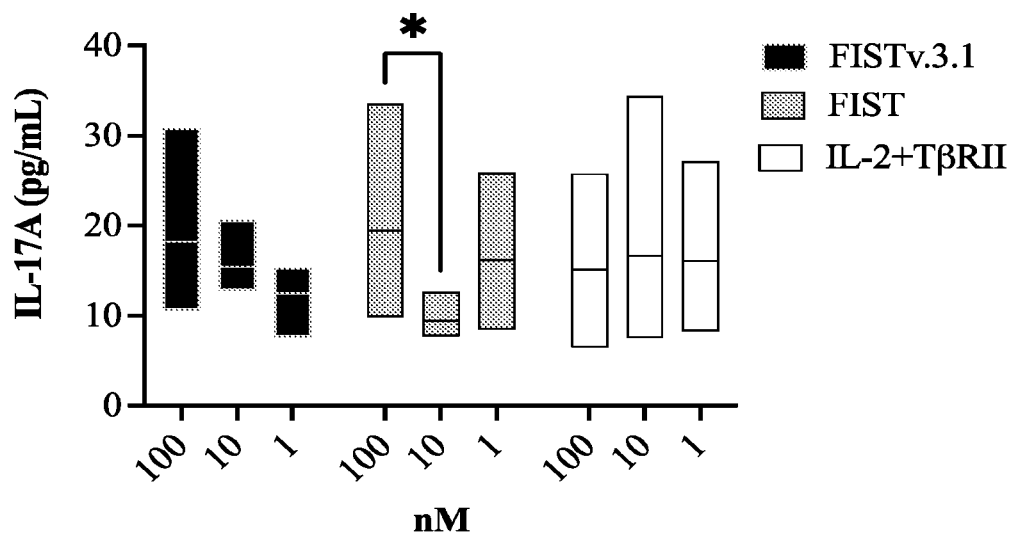
Figure 7E:
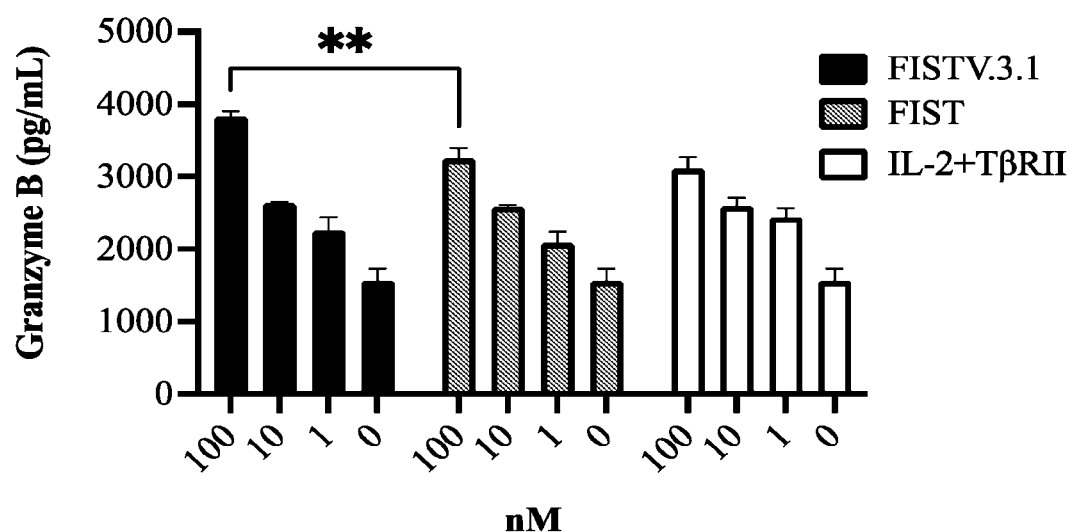

T cells (CD3⁺) were purified from PBMC derived from healthy donors by immunomagnetic negative selection using a Human T cell isolation kit. Purified human T cells were stimulated with anti-CD3/CD28 antibodies and equimolar concentrations of the bivalent FIST (bFISTv.3.1), FIST (monovalent) and IL-2 for 48 hours. After the incubation period, cell supernatants were collected to quantify the concentration of Th polarizing cytokines by a multi-analyte flow assay. The concentration of 8 cytokines (IL-5, IL-13, IL-6, IFNγ, TNFα, IL-17A, IL-4 and IL-22) per sample were determined by flow cytometry. The concentration of granzyme B was quantified by ELISA. FIG. 7A, shows the quantification of IFNγ produced by T cells stimulated with CD3/CD28 and equimolar concentrations of bFISTv3.1, FIST and IL-2+TβRII. FIG. 7B, shows the quantification of TNFα produced by T cells stimulated with CD3/CD28 and equimolar concentrations of bFISTv3.1, FIST and IL-2+TβRII. FIG. 7C, shows the quantification of IL-22 produced by T cells stimulated with CD3/CD28 and equimolar concentrations of bFISTv3.1, FIST and IL-2+TβRII. FIG. 7D, shows the quantification of IL-17A produced by T cells stimulated with CD3/CD28 and equimolar concentrations of bFISTv3.1, FIST and IL-2+TβRII. FIG. 7E, shows the quantification of granzyme B produced by T cells stimulated with CD3/CD28 and equimolar concentrations of bFISTv3.1, FIST and IL-2+TβRII quantified by ELISA. Data are shown as mean±SD, * p<0.05. The bivalent FIST (bFISTv.3.1) induces higher production of IFNγ, TNFα and IL-22 in a concentration dependent manner. In contrast, the monovalent FIST only induced IL-17A in a concentration dependent manner. Regarding to IL-5, IL-13, IL-6 and IL-4, no differences were detected (data not shown). These results demonstrate the superiority of bivalent FIST to reinforce the Th1 phenotype of TCR-stimulated T cells and enhance the effector functions of these cells such as the secretion of serine proteases (granzyme B) that mediate the cytotoxicity against pathogen-infected cells.

Both IFNγ and TNFα are known to control viral infections. IFNγ is crucial in the defense against intracellular pathogens such as mycobacteria and viruses. Similarly, IL-22 and IL-17 play an important role in protective immune responses against intracellular pathogens. IL-22 inhibits the growth of mycobacterium and decrease the number of regulatory T cells, which increase antigen-specific T cell responses. IL-22, IFNγ and IL-17 are adaptive cytokines involved in the development of protective immunity against pathogens.

Example 7—bFIST Prevents TGFβ1-Mediated Suppression of Primary NK Cell Proliferation and Increases IFNγ Production from these Cells Exemplifying the fusion polypeptide compositions and methods disclosed herein, the following example demonstrates that the fusion polypeptides comprising an interleukin-2 (IL-2) polypeptide, a sTβRII receptor polypeptide, and a second sTβRII receptor polypeptide more effectively inhibits and/or reduces TGFβ1-mediated suppression of NK cell proliferation and IFNγ production.

Human NK cells were purified from PBMC derived from healthy donors by immunomagnetic negative selection using a human NK cell isolation kit. Purified NK cells were labeled stimulated with equimolar concentrations (25 nM, 12.5 nM and 6.25 nM) of bFISTv3, FIST (monovalent FIST) and IL-2 for 5 days. After the incubation period, the cell culture supernatant was collected to quantify the concentration of IFNγ by ELISA. The number of viable cells was quantified with the fluorescence-based assay using a cell number/luminescence curve and the percentage of cell proliferation was calculated versus the positive control (IL-2+TβRII) as the maximum stimulus of NK cell proliferation for these experimental conditions.

Figure 8A:
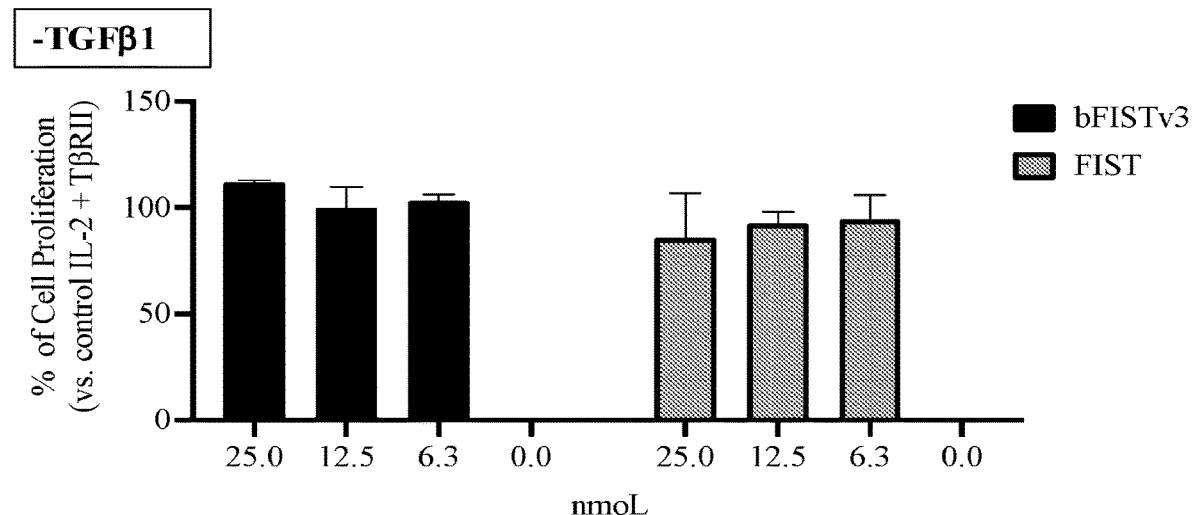
FIGS. 8A, 8B, 8C, 8D, and 8E show bivalent FIST inhibition and/or reduction of TGFβ1-mediated suppression of primary NK cell proliferation and IFNγ and CXC10 production.
Figure 8B:
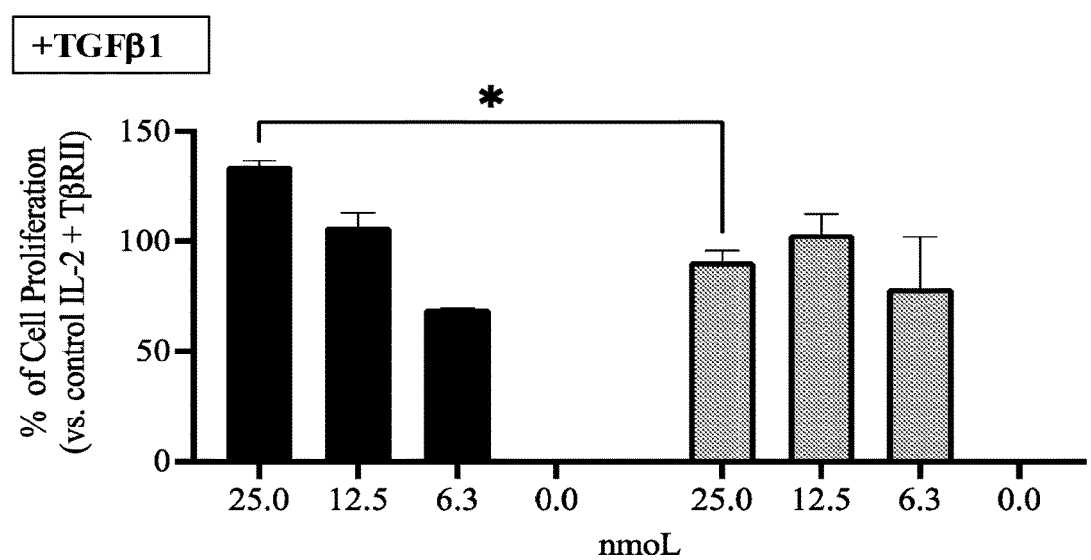
Figure 8C:
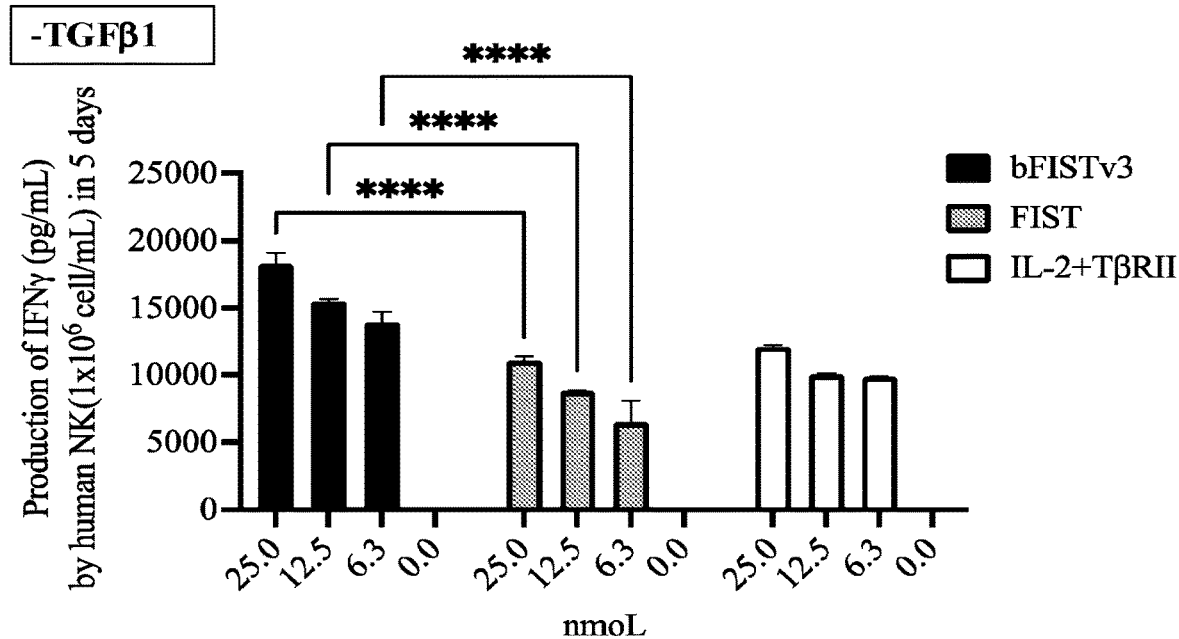
Figure 8D:
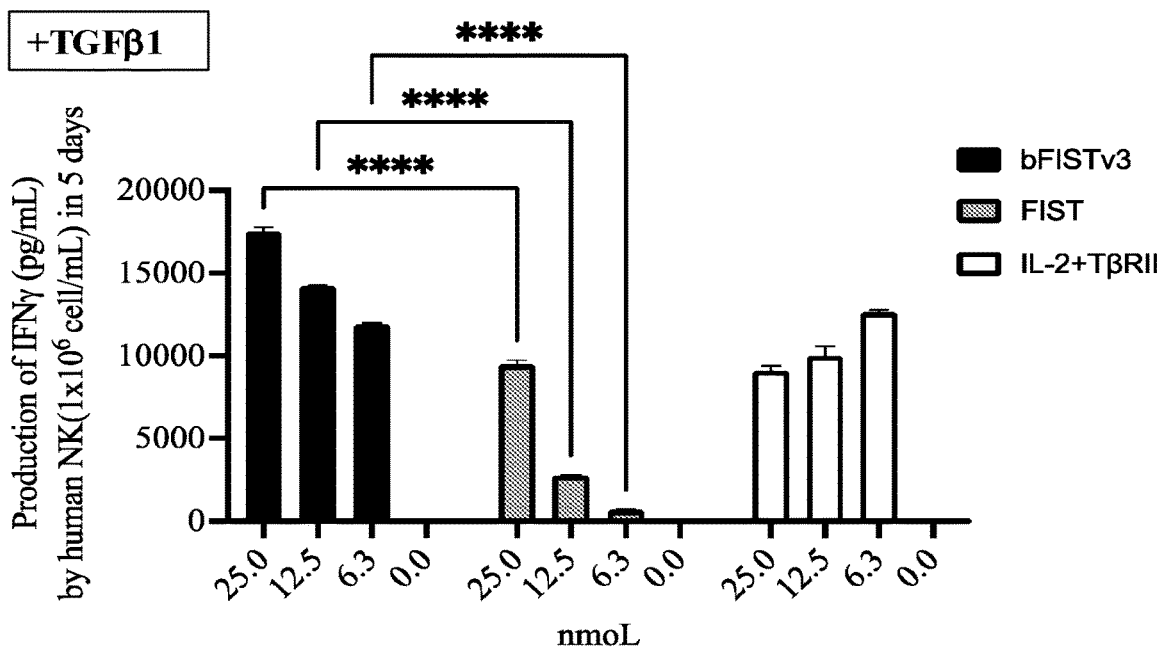
Figure 8E:
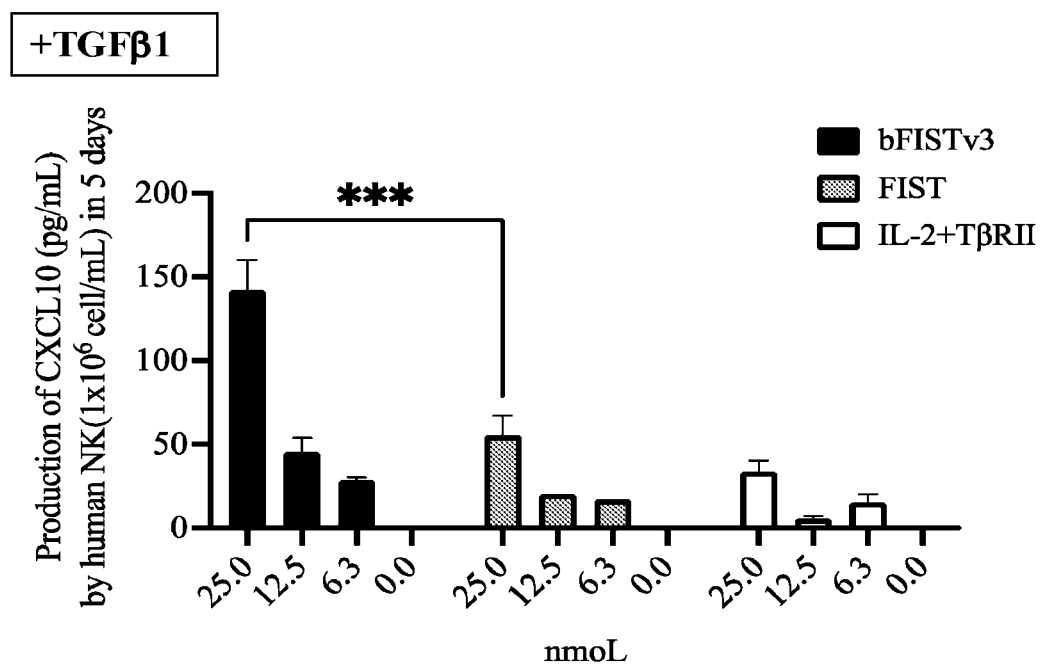

Purified human NK cells derived from peripheral mononuclear cells (PBMC) were stimulated with equimolar concentrations of bFISTv.3, FIST (monovalent FIST) or control (IL-2+TβRII) for 5 days with or without active TGFβ1 (1 ng/mL). The culture supernatant was collected to quantify the amount of IFNγ by ELISA and the number of viable cells in culture was determined by quantitating the amount of ATP present, which indicates the metabolically active cells. FIG. 8A shows the percentage of proliferating NK cells in the absence of active TGFβ1. FIG. 8B shows the percentage of proliferating NK cell in the presence of active TGFβ1. FIG. 8C shows the quantification of IFNγ produced by stimulated NK cells cultured in the absence of active TGFβ1. FIG. 8D, quantification of IFNγ produced by stimulated NK cells cultured with active TGFβ1 (1 ng/mL). CXCL10 mediates the mobilization of NK cells and virus-specific T lymphocytes to the infected tissues and enhances the effector functions of these cells against virus-infected cells. Bivalent FIST (bFISTv.3) effectively induces more CXCL10 production. FIG. 8E, quantification of CXCL10 produced by stimulated NK cells cultured with of active TGFβ1 (1 ng/ml). The data are representative of two independent experiments performed in duplicates. Statistic comparisons between bFISTv3 and FIST are indicated (data are shown as mean±SD, *p<0.05, p<0.005, *p<0.0005).

Example 8—bFIST Stimulates and Increases B Cell Maturation, Proliferation and IFNγ Production Exemplifying the fusion polypeptide compositions and methods disclosed herein, the following example demonstrates that the fusion polypeptides comprising an interleukin-2 (IL-2) polypeptide, a sTβRII receptor polypeptide, and a second sTβRII receptor polypeptide effectively (1) stimulates and/or increases higher B cell maturation, proliferation and IFNγ production and (2) reduces and/or inhibits TGFβ1 suppression of B cell maturation, proliferation and IFNγ production.

Human B cells were purified from PBMC derived from healthy donors by immunomagnetic negative selection using a Human B cell isolation kit. Purified B cells were pre-labeled with CFSE to trace cell proliferation (the marker intensity decreases as the cell proliferation increases) before being stimulated with equimolar concentrations (20 nM, 10 nM and 5 nM) of bFISTv3, FIST and IL-2 for 5 days. After the incubation period, B cells were labeled with CD86 and HLA-DR and the percentages of double positive (CD86$^+$ HLA-DR$^+$) B cells and proliferation were quantified by flow cytometry. The cell culture supernatants were collected to quantify the concentration of IFNγ by ELISA. The statistic comparisons between bFISTv3 and FIST are indicated. Data are shown as mean±SD, *p<0.05, p<0.005, *p<0.0005.

Figure 9A:
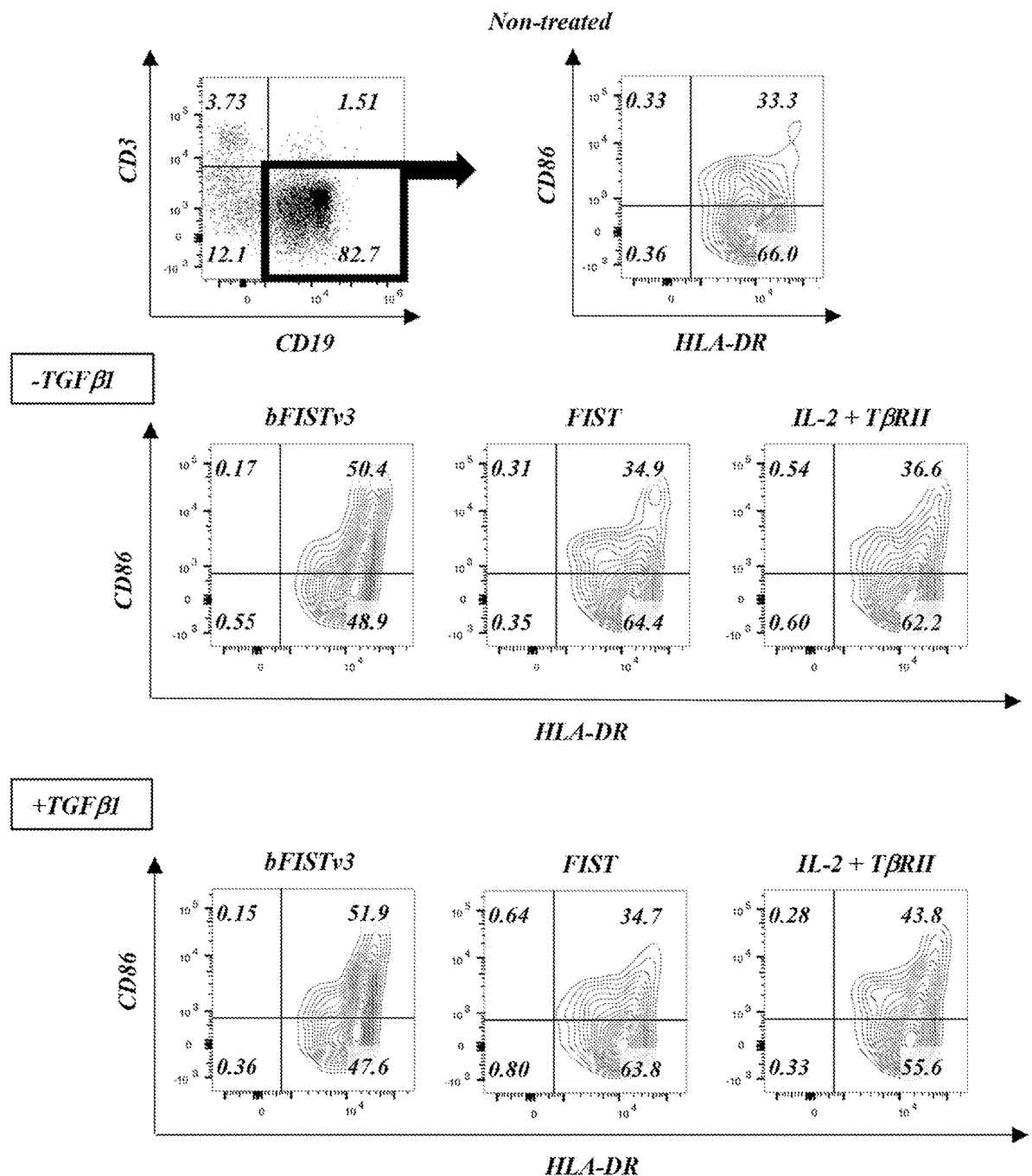
FIGS. 9A, 9B, 9C, and 9D show bivalent FIST (bFIST) more effectively inhibits and/or reduces TGFβ1-mediated suppression of B cell activation, proliferation, and IFNγ production.
Figure 9B:
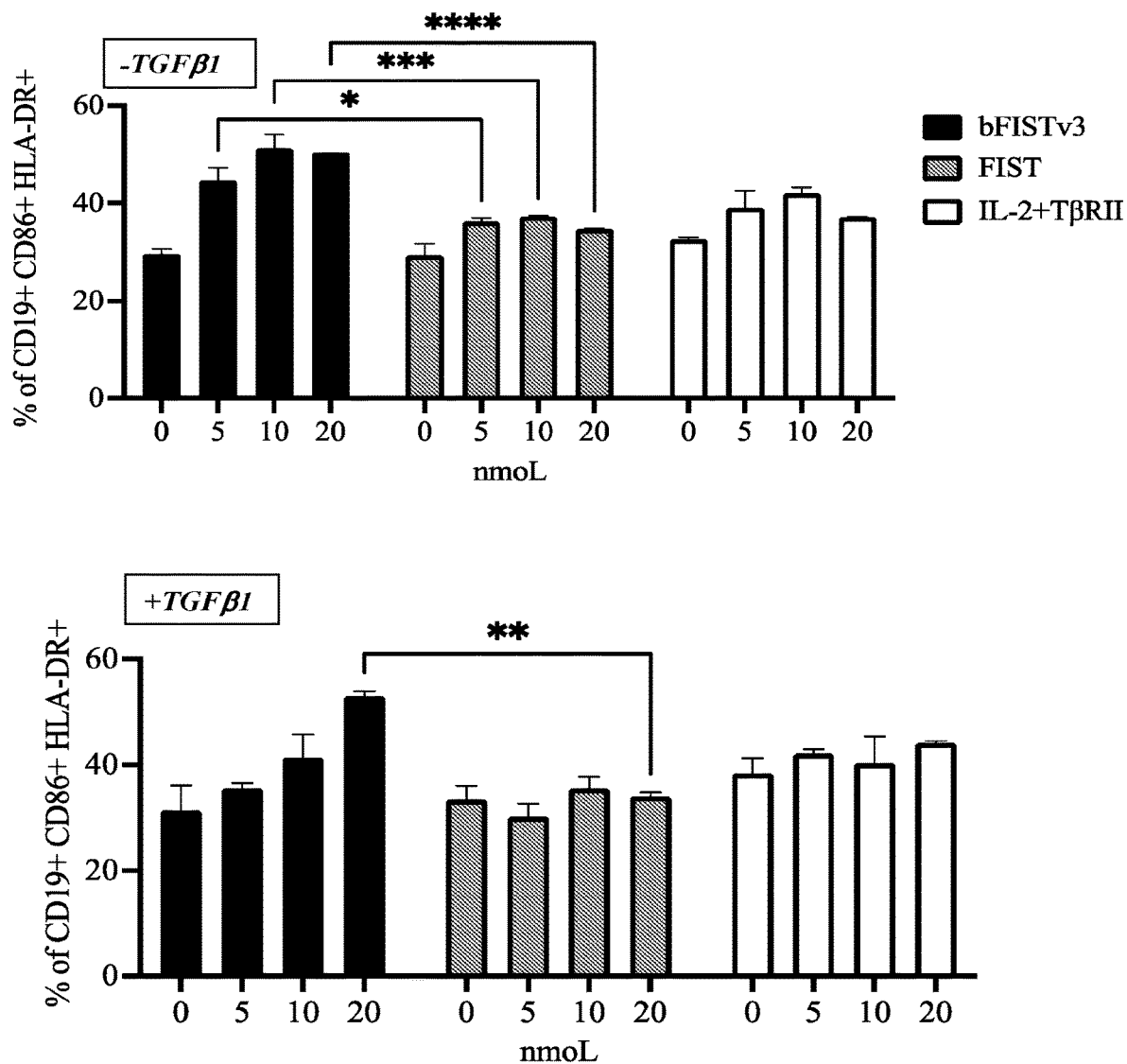
Figure 9C:
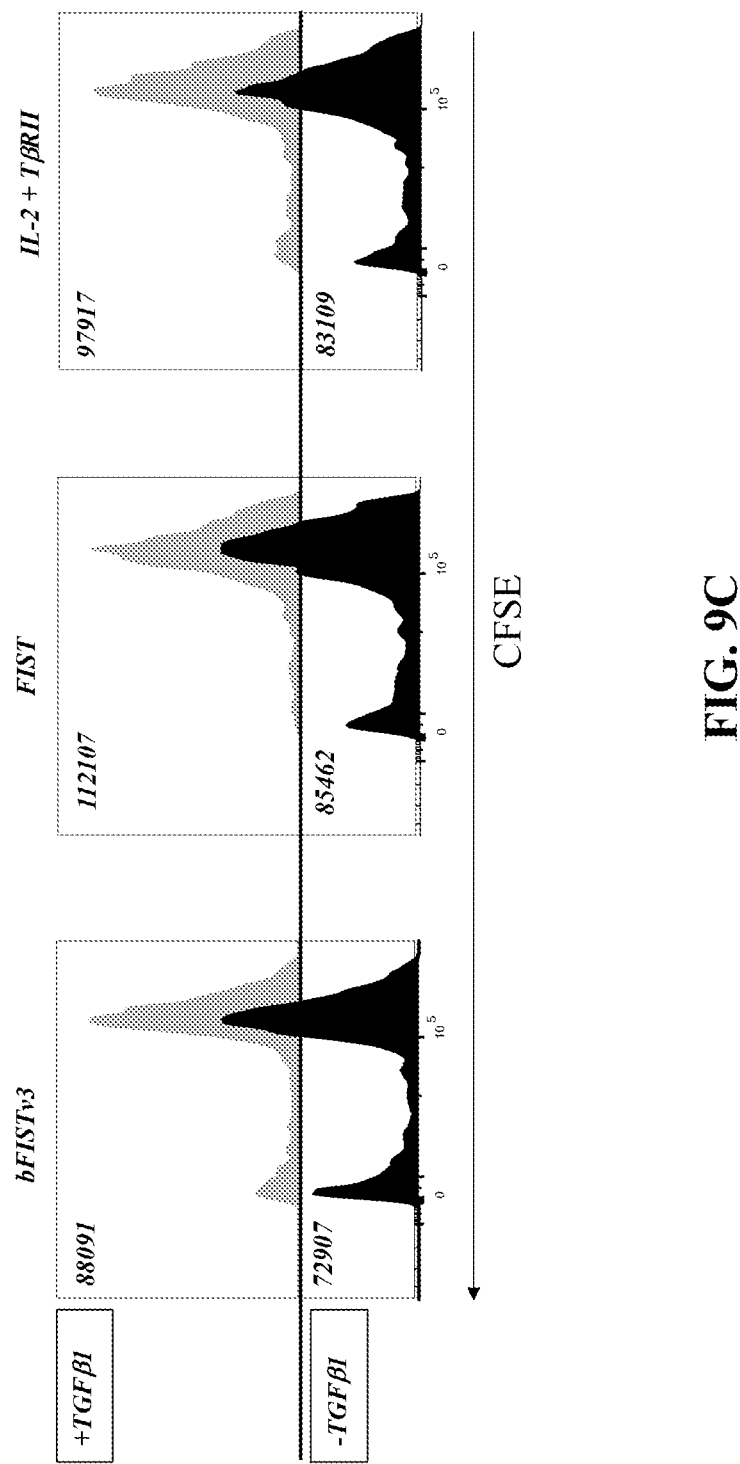
Figure 9D:
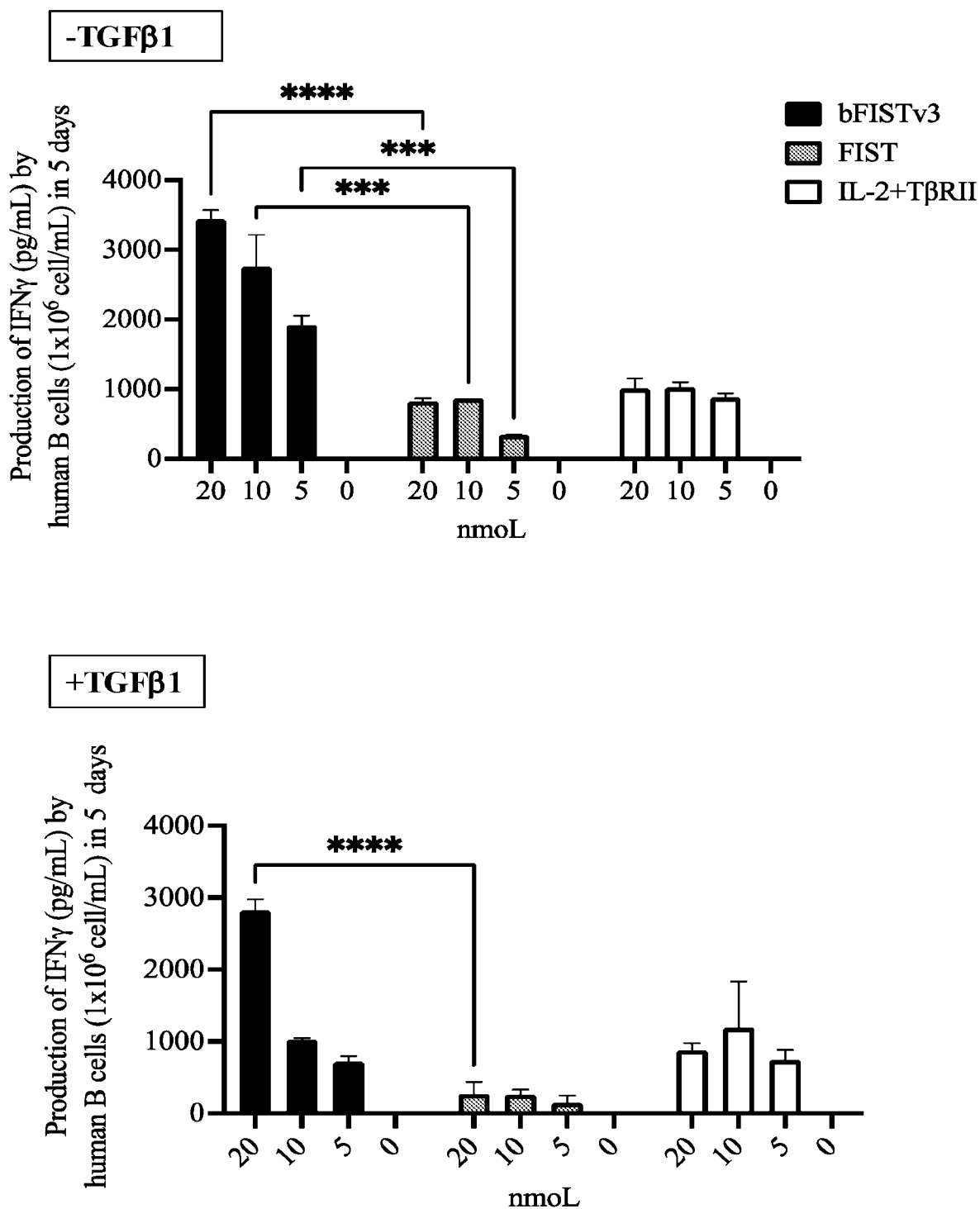

Bivalent FIST (bFISTv.3) more effectively increases and/or stimulates B cell activation, proliferation, and IFNγ production (e.g., compared to FIST or IL-2). Bivalent FIST also induces the upregulation of costimulatory molecule (CD86) and HLA-DR (MHC class II) molecule expression, which indicates a differentiation process of naïve B cells into effector cells with higher capacity for presentation of pathogenic antigens. Both antigen-presenting cells, B cells and dendritic cells contribute to restimulating antigen-specific memory T cells and promote long-term protection against pathogens. FIGS. 9A-D shows data from purified human B cells (CD19$^+$ CD3$^-$) derived from peripheral mononuclear cells (PBMC) were labeled with Carboxyfluorescein succinimidyl ester (CFSE) to trace cell proliferation before being stimulated with equimolar concentrations of bFISTv3, FIST (monovalent FIST) or, control (IL-2+TβRII) for 5 days with and without active TGFβ1 (1 ng/mL). Stimulated B cells were labeled with conjugated antibodies specific for HLA-DR and CD86 to quantify the percentage of mature B cells by flow cytometry. FIG. 9A shows a comparison between bFISTv3 (20 nmoL) and FIST (20 nmoL) in the induction of double positive CD86$^+$HLA-DR$^+$ B cells cultured with/without active TGFβ1. FIG. 9B shows the percentage of CD86$^+$ HLA-DR$^+$ B cells stimulated with 20, 10, 5 nmoL of bFISTv3, FIST (monovalent FIST) or, control (IL-2+TβRII)

cultured with/without active TGFβ1. FIG. 9C shows a comparison between bFISTv3 (20 nmoL) and FIST (20 nmoL) in the induction of CD86+HLA-DR+ B cell proliferation with/without active TGFβ1. The mean fluorescence intensity (MFI) values of CFSE (cell tracer) are indicated. FIG. 9D shows quantification of IFNγ production in the supernatant of stimulated B cells cultured with and without active TGFβ1.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

SEQUENCES

| SEQ ID NO | SEQUENCE | DESCRIPTION |
|---|---|---|
| 1 | MYRMQLLSCIALSLALVTNSAPTSSSTKKTQLQLEHLLLDLQMILNGI NNYKNPKLTRMLTFKFYMPKKATELKHLQCLEEELKPLEEVLNLAQ SKNFHLRPRDLISNINVIVLELKGSETTFMCEYADETATIVEFLNRWIT FCQSIISTLT | Human_IL2 |
| 2 | MYRMQLLSCIALSLALVTNSAPTSSSTKKTQLQLEHLLLDLQMILNGI NNYKNPKLTRMLTFKFYMPKKATELKHLQCLEEELKPLEEVLNLAQ SKNFHLRPRDLISNINVIVLELKGSETTFMCEYADETATIVEFLNRWIT FCQSIISTL | FIST_IL2 |
| 3 | MYRMQLLSCIALSLALVTNSAPTSSSTKKTQLQLEHLLLDLQMILNGI NNYKNPKLTRMLTAKFYMPKKATELKHLQCLEEELKPLEEVLNLAQ SKNFHLRPRDLISNINVIVLELKGSETTFMCEYADETATIVEFLNRWIT FCQSIISTL | FIST_IL2M IL-2 mutated F62A |
| 4 | MVLGTIDLCSCFSAGLPKTEANWVNVISDLKKIEDLIQSMHIDATLYT ESDVHPSCKVTAMKCFLLELQVISLESGDASIHDTVENLIILANNSLSS NGNVTESGCKECEELEEKNIKEFLQSFVHIVQMFINTS | Human_IL15 |
| 5 | CFSAGLPKTEANWVNVISDLKKIEDLIQSMHIDATLYTESDVHPSCK VTAMKCFLLELQVISLESGDASIHDTVENLIILANNSLSSNGNVTESG CKECEELEEKNIKEFLQSFVHIVQMFINTS | FIST_IL15 |
| 6 | MGRGLLRGLWPLHIVLWTRIASTIPPHVQKSVNNDMIVTDNNGAVK FPQLCKFCDVRFSTCDNQKSCMSNCSITSICEKPQEVCVAVWRKNDE NITLETVCHDPKLPYHDFILEDAASPKCIMKEKKKPGETFFMCSCSSD ECNDNIIFSEEYNTSNPDLLLVIFQVTGISLLPPLGVAISVIIIFYCYRVN RQQKLSSTWETGKTRKLMEFSEHCAIILEDDRSDISSTCANNINHNTE LLPIELDTLVGKGRFAEVYKAKLKQNTSEQFETVAVKIFPYEEYASW KTEKDIFSDINLKHENILQFLTAEERKTELGKQYWLITAFHAKGNLQE YLTRHVISWEDLRKLGSSLARGIAHLHSDHTPCGRPKMPIVHRDLKS SNILVKNDLTCCLCDFGLSLRLDPTLSVDDLANSGQVGTARYMAPE VLESRMNLENVESFKQTDVYSMALVLWEMTSRCNAVGEVKDYEPP FGSKVREHPCVESMKDNVLRDRGRPEIPSFWLNHQGIQMVCETLTEC WDHDPEARLTAQCVAERFSELEHLDRLSGRSCSEEKIPEDGSLNTTK | Human TGFBR |
| 7 | MGRGLLRGLWPLHIVLWTRIASTIPPHVQKSDVEMEAQKDEIICPSC NRTAHPLRHINNDMIVTDNNGAVKFPQLCKFCDVRFSTCDNQKSCM SNCSITSICEKPQEVCVAVWRKNDENITLETVCHDPKLPYHDFILEDA ASPKCIMKEKKKPGETFFMCSCSSDECNDNIIFSEEYNTSNPDLLLVIF QVTGISLLPPLGVAISVIIIFYCYRVNRQQKLSSTWETGKTRKLMEFSE HCAIILEDDRSDISSTCANNINHNTELLPIELDTLVGKGRFAEVYKAK LKQNTSEQFETVAVKIFPYEEYASWKTEKDIFSDINLKHENILQFLTA EERKTELGKQYWLITAFHAKGNLQEYLTRHVISWEDLRKLGSSLAR GIAHLHSDHTPCGRPKMPIVHRDLKSSNILVKNDLTCCLCDFGLSLRL DPTLSVDDLANSGQVGTARYMAPEVLESRMNLENVESFKQTDVYS MALVLWEMTSRCNAVGEVKDYEPPFGSKVREHPCVESMKDNVLRD RGRPEIPSFWLNHQGIQMVCETLTECWDHDPEARLTAQCVAERFSEL EHLDRLSGRSCSEEKIPEDGSLNTTK | Human TGFBR long |
| 8 | IPPHVQKSVNNDMIVTDNNGAVKLPQLCKFCDVRFSTCDNQKSCMS NCSITSICEKPHEVCVAVWRKNDENITLETVCHDPKLTYHGFTLEDA ASPKCVMKEKKKPGETFFMCSCSADECNDNIIFSEDYNTSNPD | bFIST_TGFBR_ short |
| 9 | IPPHVQKSDVEMEAQKGEMICVTCNRTAHPLKHVNNDMIVTDNNG AVKLPQLCKFCDVRFSTCDNQKSCMSNCSITSICEKPQEVCVAVWRK NDENITLETVCHDPKLTYHGFTLEDAASPKCVMKEKKKPGETFFMC SCSSDECNDNIIFSEDYNTSNPD | bFIST_TGFBR_ long |
| 10 | MYRMQLLSCIALSLALVTNSAPTSSSTKKTQLQLEHLLLDLQMILNGI NNYKNPKLTRMLTAKFYMPKKATELKHLQCLEEELKPLEEVLNLAQ SKNFHLRPRDLISNINVIVLELKGSETTFMCEYADETATIVEFLNRWIT FCQSIISTLQKSVNNDMIVTDNNGAVKLPQLCKFCDVRFSTCDNQKS | bFISTv.2 |

| SEQ ID NO | SEQUENCE | DESCRIPTION |
|---|---|---|
| | CMSNCSITSICEKPHEVCVAVWRKNDENITLETVCHDPKLTYHGFTL<br>EDAASPKCVMKEKKKPGETFFMCSCSADECNDNIIFIPPHVQKSVNN<br>DMIVTDNNGAVKLPQLCKFCDVRFSTCDNQKSCMSNCSITSICEKPH<br>EVCVAVWRKNDENITLETVCHDPKLTYHGFTLEDAASPKCVMKEK<br>KKPGETFFMCSCSADECNDNIIFSEDYNTSNPD | |
| 11 | MYRMQLLSCIALSLALVTNSAPTSSSTKKTQLQLEHLLLDLQMILNGI<br>NNYKNPKLTRMLTFKFYMPKKATELKHLQCLEEELKPLEEVLNLAQ<br>SKNFHLRPRDLISNINIVLELKGSETTFMCEYADETATIVEFLNRWIT<br>FCQSIISTLIPPHVQKSVNNDMIVTDNNGAVKLPQLCKFCDVRFSTCD<br>NQKSCMSNCSITSICEKPHEVCVAVWRKNDENITLETVCHDPKLTYH<br>GFTLEDAASPKCVMKEKKKPGETFFMCSCSADECNDNIIFSEDYNTS<br>NPDIPPHVQKSVNNDMIVTDNNGAVKLPQLCKFCDVRFSTCDNQKS<br>CMSNCSITSICEKPHEVCVAVWRKNDENITLETVCHDPKLTYHGFTL<br>EDAASPKCVMKEKKKPGETFFMCSCSADECNDNIIFSEDYNTSNPD | bFISTv.2.1 |
| 12 | MYRMQLLSCIALSLALVTNSAPTSSSTKKTQLQLEHLLLDLQMILNGI<br>NNYKNPKLTRMLTAKFYMPKKATELKHLQCLEEELKPLEEVLNLAQ<br>SKNFHLRPRDLISNINIVLELKGSETTFMCEYADETATIVEFLNRWIT<br>FCQSIISTLQKSDVEMEAQKGEMICVTCNRTAHPLKHVNNDMIVTDN<br>NGAVKLPQLCKFCDVRFSTCDNQKSCMSNCSITSICEKPQEVCVAV<br>WRKNDENITLETVCHDPKLTYHGFTLEDAASPKCVMKEKKKPGETF<br>FMCSCSSDECNDNIIFIPPHVQKSVNNDMIVTDNNGAVKLPQLCKFC<br>DVRFSTCDNQKSCMSNCSITSICEKPHEVCVAVWRKNDENITLETVC<br>HDPKLTYHGFTLEDAASPKCVMKEKKKPGETFFMCSCSADECNDNII<br>FSEDYNTSNPD | bFISTv.3 |
| 13 | MYRMQLLSCIALSLALVTNSAPTSSSTKKTQLQLEHLLLDLQMILNGI<br>NNYKNPKLTRMLTFKFYMPKKATELKHLQCLEEELKPLEEVLNLAQ<br>SKNFHLRPRDLISNINIVLELKGSETTFMCEYADETATIVEFLNRWIT<br>FCQSIISTLQIPPHVKSDVEMEAQKGEMICVTCNRTAHPLKHVNNDM<br>IVTDNNGAVKLPQLCKFCDVRFSTCDNQKSCMSNCSITSICEKPQEV<br>CVAVWRKNDENITLETVCHDPKLTYHGFTLEDAASPKCVMKEKKK<br>PGETFFMCSCSSDECNDNIIFSEDYNTSNPDIPPHVQKSVNNDMIVTD<br>NNGAVKLPQLCKFCDVRFSTCDNQKSCMSNCSITSICEKPHEVCVAV<br>WRKNDENITLETVCHDPKLTYHGFTLEDAASPKCVMKEKKKPGETF<br>FMCSCSADECNDNIIFSEDYNTSNPD | bFISTv.3.1 |
| 14 | MYRMQLLSCIALSLALVTNSAPTSSSTKKTQLQLEHLLLDLQMILNGI<br>NNYKNPKLTRMLTAKFYMPKKATELKHLQCLEEELKPLEEVLNLAQ<br>SKNFHLRPRDLISNINIVLELKGSETTFMCEYADETATIVEFLNRWIT<br>FCQSIISTLQKSVNNDMIVTDNNGAVKLPQLCKFCDVRFSTCDNQKS<br>CMSNCSITSICEKPHEVCVAVWRKNDENITLETVCHDPKLTYHGFTL<br>EDAASPKCVMKEKKKPGETFFMCSCSADECNDNIIFIPPHVQKSDVE<br>MEAQKGEMICVTCNRTAHPLKHVNNDMIVTDNNGAVKLPQLCKFC<br>DVRFSTCDNQKSCMSNCSITSICEKPQEVCVAVWRKNDENITLETVC<br>HDPKLTYHGFTLEDAASPKCVMKEKKKPGETFFMCSCSSDECNDNII<br>FSEDYNTSNPD | bFISTv.4 |
| 15 | MYRMQLLSCIALSLALVTNSAPTSSSTKKTQLQLEHLLLDLQMILNGI<br>NNYKNPKLTRMLTFKFYMPKKATELKHLQCLEEELKPLEEVLNLAQ<br>SKNFHLRPRDLISNINIVLELKGSETTFMCEYADETATIVEFLNRWIT<br>FCQSIISTLIPPHVQKSVNNDMIVTDNNGAVKLPQLCKFCDVRFSTCD<br>NQKSCMSNCSITSICEKPHEVCVAVWRKNDENITLETVCHDPKLTYH<br>GFTLEDAASPKCVMKEKKKPGETFFMCSCSADECNDNIIFSEDYNTS<br>NPDIPPHVQKSDVEMEAQKGEMICVTCNRTAHPLKHVNNDMIVTDN<br>NGAVKLPQLCKFCDVRFSTCDNQKSCMSNCSITSICEKPQEVCVAV<br>WRKNDENITLETVCHDPKLTYHGFTLEDAASPKCVMKEKKKPGETF<br>FMCSCSSDECNDNIIFSEDYNTSNPD | bFISTv.4.1 |
| 16 | MYRMQLLSCIALSLALVTNSAPTSSSTKKTQLQLEHLLLDLQMILNGI<br>NNYKNPKLTRMLTAKFYMPKKATELKHLQCLEEELKPLEEVLNLAQ<br>SKNFHLRPRDLISNINIVLELKGSETTFMCEYADETATIVEFLNRWIT<br>FCQSIISTLQKSDVEMEAQKGEMICVTCNRTAHPLKHVNNDMIVTDN<br>NGAVKLPQLCKFCDVRFSTCDNQKSCMSNCSITSICEKPQEVCVAV<br>WRKNDENITLETVCHDPKLTYHGFTLEDAASPKCVMKEKKKPGETF<br>FMCSCSSDECNDNIIFIPPHVKSDVEMEAQKGEMICVTCNRTAHPLK<br>HVNNDMIVTDNNGAVKLPQLCKFCDVRFSTCDNQKSCMSNCSITSIC<br>EKPQEVCVAVWRKNDENITLETVCHDPKLTYHGFTLEDAASPKCVM<br>KEKKKPGETFFMCSCSSDECNDNIIFSEDYNTSNPD | bFISTv.5 |
| 17 | MYRMQLLSCIALSLALVTNSAPTSSSTKKTQLQLEHLLLDLQMILNGI<br>NNYKNPKLTRMLTFKFYMPKKATELKHLQCLEEELKPLEEVLNLAQ<br>SKNFHLRPRDLISNINIVLELKGSETTFMCEYADETATIVEFLNRWIT | bFISTv.5.1 |

| SEQ ID NO | SEQUENCE | DESCRIPTION |
|---|---|---|
| | FCQSIISTLQIPPHVKSDVEMEAQKGEMICVTCNRTAHPLKHVNNDM IVTDNNGAVKLPQLCKFCDVRFSTCDNQKSCMSNCSITSICEKPQEV CVAVWRKNDENITLETVCHDPKLTYHGFTLEDAASPKCVMKEKKK PGETFFMCSCSSDECNDNIIFSEDYNTSNPDIPPHVKSDVEMEAQKGE MICVTCNRTAHPLKHVNNDMIVTDNNGAVKLPQLCKFCDVRFSTCD NQKSCMSNCSITSICEKPQEVCVAVWRKNDENITLETVCHDPKLTYH GFTLEDAASPKCVMKEKKKPGETFFMCSCSSDECNDNIIFSEDYNTS NPD | |
| 18 | MYRMQLLSCIALSLALVTNSISAMVRSVECPPCPAPPVAGPSVFLFPP KPKDTLMISRTPEVTCVVVDVSHEDPEVKFNWYVDGVEVHNAKTK PREEQYNSTYRVVSVLTVLHQDWLNGKEYKCKVSNKGLPSSIEKTIS KAKGQPREPQVYTLPPSREEMTKNQVSLTCLVKGFYPSDIAVEWESN GQPENNYKTTPPVLDSDGSFFLYSKLTVDKSRWQQGNVFSCSVMHE ALHNHYTQKSLSLSPGKAPTSSSTKKTQLQLEHLLLDLQMILNGINN YKNPKLTRMLTAKFYMPKKATELKHLQCLEEELKPLEEVLNLAQSK NFHLRPRDLISNINVIVLELKGSETTFMCEYADETATIVEFLNRWITFC QSIISTLQKSDVEMEAQKGEMICVTCNRTAHPLKHVNNDMIVTDNN GAVKLPQLCKFCDVRFSTCDNQKSCMSNCSITSICEKPQEVCVAVWR KNDENITLETVCHDPKLTYHGFTLEDAASPKCVMKEKKKPGETFFM CSCSSDECNDNIIFIPPHVQKSVNNDMIVTDNNGAVKLPQLCKFCDV RFSTCDNQKSCMSNCSITSICEKPHEVCVAVWRKNDENITLETVCHD PKLTYHGFTLEDAASPKCVMKEKKKPGETFFMCSCSADECNDNIIFS EDYNTSNPD | bFISTv.6 |
| 19 | MYRMQLLSCIALSLALVTNSISAMVRSVECPPCPAPPVAGPSVFLFPP KPKDTLMISRTPEVTCVVVDVSHEDPEVKFNWYVDGVEVHNAKTK PREEQYNSTYRVVSVLTVLHQDWLNGKEYKCKVSNKGLPSSIEKTIS KAKGQPREPQVYTLPPSREEMTKNQVSLTCLVKGFYPSDIAVEWESN GQPENNYKTTPPVLDSDGSFFLYSKLTVDKSRWQQGNVFSCSVMHE ALHNHYTQKSLSLSPGKAPTSSSTKKTQLQLEHLLLDLQMILNGINN YKNPKLTRMLTAKFYMPKKATELKHLQCLEEELKPLEEVLNLAQSK NFHLRPRDLISNINVIVLELKGSETTFMCEYADETATIVEFLNRWITFC QSIISTLQKSVNNDMIVTDNNGAVKLPQLCKFCDVRFSTCDNQKSCM SNCSITSICEKPHEVCVAVWRKNDENITLETVCHDPKLTYHGFTLED AASPKCVMKEKKKPGETFFMCSCSADECNDNIIFIPPHVQKSVNNDM IVTDNNGAVKLPQLCKFCDVRFSTCDNQKSCMSNCSITSICEKPHEV CVAVWRKNDENITLETVCHDPKLTYHGFTLEDAASPKCVMKEKKK PGETFFMCSCSADECNDNIIFSEDYNTSNPD | bFISTv.7 |
| 20 | MYRMQLLSCIALSLALVTNSIPPHVQKSVNNDMIVTDNNGAVKLPQ LCKFCDVRFSTCDNQKSCMSNCSITSICEKPHEVCVAVWRKNDENIT LETVCHDPKLTYHGFTLEDAASPKCVMKEKKKPGETFFMCSCSADE CNDNIIFSEDYNTSNPDAPTSSSTKKTQLQLEHLLLDLQMILNGINNY KNPKLTRMLTAKFYMPKKATELKHLQCLEEELKPLEEVLNLAQSKN FHLRPRDLISNINVIVLELKGSETTFMCEYADETATIVEFLNRWITFCQ SIISTLQKSVNNDMIVTDNNGAVKLPQLCKFCDVRFSTCDNQKSCMS NCSITSICEKPHEVCVAVWRKNDENITLETVCHDPKLTYHGFTLEDA ASPKCVMKEKKKPGETFFMCSCSADECNDNIIFSEDYNTSNPD | bFISTv.8 |
| 21 | MYRMQLLSCIALSLALVTNSIPPHVQKSVNNDMIVTDNNGAVKLPQ LCKFCDVRFSTCDNQKSCMSNCSITSICEKPHEVCVAVWRKNDENIT LETVCHDPKLTYHGFTLEDAASPKCVMKEKKKPGETFFMCSCSADE CNDNIIFSEDYNTSNPDAPTSSSTKKTQLQLEHLLLDLQMILNGINNY KNPKLTRMLTAKFYMPKKATELKHLQCLEEELKPLEEVLNLAQSKN FHLRPRDLISNINVIVLELKGSETTFMCEYADETATIVEFLNRWITFCQ SIISTLQKSDVEMEAQKGEMICVTCNRTAHPLKHVNNDMIVTDNNG AVKLPQLCKFCDVRFSTCDNQKSCMSNCSITSICEKPQEVCVAVWRK NDENITLETVCHDPKLTYHGFTLEDAASPKCVMKEKKKPGETFFMC SCSSDECNDNIIFSEDYNTSNPD | bFISTv.9 |
| 22 | MYRMQLLSCIALSLALVTNSIPPHVKSDVEMEAQKGEMICVTCNRT AHPLKHVNNDMIVTDNNGAVKLPQLCKFCDVRFSTCDNQKSCMSN CSITSICEKPQEVCVAVWRKNDENITLETVCHDPKLTYHGFTLEDAA SPKCVMKEKKKPGETFFMCSCSSDECNDNIIFSEDYNTSNPDAPTSSS TKKTQLQLEHLLLDLQMILNGINNYKNPKLTRMLTAKFYMPKKATE LKHLQCLEEELKPLEEVLNLAQSKNFHLRPRDLISNINVIVLELKGSE TTFMCEYADETATIVEFLNRWITFCQSIISTLQKSDVEMEAQKGEMIC VTCNRTAHPLKHVNNDMIVTDNNGAVKLPQLCKFCDVRFSTCDNQ KSCMSNCSITSICEKPQEVCVAVWRKNDENITLETVCHDPKLTYHGF TLEDAASPKCVMKEKKKPGETFFMCSCSSDECNDNIIFSEDYNTSNP D | bFISTv.10 |

The invention claimed is:

1. A method of reducing or treating fibrosis in a subject in need thereof, the method comprising administering to the subject a therapeutically effective amount of a fusion polypeptide comprising:
an interleukin-2 (IL 2) polypeptide or a fragment thereof comprising an IL-2 receptor binding domain;
a first soluble TGFβ receptor II (sTβRII) polypeptide or a fragment thereof comprising a ligand binding domain;
and a second soluble TGFβ receptor II (sTβRII) polypeptide or a fragment thereof comprising a ligand binding domain,
thereby reducing or treating fibrosis in the subject.

2. The method of claim 1, wherein the IL-2 polypeptide comprises SEQ ID NO: 2 or 3, or a fragment thereof comprising an IL-2 receptor binding domain.

3. The method of claim 1, wherein the IL-2 polypeptide comprises an amino acid sequence having greater than about 80% sequence identity to SEQ ID NO: 2.

4. The method of claim 1, wherein the first sTβRII polypeptide, the second sTβRII polypeptide, or both, comprise amino acid sequence having greater than about 80% sequence identity to SEQ ID NO: 8 or SEQ ID NO: 9.

5. The method of claim 1, wherein the first sTβRII polypeptide, the second sTβRII polypeptide, or both, bind a TGFβ1 polypeptide, a TGFβ2 polypeptide, a TGFβ3 polypeptide, or any combination thereof.

6. The method of claim 1, wherein the first sTβRII polypeptide and the second sTβRII polypeptide bind a TGFβ1 polypeptide.

7. The method of claim 1, wherein the fusion polypeptide comprises an amino acid sequence having at least about 80% sequence identity to any one of SEQ ID NOs: 10-25.

8. The method of claim 1, wherein the administering comprises administering the fusion polypeptide to the subject by systemic administration.

9. The method of claim 1, wherein the administering comprises administering the fusion polypeptide to the subject by intravenous administration.

10. The method of claim 1, wherein the fusion polypeptide is included in a pharmaceutical composition, wherein the pharmaceutical composition comprises one or more pharmaceutically acceptable excipients, carriers, diluents, or any combination thereof.

11. The method of claim 1, wherein the subject is a human.

12. The method of claim 1, wherein the IL-2 polypeptide comprises an amino acid sequence having greater than about 95% sequence identity to SEQ ID NO: 2.

13. The method of claim 1, wherein the first sTβRII polypeptide, the second sTβRII polypeptide, or both, comprise amino acid sequence having greater than about 95% sequence identity to SEQ ID NO: 8 or SEQ ID NO: 9.

14. The method of claim 1, wherein the fusion polypeptide comprises an amino acid sequence having at least about 90% sequence identity to any one of SEQ ID NOs: 10-22.

15. A method of treating fibrosis in a subject in need thereof, the method comprising administering intravenously to the subject a therapeutically effective amount of a fusion polypeptide comprising an amino acid sequence having at least about 90% sequence identity to any one of SEQ ID NOs: 10-22, wherein the method reduces fibrosis in the subject.

16. The method of claim 15, wherein the fusion protein comprises an amino acid sequence having at least about 90% sequence identity to SEQ ID NO: 12.

17. The method of claim 15, wherein the fusion protein comprises an amino acid sequence having at least about 90% sequence identity to SEQ ID NO: 13.

18. The method of claim 15, wherein the fusion protein comprises an amino acid sequence having at least about 90% sequence identity to SEQ ID NO: 14.

19. The method of claim 15, wherein the fusion protein comprises an amino acid sequence having at least about 90% sequence identity to SEQ ID NO: 15.

20. The method of claim 15, wherein the fusion protein comprises an amino acid sequence according to SEQ ID NO: 12.

21. The method of claim 15, wherein the fusion protein comprises an amino acid sequence according to SEQ ID NO: 13.

22. The method of claim 15, wherein the fusion protein comprises an amino acid sequence according to SEQ ID NO: 14.

23. The method of claim 15, wherein the fusion protein comprises an amino acid sequence according to SEQ ID NO: 15.

* * * * *